(12) United States Patent
Vacca

(10) Patent No.: US 11,103,384 B2
(45) Date of Patent: Aug. 31, 2021

(54) DYNAMIC TAPING METHOD FOR INHIBITION AND ELICITATION OF SKELETAL MUSCLE TONE

(71) Applicant: Charise Vacca, Westerville, OH (US)

(72) Inventor: Charise Marie Vacca, Westerville, OH (US)

( * ) Notice: Subject to any disclaimer, the term of this patent is extended or adjusted under 35 U.S.C. 154(b) by 716 days.

(21) Appl. No.: 15/898,181

(22) Filed: Feb. 15, 2018

(65) Prior Publication Data

US 2018/0168847 A1 Jun. 21, 2018

Related U.S. Application Data

(63) Continuation-in-part of application No. 14/664,762, filed on Mar. 20, 2015, now Pat. No. 10,441,473.

(60) Provisional application No. 62/460,717, filed on Feb. 17, 2017.

(51) Int. Cl.
| | | |
|---|---|---|
| *A61F 13/00* | (2006.01) | |
| *A61F 5/40* | (2006.01) | |
| *A61F 13/10* | (2006.01) | |
| *A61F 13/06* | (2006.01) | |
| *A61F 13/02* | (2006.01) | |

(52) U.S. Cl.
CPC ............... *A61F 13/00* (2013.01); *A61F 5/40* (2013.01); *A61F 13/02* (2013.01); *A61F 13/0273* (2013.01); *A61F 13/061* (2013.01); *A61F 13/101* (2013.01); *A61F 13/104* (2013.01); *A61F 13/105* (2013.01); *A61F 13/107* (2013.01)

(58) Field of Classification Search
CPC ...... A61F 13/00; A61F 13/02; A61F 13/0273; A61F 13/06; A61F 13/061; A61F 13/064; A61F 13/10; A61F 13/101; A61F 13/104; A61F 13/105; A61F 13/107; A61F 5/00; A61F 5/01; A61F 5/0104; A61F 5/10; A61F 5/40
USPC ....................................... 602/5, 54, 60–62, 75
See application file for complete search history.

(56) References Cited

U.S. PATENT DOCUMENTS

| | | | | |
|---|---|---|---|---|
| 7,195,605 B1 * | 3/2007 | White | ................... | A61F 13/066 602/21 |
| 7,902,420 B2 * | 3/2011 | Kase | ..................... | A61F 13/025 602/55 |
| 8,742,196 B2 * | 6/2014 | Arbesman | ............. | A61F 13/066 602/54 |
| 9,433,526 B2 * | 9/2016 | Protasiewicz | ......... | A61F 5/0106 |
| 10,441,473 B1 * | 10/2019 | Vacca | ..................... | A61F 13/02 |
| 2002/0091348 A1 * | 7/2002 | Joseph | .................. | A61F 5/0104 602/75 |
| 2015/0217098 A1 * | 8/2015 | Hicken | .................... | B05D 5/00 602/1 |

* cited by examiner

*Primary Examiner* — Keri J Nelson
(74) *Attorney, Agent, or Firm* — The Richard Law Firm LLC; William B. Richards, Esq.

(57) ABSTRACT

Is a taping method that follows a specific set of rules based on anatomical and physiological patterns in humans. This taping method causes a change in skeletal muscle tone in the human body, when tape is directly applied to the skin of the human body over targeted tendons and surrounding structures going over joints. This taping method will inhibit the muscle tone in the antagonist muscle of the opposing side of the joint where the tape is applied, while simultaneously eliciting the agonist of the muscle that are attached by the tendon of the joint where the tape is applied.

14 Claims, 36 Drawing Sheets

DYNAMIC TAPING METHOD FOR INHIBITION AND ELICITATION OF SKELETAL MUSCLE TONE

FIELD OF THE INVENTION

The invention is in the field of neurological and orthopedic medicine. The invention relates to the elicitation and inhibition of skeletal muscle tone. It involves the application of elastic-like (dynamic) adhesive medical tape directly to the skin of the human body going over tendons and surrounding structures that cross joints. This application is a Continuation-in-Part of U.S. patent application Ser. No. 14/664,762 herein incorporated by reference.

BACKGROUND OF THE INVENTION

Applying adhesive medical tape to the human body was most widely used in orthopedic medicine to support joints in the human body. The tape limited the range of motion while providing support, typically to an injured joint. Orthopedic taping has also been used to prevent injury, reduce pain and swelling, as well as provide mechanical correction of ligaments and tendons. Typical sports taping techniques will revolve around the joint region. During the process of taping there are muscles and bones that are covered, however, there is no particular assessment involving the muscle and limited assessment of the tensile structures associated with the muscle.

There are also less traditional uses for the application of adhesive medical tape to the human body. The use of adhesive medical tape applied directly to the skin of the human body has also been claimed to be used to assist in postural support, edema control, acupressure, improving circulation, pain control, and to assist with either eliciting or inhibiting muscle tone. There have been different types of adhesive medical tape developed. These taping methods involve the application of the tape directly to the skin.

The specific claims that any of these taping processes are able to assist in either eliciting or inhibiting muscle tone are unfounded. Examinations of all these taping patterns do not reveal any specific organized pattern that would correlate with specific skeletal muscle structures that lay beneath the tape that contribute to controlling muscle tone on a permanent basis. A pattern is determined when it correlates with the anatomical structures underneath the tape. The anatomy corresponds with specific physiological structures. It is the immobilization of the physiological structures that affect the muscle tone. The medical studies in PubMed® revealed that none of the taping patterns claiming to assist with the muscle tone have produced any effective long-term results.

It would be advantageous to come up with a taping method that was able to elicit and inhibit muscle tone that was effective and was able to produce long term results. This would assist in the recovery of neurological and orthopedic injuries. It would also be advantageous to have an established known pattern that was repeatable with predictable results. In other words, it would be a theoretical taping process. Furthermore, the taping method would be best to encompass and show efficacy in all ages of the human population that had any neurological or orthopedic disorder.

BRIEF SUMMARY OF THE INVENTION

The present invention is a taping method. This dynamic taping method is used to correct a muscle imbalance by affecting the muscle tone which exists in human beings. This method allows a taping of a tendon and surrounding structures over a joint to change the muscle tone. This assists simultaneously with both the elicitation and inhibition of muscle contractions of both the agonist and antagonist. It will correct muscle imbalances in patients with central nervous system lesions and orthopedic injuries. After the taping methods are implemented, the patient will be able to utilize muscles and new muscle movement patterns some of which were never functional before. They could also return to some previous level of their muscular function. These results will occur regardless of their chronological age or the age of their injury; however, it works the fastest with the smaller muscles. Larger muscles take longer to correct.

The method of dynamic joint taping can inhibit muscles that have always been tight or shortened. This can be due to high muscle tone (hypertonicity or spasticity). This taping method also can elicit muscles that have always been loose or lengthened. This can be due to low muscle tone (hypotonicity). This method performs both the inhibition and the elicitation simultaneously. The taping method does not always necessarily take away any previous movements or movement patterns; however, it will now for the first time allow new musculoskeletal movement patterns and overall muscle tone changes that allow these new more normal movement patterns. The participant's overall muscle tone will change.

For example, with the elicitation of hypotonic muscles, the patient will now be able to use their thumb in a more functional pattern. The extent of the speed of the muscle tone changes and more normalized movement patterns is dependent on many factors. There are varying degrees of changes to being able to completely integrate into a new normal movement pattern, (or re-balancing the muscle imbalance that previously existed). There are also results that vary depending on the extent of the injury, the age of the injury, compliancy of the taping method, medical history, and the age of the patient.

The taping method reconnects the central nervous system lesions by the afferent nervous system pathways. This is reconnected by impacting directly the sensory nervous system. The proprioceptors and mechanoreceptors are the receptors that are causing the impact. It reestablishes electrical and chemical communication distally from the afferent pathways to the central nervous system. This afferent pathway will reconnect the central nervous system and allow a change of muscle tone to occur through the efferent pathway. The patient will be able to use muscles because the central nervous system is undergoing neurogenesis and or synaptogenesis. The terms synaptogenesis and neurogenesis will be used interchangeably. The terms are implying that there is a regeneration of nervous system tissue. The efferent and afferent pathways in the peripheral nervous system of the somatic nervous system need to be intact or partially intact for this to occur. This neurogenesis can occur with congenital or after birth injuries. Examples of injuries before birth are cerebral palsy and in utero cerebral vascular accident. Examples of injuries after birth are cerebral vascular accident, spinal cord injury, traumatic brain injury, and seizure disorders.

This taping method is different from all the previous taping methods because this method is causing the central nervous system to undergo regeneration (neurogenesis) process that is elicited from the sensory system. The afferent pathway is communicating to the brain, which causes a corrected output to the efferent nervous system. The output becomes corrected by the tape controlling the proprioceptors and mechanoreceptors. They are controlled by immobilizing the sensory structures. The taping method is redefining the way that the entire nervous system works in our current accepted standards. It could also be stated that it is confirming hypotheses that have been formulated but not yet proven. The hypotheses that will be addressed are the following: neuroplasticity of the nervous system, synaptogenesis, neurogenesis, regeneration, function of the transcortical reflex (long latency reflex or long loop reflex), reciprocal innervation, functions of various proprioceptors and mechanoreceptors. It is possible to have neurogenesis occur from sending information initiating from the afferent nervous system.

The new physiological concept from this taping method is that humans do not have to have the origin of the signal coming from the central nervous system to control muscle tone. The proprioceptive and mechanoreceptor system is the source of changing the muscle tone. This sets up the targeted agonistic muscle for a contraction and the antagonistic muscle for inhibition or muscle tone relaxation. The location of these structures allows the reestablishment of the muscle tone in the motor units that have been impacted by the tape.

The inhibition and elicitation taping process is briefly described as follows: The elicitation and inhibition taping process occurs simultaneously and changes the muscle tone, allowing the joint to move. The tape is always capturing the joint in order to get the bones to move. This is true for eliciting movement in each type of joint as classified as small, medium and large joints. The most favorable order of applying the tape is distal to proximal in the joint that is moving in the human body. The tape that is applied with tension will have an elastic nature to create a spring-like characteristic in the taped region. The dynamic adhesive medical tape is applied to the skin and parallel over the muscle's tendons and surrounding structures. The dynamic tape can also be applied over some of the skin that is also not directly over the tendons. It will capture the tendons of the specific joint that is being elicited to move. There will be enough tape applied to the surface area of the skin to be able to move the joint or joints the practitioner is trying to elicit. The practitioner will also need to determine the amount of degrees they want the joint to move, without compromising the participant's skin. There are different steps to take depending on the size of the joint.

The small joint taping process (such as finger extension) is as follows; the tape will cross the joint and can capture part of the tendon. The more aggressive will capture the whole tendon whereas the most aggressive techniques will capture the myotendinous junction or junctions and beyond of the muscle. The tape will capture the joint with the tape that the practitioner is eliciting movement. The dynamic medical adhesive tape maintains tension the entire time it is on the participant's skin. An additional step would also include taping the synergists to the agonist that the practitioner is targeting. This would further recruit additional tension and therefore would immobilize additional proprioceptors and mechanoreceptors.

The process in medium joints are similar with one difference. There is an added step to the more aggressive approach of taping beyond the myotendinous region as well as beyond the tendon. The medium joint taping process is as follows: The tape will cross the joint and can capture part of the tendon. The aggressive technique includes the whole tendon. The more aggressive technique captures the myotendinous junction. The most aggressive technique passes the myotendinous junction and beyond the muscle, as well as beyond the tendon. The dynamic medical adhesive tape maintains tension the entire time it is on the participant's skin. An additional step would also include taping the synergists to the agonist that you are targeting, to further recruit in additional tension and immobilize additional proprioceptors and mechanoreceptors.

The taping process in large joints is as follows: The tape will cross the joint and can capture the whole tendon. The more aggressive technique captures the myotendinous junction of the muscle involved in the movement. The most aggressive technique passes the myotendinous junction and beyond the muscle, as well as beyond the tendon. This increases the lever arm length of the tape. The larger joints also will require more tape to capture the entire joint as shown with the knee joint in FIGS. 31 through 36. The dynamic medical adhesive tape maintains tension the entire time it is on the participant's skin. An additional step would also include taping the synergists to the agonist that the practitioner is targeting, to further recruit in additional tension in order to immobilize additional proprioceptors and mechanoreceptors.

The specific components of this taping method are noted as follows: This taping method is one in which the practitioner applies flexible or dynamic (elastic-like) medical adhesive tape to the skin over a joint and in parallel to as well as over the tendons, without penetrating the skin; this is to immobilize proprioceptors and mechanoreceptors to control tone in a skeletal muscle that has the following components and processes: joints, bones, muscles, fascia, retinaculum, tensile structures, ligaments, tendons, proximal and distal myotendinous junctions, reciprocal inhibition, reciprocal innervation, autogenic inhibition, autogenic excitation, immobilize, spike train response, tonic and phasic stretch reflex, myotatic reflex, inhibit, elicit, activate, deactivate, tonic and phasic reflex, Golgi tendon reflex, inverse myotatic reflex, short loop reflex, short latency reflex, long loop reflex, long latency reflex, transcortical reflex, neurogenesis, synaptogenesis, proprioceptor, fascial mechanoreceptors, myotendinous junctions, muscle spindle fibers, nuclear bag and chain fibers, Golgi tendon organs, Paciniform corpuscles, Pacinian corpuscle, Ruffini endings, interstitial type III and IV muscle receptors, and the extrafusal muscle fibers (which have an inherent ability to contract), length-tension of the muscle. Each structure will be described in detail as well as their role in eliciting an increase in muscle tone that is required for a muscle to contract.

The tape is applying both tension and pressure to the tendons and surrounding tensile structures, creating a length tension force upon the muscle where the tendon is attached to the Golgi tendon organ. The Golgi tendon organ initially activates when the tension is first placed, and then the tape immobilizes (deactivates) the structures. It interferes with the afferent part of the motor system. The result will be diminished or absent reflex of the Golgi tendon reflex (inverse myotatic reflex). The reversal of the typical response occurs. The result will be autogenic excitation. The muscle spindle fibers are then immobilized (deactivated) to the opposing muscle. It interferes with the afferent part of the motor system. The result will be a diminished or absent reflex of the stretch reflex (myotatic reflex). The reversal of the typical response occurs. The result will be autogenic inhibition. In essence, the Golgi tendon organs and the muscle spindle fibers are reversing roles. Note that the Golgi tendon organ and muscle spindle fibers are mostly known for a quick stretch reflex; (phasic reflex). In this example it is a very slow sustained stretch that deactivated these structures in a different way (tonic reflex). It deactivated the Golgi tendon organ to cause an opposite response it is known to have and causes a contraction. The tape is keeping tension on the Golgi tendon organs and immobilizing as it is building up a sustained constant tension on the muscle and the myotendinous junction of the tendons the muscle is attached to. This is done while simultaneously inhibiting the antagonist that has diminished or absent signals from the muscle spindle fibers in a tonic stretch reflex.

The parent application, inventor, Dr. Charise Vacca, application Ser. No. 14/664,762 has many similar properties as this new patent that is being filed. This technique may be used with the previous method for improved participant outcome.

DETAILED DESCRIPTION

The novelty in this invention is specifically the pattern of the taping method. The pattern is designed to target specific physiological structures and or processes. These structures in turn cause the resulting muscle tone changes. This taping method elicits simultaneous inhibition of muscle tone of the antagonist and elicitation of the targeted agonist via the tendons and other structures that are taped.

During the inhibition process, the antagonist to the targeted muscle the practitioner wants to contract are inhibited by the lengthening of the belly of the muscle. This occurs in response to the contraction of the targeted muscles by the tape that is applied to the tendons over the specific joints. This causes deactivation of the muscle spindles fibers. It will cause a reverse of the stretch reflex. This is not just a simple phasic reflex and will be discussed in greater detail later in this patent.

During the elicitation process, the targeted muscle that the practitioner wants to contract are elicited by placing the elastic-like dynamic adhesive medical tape on the skin directly over the tendons, fascia, joint capsules, retinaculum, ligaments, and associated tensile structures. (And can go past the tendons.) It should encompass each joint or single joint that is involved in the movement (as the result of the contraction of the targeted muscle). This causes deactivation of the Golgi tendon organs and a reversal of the Golgi tendon reflex. This is also not just a simple phasic reflex and will be discussed in greater detail later in this patent.

It is also noted that with both the activation and deactivation responses there are other mechanoreceptors involved. They will also be discussed in greater detail later in this patent.

In this taping method, both elicitation and inhibition are occurring simultaneously. There is a joint or multiple joints the practitioner wants to move in a direction in the participant. The corresponding agonists and possible synergists would have increased muscle tone. The tension will increase in the muscle and in the muscles' tendons and will immobilize the Golgi tendon organs causing a contraction to the agonist. The opposing antagonists would lengthen and immobilize the muscle spindle fibers that would cause the muscle to relax, allowing an easier contraction or shortening of the agonistic muscles.

There are multiple factors to consider in this taping method. The overall method to consider is the FITS model. F represents frequency; this pertains to frequency of taping applied. The I stands for intensity; this refers to the intensity of the tape applied. Intensity incudes the amount of adhesiveness in the tape as well as the amount of pressure applied. It also includes how much of the tendon and the myotendinous junction is involved. Additionally, it includes how far up the muscle the tape is applied past the myotendinous junction. T represents time. This represents the amount of time the tape is left on. The longer the tape is left on consecutively, the more effective the outcome. It also takes into consideration how much time the tape is on the participant's body in different periods of time, meaning there is a break in the wearing of the tape. The practitioner will determine how many consecutive hours a participant can tolerate the tape being on their skin, without compromising the patient's skin. It is theorized that the nervous system is reestablishing, or establishing a neurological connection for the first time. It takes time for the new pathway to develop and for neurogenesis to occur in the brain and any pathways that were damaged. The nervous system requires the constant nerve firing that is occurring from the reversal of these reflexes for as long as possible, to lay down the new neural networks that are correcting the muscle imbalances. When the tape is removed, the nerve firing stops that was sending the reversal information of the reflexes from the afferent pathway. The tape is no longer immobilizing the Golgi tendon organs and muscle spindle fibers (or other fascial mechanoreceptors.) It has been noted in one participant that I have treated; a permanent change has not yet occurred. In theory, there was not enough time for the nervous system to reconstruct the permanent connection and tone correction. The longer the amount of consecutive time the tape is on the participant's body, the more it is constantly firing and communicating information from the afferent (sensory) pathway. This communication is a reversal communication of the stretch reflex (myotatic reflex) and Golgi tendon reflex (inverse myotatic reflex). This causes change in the damaged brain and any pathways to repair. The efferent (motor) response leads to a permanent outcome. The S stands for specificity. This refers to the specific nature in the area that is applied, as well as how it applied. It is following an activation (phasic phase) and (a reversal) activation in the (tonic phase) of the physiological structures that exist in anatomical structures. The tape should be applied to immobilize the sensory structures the practitioner is targeting. This is another component to consider in the taping process. The practitioner should have knowledge of anatomy, physiology, and an understanding of integrating the significance of a participant's medical conditions in order to be able to safely and properly tape a participant.

The property of the tape will be taken into consideration before proceeding with the application of dynamic medical adhesive tape. There are 10 different properties.

The first property is the substance the tape is composed of. It will be elastic-like tape to recreate the tension of a tendon as well as the pull on the myotendinous region as the muscle tightens and shortens during a muscular contraction. It is also referred to as dynamic tape, and more specifically dynamic adhesive medical tape.

The second property of the tape is the width of the tape. The width will be able to encompass part of the tendon, the entire tendon, and/or structures surrounding the tendons.

The third property of the tape is the length of the tape. The tape will be long enough for any of the following: smaller sections of the tendon, down the entire length of the tendon, down the entire length of the tendon (as far as the myotendinous junction) of the muscles that would move the targeted joint. The tape may also go just past the myotendinous junction to increase the effectiveness of a longer lever arm of the tape.

The fourth property of the tape is the adhesiveness of the tape. It should have enough adhesive properties to be able to adhere to the skin, but not so much as to lose the elastic-like properties. Another tape will be used as an anchor to keep the dynamic tape from unraveling and coming off prematurely. The anchor tape will need to have a strong adhesive property and not stretch. This is also known as static tape.

The fifth property of the tape is the direction of application of the tape. It is most favorable to apply distally to proximally, in order to recreate the contracting and shortening of a tendon (and keep it in that position). The practitioner will be placing the origin of the movement on the lever arm that is targeted to move. For example, if the goal is to extend the leg, the first piece of dynamic tape will be applied to the fibula and tibia (pulling it up into extension) and bringing the tape up the leg and onto the more proximal bone (the femur).

The sixth property of the tape is the amount of tape that will be utilized. The assessment includes the number of joints involved, the participant's tolerance, and the size of the joints (larger joints will need more tape).

The seventh property of the tape is the duration of the wearing time for each taping session. The longer the duration time the tape is applied, the more favorable the outcome. The recommendation is to start with 1 day duration of wearing time and progress by adding one day at a time. This allows the practitioner to continually assess the participant's skin and their skin tolerance to the tape. The progress can be up to approximately 17 days, as long as no skin breakdown occurs. The nature of the dynamic tapes tends to last approximately 7 days before it starts to unravel. The practitioner can reapply the tape if it starts to unravel to enable the participant to continue to wear it for a longer period of time. This will be individually assessed with each participant.

The eighth property of the tape is its reapplication. This will be determined by the frequency of treatments and skin tolerance of the participant.

The ninth property of the tape is the assessment of its substances. The first concern is if it is latex free. It will also be assessed if it is hypoallergenic. The participant will be matched with the correct tape substances they are able to tolerate.

The tenth property of the tape is to assess the tension of the tape. The practitioner will apply the tape onto the participant with enough tension to get the targeted joint to move. The correct amount of tension needed during the application process will also be assessed. It is advisable to proceed with a more conservative approach, starting with less tension and increasing the tension as the participant is monitored. If the tension in the tape is too great against the skin, it could cause blistering and skin breakdown.

The property of the tendons, joints, joint capsules, tensile structures, ligaments, fascia, retinaculum, muscles, and surrounding anatomical structures will be taken into consideration before proceeding with the application of dynamic medical adhesive tape. There are 15 different properties to take into consideration.

The first property is the severity of the muscle tone imbalance. If a participant has very high muscle tone (also known as muscle spasticity, or hypertonicity) there will be more sheer forces at work on their skin. There should be caution taken with the selection of tension that opposes this type of high pressure. If the participant has high finger flexion tone when taping the finger joints into extension, exert caution as to not overly extend the fingers. The opposing flexion force will apply sheer forces onto the dorsal surface of the skin that is under the tape.

The second property is the surface area of the muscle or muscle groups. It will also include tensile structures involved such as tendons, ligaments, fascia and retinaculum, and joint capsules of the targeted joint. The larger muscles will require more tape going across the joint. It could possibly require longer tape to increase the lever arm, as well as to involve the myotendinous junction. When the myotendinous junction is involved, it is optimal to tape it in series or as close to in series as possible to immobilize the Golgi tendon organs.

The third property is the volume of the muscle or muscle groups involved in movement of the targeted joint. The larger muscles and muscle groups will require more tape and possibly longer tape to increase the lever arm of the tape, as well and to involve the myotendinous junction. The tape will end in series at the myotendinous junction. It can also extend beyond the myotendinous junction.

The fourth property is the action or group of action of the muscle or muscle groups and the direction of the action, focusing on the joint.

The fifth property is the length of the lever arm involved in the action. The longer the lever arm of the bones that are moving, the longer the strips of tape required. It may also require more separate pieces of tape to be able to move the joint.

The sixth property is the origin and insertion of the muscle or muscle groups involved in the movement of the joint.

The seventh property is the location and orientation of the tendons, and other tensile structures (ligaments, fascia and retinaculum, joint capsules) involved in joint movement. This will dictate the direction of tension and pull on the tape.

The eighth property is the number of joints that are involved in the movement, as well as which specific joints will be targeted to be activated to move. The direction of the movement will also be assessed.

The ninth property is the location and distribution of fascial mechanoreceptors and proprioceptors that will be immobilized by the tape.

The tenth property is the agonist/antagonist relationship of the muscle involved.

The eleventh property is the agonist/synergist relationship. The practitioner may elect to elicit muscle tone the synergists to cause a contraction to assist with movement of the targeted agonist and joint.

The twelfth property is the location and presence of vital structures such as veins, arteries, and nerves. These regions should be approached with caution and possibly completely avoided.

The thirteenth property is identifying the muscle imbalances that exist. This procedure is complicated, especially with neurological patients. Some examples of complicated items to evaluate are the following: primitive reflexes, integrated versus non-integrated reflexes, central nervous system injury reflexive patterns, upper motor neuron injuries, lower motor neuron injuries, compensatory patterns, synergy patterns, weak versus strong muscles, and skeletal structure based on structure of the bones (genu valgus, genu varus, scoliosis, kyphosis), and past musculoskeletal injuries.

The fourteenth property is the amount of tension required to cause movement of the joint. It consists of the amount of tension that is given to the tape as it is applied on the skin.

The fifteenth property is the overall length-tension relationship of the entire muscle in relation to itself, and the lever arms involved for the movement of the targeted joint.

The property of the participant's specific conditions will be taken into consideration before proceeding with the application of dynamic medical adhesive tape. There are six different properties.

The first property is the participant's medical condition. This would include but not be limited to the participant's age and skin condition, medical history, precautions, allergies (especially tape and latex allergies, banana allergies), and medications that cause skin sensitivity, or impact their muscle tone. Assess their muscle tone and in particular the amount of spasticity that exists in the participant. If the participant has a high amount of spasticity, the practitioner will consider the amount of tape tension, as well as how long to leave the tape on their skin. Tape removal instructions and allergy testing instructions are reviewed and given to the participant and/or participant's caregiver.

The second property is the proper sequencing to apply the tape on the participant: applying the tape distally to proximally along the joints and surrounding tensile structures, staying on the same side of the body, applying the tape laterally to medially, and in general going cephalo to caudal with the exception of the face/head/neck region. This region also has cranial nerve innervation, baroreceptors and vital veins/arties entering and exiting the region. Therefore, there is a possible sensitivity and a higher possibility of adverse reactions to the tape. The practitioner can tape in a more distally located region to assess participant's response. An example of this is to tape the fingers/hand before the shoulder region. It is recommended once a response is obtained and a participant can tolerate to proceed with cephalo to caudal. The participant's tone will continue to decrease as the tape is applied and will have a trickle-down effect to the more distal regions, and hence a desired cumulative effect. If the practitioner is taping all structures into extension, and the participant has the typical flexion synergy pattern with high tone, each extension elicitation pattern will have a cumulative effect of decreasing the overall flexor tone.

The third property is monitoring the patient's response throughout the entire taping process. Identify signs and symptoms to know when to abandon the taping for that day (e.g. vomiting, skin breakdown or lesions, excessive pain) or permanently.

The fourth property is evaluating sensitive areas. It is recommended to save the most sensitive areas for last (head/face/neck). Talk with the participant and/or the participant's caregiver regarding these areas. Also discuss with the participant the possible sensitive regions that are unique to them. Avoid wrapping around any limb in any way that can compromise circulation. For example, do not apply the tape of the distal interphalangeal joint over the end of the finger and anchor on the palmar side of the hand. This compromises the circulation to the region under the tape and can also have an impact on the nail bed of the participant.

The fifth property is the duration of time the tape can be left on the participant. This will be determined by each individual participant and should not exceed a time period in which skin breakdown would occur. It is recommended with the initiation of the tape to start with less time. It is recommended to start with 1 day and slowly increase the wearing time, while monitoring the participant's skin. Participants with very high tone are more prone to having skin breakdown because of increased friction caused by the increased muscle tone and tension of the tape. The duration time may need to be shortened in that scenario.

The sixth property is the positioning of the participant after taping is completed. Consider the role that gravity could play on the recently taped body part. Gravity and or positioning could elicit a reflex. The effect of the taping could be reduced. The region of the body that was taped is to be placed in a position that does not counter the desired effects of the practitioner's taping. Positioning pillows or an orthopedic splint to assist with correct positioning will assist in the efficacy of the recent taping. If the patient has one side of the body more affected into a typical flexion synergy pattern with increased spasticity, it would be beneficial that the participant sleeps on the involved side in a position that induces an asymmetrical tonic neck reflex position. The asymmetrical tonic neck reflex position will further reduce the tone of the involved body region by increasing the extensor tone on the affected side of the body, while simultaneously reducing the flexor tone on the affected side of the body.

The sequence of the taping technique has fourteen steps. The following 17 sequences are noted as follows in the next 17 paragraphs.

The first step is to obtain the complete participant's medical history.

The second step is to perform a tape allergy test. It should be performed for both the elastic-like dynamic tape as well as the anchor tape pieces that are static in nature and highly adhesive. The allergy test is completed 12 to 24 hours prior to beginning the taping process. The third step starts after the allergy test comes back negative in that 12- to 24-hour window of time.

The third step is to identify the muscle imbalances that exist. Observe and if needed measure range of motion. Assess the range of motion actively and passively. Pay attention to the tone when assessing the participant passively. Select the order of joints you want to have the participant move.

The fourth step is to perform gentle stretches to the selected muscles before taping and assess the participant's muscle tone. Inquire and observe if the skin is prepared for taping (lotion-free, shaved, etc.).

The fifth step is to determine the distal and proximal targets where the tape will be applied. Determine the proper length and if it will include the entire length of the tendon, and also the myotendinous junction of the targeted muscle. Determine if it is to also extend beyond the myotendinous junction and/or include additional tensile structures. The pathway of the tendon will be mapped out as well as the location of the myotendinous junction of the muscles, and other tensile structures and bones involved in movement of the joint.

The sixth step is to move the joint or joints. The practitioner will first move the joint or joints into the desired position. This can be done in a passive, active assisted, or in an active manner that would include passive or active assisted movement at end range of the desired movement.

The seventh step is to apply the dynamic tape to the targeted distal target on the distal bone of the joint that the practitioner wants to have the participant move. The practitioner will hold down the tape in place as they proceed to the next step to keep it from unraveling. This is most optimal to start distally. The practitioner can apply the tape proximally to distally as they apply pressure in the same manner as the tendon would move the joint.

The eighth step is to apply a stretch force or tension with the elastic-like tape as the practitioner is applying it to the skin of the participant. The tape is applied on the skin and in parallel to and encompassing part of or the whole tendon, and tensile structures (such as ligaments, fascia and retinaculum, and joint capsules) that the practitioner is targeting. Tension of the tape will be maintained as it is applied to the skin to maintain the new desired position of the joint. The tape will be gently pressed onto the skin going distally to proximally as the tension is kept on the tape. The final contact with the skin will be applied to the most proximal target on the skin after crossing the joint or joints.

The ninth step is to check the security of the tape. The practitioner will check the entire piece of tape to make sure it is secure while pressing on the tape distally to proximally. Once the tape is deemed secure then the anchor tape is applied. First apply a static adhesive medical tape distally to secure the dynamic tape and prevent unravelling. Then apply a static adhesive medical tape proximally to secure the second end of the tape. The amount of tension given to the dynamic tape is up to the practitioner. The tape should be acting like the tendon it is covering. The joints should be in the alignment the practitioner would like the participant's joints and limb to be positioned. Tape can also be applied to skin adjacent to the tendon. The larger the joint, the more dynamic adhesive tape that will be required to capture the tendon, and possibly a ligament and surrounding structures. The force is applied in the direction of the targeted tendon going over the targeted joints, and in the direction the tendon would perform normally. The practitioner is assisting in shortening the targeted joints and moving the desired appendage and/or joint.

The tenth step is to apply an anchor piece of tape at the distal end of the tape to avoid the tape from unravelling. The anchor tape will be static adhesive medical tape. It will be made of material that keeps it from stretching to allow for a secure anchor. The anchor tape will be large enough to secure the tape in all parameters and it will have a minimally longer or larger border to avoid causing skin irritation. The practitioner will select the size of the anchor tape to prevent any possible skin irritation to the participant.

The eleventh step is to apply an anchor piece of tape at the proximal end of the tape to avoid unravelling. The practitioner will follow the same steps as outlined in the previous paragraph.

The twelfth step is for the practitioner to examine the anchor tape placed both distally and proximally to deem that the dynamic tape is secure. An assessment will be made at this time to determine if any additional anchor tape is needed to further secure the tape. This is a step to take to increase the tape wearing time. The intention of this taping technique is to have the tape stay on the body as long as the participant can tolerate, and within skin guidelines to prevent any skin breakdown. The tape will also need to maintain its integrity while it is on the skin and may start to break down and lose its elasticity or unravel. The tape needs to be removed if either occurs.

The thirteenth step is to continue to tape all targeted joints repeating all previous outlined steps. Complete the most proximally located joints/bones/limbs first and then progress to more distally located joints.

The fourteenth step: If the more distal joints are in close proximity to the next joint that is to move, the distal ends of the tape can be captured by the proximal end of the next taping that is to occur. The tape can encompass the previous taping. This is recommended to overlap the tape to establish more stability of the distally placed previous tape.

The fifteenth step: Instruct the participant in the movement pattern that the practitioner would want to elicit. Have them repeat multiple times and, if possible, to fatigue. Observe and take measurements.

The sixteenth step: Instruct the participant and/or participant's caregiver in the home exercises program the practitioner would want them to perform, to reinforce the new movement patterns the practitioner was able to elicit.

The seventeenth step is to review the tape wearing times and tape removal instructions to the appropriate participant and/or participant's caregiver. Specify the duration of time the participant will wear the tape. The initial phase of determining the skin tolerance is a short wearing time as the practitioner determines skin tolerance. Start out with 1 day and increase up to one day at time duration. After the tolerance is established then it is recommended to have them wear the tape as long as possible to create a good neurological pathway. The duration of time the tape is being worn is correlated to the long-term outcomes. It is recommended to attempt anywhere from 7 and approximately up to 17 days depending on skin tolerance and avoiding any skin breakdown. The tape can be reapplied if it does unravel before 17 days and the skin tolerance has been determined for the longest wearing time. The skin will require a rest period in between taping times of typically 24 to 48 hours before reapplication of the tape.

In summary, it is a dynamic taping method of at least one joint to control the tone in the associated skeletal muscles. Three different joint sizes are included in this dynamic taping method. The joint sizes are small, medium and large. Each joint will contain a joint capsule, fascia, retinaculum, and at least one tendon, at least one ligament, and associated tensile structures. The skeletal muscle includes an agonist muscle and antagonist muscle. Each will include a distal and proximal surface and a distal and proximal myotendinous junction. It will also include the joint and associated skeletal muscles. The joint and associated skeletal muscles will have proprioceptors and mechanoreceptors. These are structures named as follows: Golgi tendon organs, Paciniform corpuscles, Pacinian corpuscles, Ruffini's endings, interstitial type III and IV muscle receptors, muscle spindle fibers containing nuclear bag and chain fibers. The dynamic adhesive medical tape is applied in tension to the dorsal surface. This method will capture at least one joint to immobilize proprioceptors and mechanoreceptors.

The dynamic adhesive medical tape lengthens the antagonist muscle spindle fibers. This will immobilize the nuclear bag and chain fibers, thereby inhibiting muscle tone in the antagonist, and eliciting muscle tone in the agonist. The antagonist muscle is in relation to the agonist that the practitioner elects to elicit. When the tape immobilizes the nuclear bag and chain fibers, there is loss of information on muscle length. This causes an interruption with the afferent part of the reflex resulting in a diminished or absent reflex. The immobilization prevents the ion channels from opening and closing. This will cause a hyperpolarization in the muscle cells of the muscle spindle fibers (containing the nuclear bag and chain fibers). The group 1a and II afferent fibers do not become depolarized, since they are now hyperpolarizing. They will not send an action potential (nerve impulse). The neuron that synapses with the afferent nerve (the interneuron) is becoming depolarized. It will depolarize the paired sensory neuron in the reciprocal innervation. This opposing sensory neuron will send an action potential (nerve impulse) up to the brain to both the cerebellum and through the transcortical reflex (long loop reflex) directly to the cerebral cortex. The cerebral cortex (via the transcortical reflex) and the cerebellum will send a nerve impulse back efferently (motor nerve) to the opposing motor neuron. This opposing muscle will fire and cause an increase in muscle tone. This is in the agonist. It will reverse the stretch reflex (the myotatic reflex). It has a cumulative effect to stop the elicitation process in the antagonist. It will inhibit muscle tone and muscle contraction in the antagonist muscle. It is important to note when referring to the agonist, this is the muscle that was selected by the practitioner to elicit, and it is the muscle that has the dynamic tape on it. This is also the muscle that the tape is applied on. To clarify, if the finger flexors have high tone, they are the antagonist.

If the finger extensors have low tone, they are the agonist where the dynamic tape is applied. The muscle spindle fibers in the finger flexors are immobilized and the finger flexor will relax. The finger extensors will contract.

The dynamic adhesive medical tape applies tension to the Golgi tendon organs of the agonist. This immobilizes the Golgi tendon organs of the agonist muscle, thereby eliciting muscle tone in the agonist and inhibiting muscle tone in the antagonist. The agonist is the muscle the practitioner chooses to elicit and has the dynamic tape applied to it. The dynamic adhesive medical tape immobilizes the Golgi tendon organs. This causes an interruption with the afferent part of the reflex resulting in a diminished or absent reflex. There will be a loss of information on muscle tension. The Golgi tendon organs that are housed in collagen are unable to move back and forth since they are immobilized. This will stop the ability of the ion channels to open and close. They will not be able to pinch and activate 1b afferent nerve (also known as the Golgi afferent nerve). The cells will become hyperpolarized. This will stop the pinch and activate the 1b afferent nerve (also known as the Golgi tendon afferent nerve) since they are hyperpolarized, they will not send an action potential to activate the 1b interneuron inhibitory neurons. It will not inhibit the agonist. The inhibitory sensory interneuron will depolarize and send nerve impulses to the cerebellum and the cerebral cortex (through the transcortical reflex) and back down to the antagonist. This will cause decreased muscle tone to antagonist. To clarify, this causes a reversal of the Golgi tendon reflex. It has the cumulative effect to stop the inhibition process of the agonist. This will elicit muscle tone and cause a contraction of the agonist muscle. This could happen due to the possibility of mixed effects on the interneurons. To clarify, the afferents can exhibit both a co-excitability and co-inhibitory effect on this interneuron. In theory, the agonist that houses the immobilized Golgi tendon organs is being depolarized to cause an increase in muscle tone because the interneuron is not receiving the input to depolarize the inhibitory interneuron. It will cause a co-excitation response and excite the agonist. This is the reverse of the known autogenic inhibition reflex (also known as the inverse myotatic reflex). It will also inhibit muscle tone in the antagonist.

The dynamic taping steps further comprise of applying the tape across at least one joint to capture a part of the joint tendon. It can also comprise of applying the tape across at least one joint to capture the entire joint tendon. It can also comprise of applying the tape across at least one joint to capture the entire joint tendon and the myotendinous junction of the muscle associated with the joint. This last step can further comprise applying additional pieces of tape in parallel to the first piece of tape across at least one joint to capture the entire joint tendon and the myotendinous junction of the muscle associated with the joint. It can further comprise of applying additional pieces of tape in parallel to the first piece of tape, across at least one joint to capture the entire joint tendon and the myotendinous junction of a second muscle associated with the joint. It can further comprise of applying the tape across at least one joint to capture the entire joint tendon, the myotendinous junction and at least a portion of the muscle associated with the joint. It can further comprise of applying the tape across at least one joint to capture the entire joint tendon, the myotendinous junction and at least a portion of the muscle associated with the joint and at least a portion of a second muscle associated with the joint.

This dynamic taping method can further comprise of taping the synergist muscles along with the agonist muscles to recruit additional tension and immobilize additional proprioceptors and mechanoreceptors.

This method comprises the step of taping distally to proximally across at least one joint. This method further comprises the step of applying the tape laterally to medially, and cephalo to caudal.

This dynamic taping method also immobilizes the Paciniform corpuscles and Pacinian corpuscles. This dynamic taping method immobilizes Ruffini's endings and interstitial type III and IV muscle receptors. These fascial mechanoreceptors assist in locating the placement of the motor unit (located in the agonist muscle) to the central nervous system. This assistance in location gives the brain additional awareness of the existence of the motor units (located in the agonist muscle) that house these receptors. This enables the brain to allow increased muscle tone and muscle contraction to the correct location of the agonist.

The following is a specific example of the taping technique on a small joint, and multiple joints of the $3^{rd}$ digit. The process that is illustrated in FIGS. 1 through 10 will be described.

The assumption is that the practitioner has taken all the properties into account prior to taping the participant. The example will now proceed with the steps to the tape application, beginning with the application of the tape.

An example would be attempting to get the participant's 3rd digit distal interphalangeal joint to extend. This is illustrated in FIGS. 2 through 4. The first technique is eliciting the distal interphalangeal joint to extend. This is a simple process of applying the tape to the proximal nail bed. It is applied distally to proximally, with tension, while the tape is pressed down onto the skin. It goes over the distal interphalangeal joint, capturing the part of the extensor digitorum tendon that is located underneath the joint capsule. The tape causes the joint to extend. The anchor tape is then placed distally to the end of the tape and then proximally to the end of the tape.

An example of attempting to get multiple joints to extend is seen in FIGS. 5 through 7. The second technique is getting three joints to extend the $3^{rd}$ digit. This is a more complicated process of applying the tape to the proximal nail bed distally. Hold the tape in place as tension is applied to the tape distally to proximally while the tape is pressed down onto the skin. The tape goes over the distal interphalangeal joint, the proximal interphalangeal joint and the metacarpophalangeal joint. The tape is capturing the part of the extensor digitorum tendon that is located underneath the joint capsules. The tape causes the joints to extend. The anchor tape is then placed distally to the end of the tape and then proximally to the end of the tape.

An example of attempting to get multiple joints to extend with eliciting additional structures beyond the joints, such as the myotendinous junction of the muscle that extends all the joints. Specifically, the $3^{rd}$ digit as seen in FIGS. 8 through 10. The third technique is getting three joints to extend the $3^{rd}$ digit, as well as gong into the myotendinous junction of the extensor digitorum. This is a more complicated process of applying the tape to the proximal nail bed distally and holding it in place as tension is applied to the tape. The tape is applied distally to proximally as the tape is pressed down onto the skin as it goes over the distal interphalangeal joint, the proximal interphalangeal joint and the metacarpophalangeal joint, and finally extending down into the distal myotendinous junction of the extensor digitorum muscle. The tape is capturing the part of the extensor digitorum tendon that is located underneath the joint capsules and inserting into the distal myotendinous junction. The tape causes the joints to extend and immobilizes the Golgi tendon organs that are in series in the myotendinous junction of the extensor digitorum. This is an added piece of additional immobilization by going into the myotendinous junction where the Golgi tendon organs are most dense. The anchor tape is then placed distally to the end of the tape and also proximally to the end of the tape.

An exception to note in this taping process is if a participant has an injury like a skin lesion. The practitioner can bypass this lesion and still tape an appendage. If there is a cut on the distal interphalangeal joint region of the $3^{rd}$ digit of the hand, the practitioner can bypass the distal interphalangeal joint region and apply tape along the tendon, going over the proximal interphalangeal joint and the metacarpophalangeal joint. This is pointing out that taping can occur anywhere along the tendon and still produce results.

A splint can shorten the joint spaces; however, it does not add true tension. The tape adds true tension and pressure whereas a splint does not. A splint, whether static or dynamic, does not address the specificity principal that was earlier presented. It is a general external device applied and does not activate or deactivate (immobilize) the specific proprioceptors and mechanoreceptors that are needed to elicit a permanent neurological change. A splint does not add specific pressure or tension to site specific structures. It only gives general pressure. The tape is site specific and pressure/tension specific to have an impact on the structures lying beneath the tape. The structures are sensitive to pressure and or tension and will only respond as they are neurologically wired to respond.

This dynamic neurological taping technique has significant long-term effects. The participants are able to maintain the changed muscle tone without the tape on the skin. This is evidence of a permanent long-term outcome. This is stating that the tape was able to communicate effectively in a reflexive feed-back loop system. The long loop reflex is restored. This is from the afferent pathways to the brain and returning via the efferent pathways. In essence, the old damaged pathway has been regenerated. This is occurring in the brain. This is theoretical neurophysiology. It is noted that the participants that were treated had a brain injury that has intact peripheral nervous systems; including the afferent and efferent pathways. This is what leads to the conclusion that neurogenesis is occurring in the brain. It is most likely occurring in the motor cortex of the cerebral cortex. The participant is now able to actively move their region of the body that was targeted, without any needed constant input from the tape any longer. It has established a rebalancing of the muscle tone by overall decrease of the pathological tone patterns that were occurring.

There have been participants that have participated in this new dynamic taping technique. All of the participants that have been treated with success are patients with upper motor neuron lesions. There was an attempt to treat a participant with a lower motor lesion with no results. There were no results with the initial taping of three days. It is plausible that with lower motor neuron lesions it will take longer to see results due to the pathways involved. It would involve stimulation from the brain that is intact and require neurogenesis in the pathways down the entire length of the affected limb. This is a longer length to travel and repair versus repairing the motor cortex in the brain. This is further evidence that this taping method is causing neurogenesis in the brain. This is also evidence that the long loop reflex pathways are also being regenerated. The upper motor neurons are in descending pathways. Lesions in the upper motor neuron cause increased muscle tone. They also lose or have a diminished long loop reflex.

A participant was treated that has increased muscle tone (hypertonicity) that had no volitional movement of a pollex (thumb) and very high tone. After the taping process begins, the first result will be decreased tone occur (a participant's caregivers notice changes in the participant's own muscle tone; they report the participant is waking up with their hand fully relaxed, which is a new state. The progression continues with the ability to gain the ability to move their thumb. The movement is moving the thumb in an involuntary manner. This is suggesting the cerebellum is readjusting to sending out both increased muscle tone to the elicited agonist and decreased muscle tone to the inhibited antagonist. The extrapyramidal pathway that transmits the involuntary movement signals is carrying this new signal from the cerebellum. This is simultaneously happening with the possible regeneration process of the long loop reflex (transcortical reflex), and regeneration in the cerebral cortex.

The participants continue to progress to being able to control the digit voluntarily suggesting that the motor cortex that controls voluntary movement is undergoing synaptogenesis or neurogenesis. It is able to undergo neurogenesis because the long loop reflex is transmitting information to it to assist in the restoration process. The long loop reflex is responsible for the cerebral cortex to undergo neurogenesis. It is noted that the speed of the immediate response in the participant is very fast. This leans towards the possibility that the long loop reflex can be easily activated again with a stimulus. It may be restored immediately once a stimulus is perceived in the sensory system that sends an impulse through the long loop reflex. When comparing the amount of time it takes for the change in muscle tone to occur permanently takes much longer.

This is supporting the hypothesis that neurogenesis is occurring in the brain. This takes time to completely restore. It is uncertain if any type of restoration is occurring in the long loop reflex. Perhaps none is needed in this reflexive loop and it only needs a stimulus to reactivate this loop system. The motor cortex is sending a signal through the pyramidal pathway of the impacted motor units from the tape. The participant has volitional control of some of the motor units in the muscle. The initial volitional control of the thumb is not fluid. Neurogenesis takes time. This further reinforces the theory that neurogenesis is occurring in the cerebral cortex. It seems likely this would specifically be in the motor cortex region of the cerebral cortex.

The participants will initially struggle more with movement in muscles that are larger and have less muscle spindle fiber density in them. There are a few factors involved in this scenario. The muscle spindle fibers have less influence (literature supports they are the main structures to control tone), the larger size of the muscle makes it more difficult to get an optimal length-tension relationship for a contraction, and there is a higher volume of motor units that are deeper that the tape is unable to impact in the initial stages. The participant will have the same muscle that will be controlled in an imbalanced manner by the cerebellum and cerebral cortex. To clarify, the unaffected motor units will still be under control of the cerebellum (involuntary movement) and still sending nerve impulses down the extrapyramidal tract.

An example would be the biceps and triceps muscles. When the participant has no volitional control of these muscles, it is solely being controlled by the cerebellum and the nerve impulse travels down the extrapyramidal pathway. The motor units that are directly impacted by the tape are first being controlled by the cerebellum and traveling down the extrapyramidal pathway (as well as the rest of the motor units in the muscle that are not impacted by the tape). After neurogenesis occurs the specific motor units that were impacted by the tape convert to being under control of the motor cortex in the cerebral cortex. The nerve impulses now travel through the pyramidal pathway because they can volitionally control the specific motor units in the muscle. There will (in the early phases of treatment) still be a struggle with the high muscle tone, because not all of the motor units in the muscle have converted to being controlled by the motor cortex and are still under control of the cerebellum.

Participants have transformed through these phases of neurogenesis. When the tape is placed for the very first time there is a response that is drastic. When the tape is in place the long loop reflex is being activated by the tape for the first time since the injury. When the tape is removed there is a decrease in response if any at all. It is because there has not yet been enough time for neurogenesis to occur. The participant's progress in treatment and the next step that occurs is there is a reduction in muscle tone. They cannot move the muscle volitionally. In the next phase they are able to move the muscle but not on command. The movement occurs intermittently. They progress to another phase of being able to move the muscle on command. The participant progresses to a stronger contraction. They also progress with being able to perform more repetitions of the movement (this occurs at all phases of strength grades). They progress even more to being able to move through the whole range of motion. To clarify this point further by example, note as follows: When the participants start to gain volitional control they may not be able to move the muscle through the whole range of motion.

In physical therapy that is graded as below normal muscle strength. This grading system is not used in participants with upper motor lesions; however, it will be used to further explain and clarify what is being observed. A participant that was treated progressed from starting out with having a flexion synergy pattern and very high tone with a clenched first and no isolated movements of digits. They then progress to a grade given as poor (full range of motion with gravity eliminated) the movement is not fluid since it is still partially under control of the cerebellum. The participant's will next progress to fair minus (less than full but greater than ½ range of motion against gravity. The movement is still not fluid, but it becomes more fluid as the cerebral cortex is taking over more control. The participants progress to fair (movement in full range against gravity). The length of time it takes to progress depends on the severity of the injury. This taping method is so new that the participants are still undergoing the rehabilitation process. No participants have yet to progress to completely normal strength; however, there has not been enough treatment time. This technique has been utilized on participants for just over approximately 13 months.

This is also suggesting that the original motor units that are impacted by the tape and being converted to control of the cerebral cortex are gradually being able to become more and more under volitional control. The cerebral cortex is gradually gaining control over additional motor units that were not originally impacted by the tape. This is occurring as neurogenesis is progressing. In theory, all of the motor units should eventually be under control of the cerebral cortex. The participant with an upper motor neuron lesion is returning to their previous normal state in the converted motor units. This suggests that the brain has the ability to completely repair regardless of when an injury has happened.

The longest duration time of an upper motor neuron injury that was treated in a participant was 33 years old. The participant has been able to maintain volitional control of converted motor units. In theory, the brain has the properties of neuroplasticity at any age and at any time after an injury occurs. Neurogenesis can occur in the brain through receiving input from the sensory nervous system. The tape is continually sending impulses from the sensory nervous system up through the dorsal roots and up through the long loop reflex. These impulses are causing the nerves to become active again. This is why it is recommended to leave the tape on to allow this constant transmission that is igniting the regeneration via long loop reflex to the cerebral cortex. The long loop reflex has sensory and motor components. This is to clarify that the long loop reflex is going from the sensory nervous system up into the cerebral cortex and back down through the motor nervous system. The exact location or locations that neurogenesis is occurring has not yet been confirmed by any diagnostic modalities, such as with an MRI.

The results of the participants that were treated have consistently demonstrated an outcome predicted by theory, specifically two examples are given. In the first example, a participant was selected for this dynamic taping that had a traumatic brain injury approximately 33 years ago. The participant had been unable to move their hallux (big toe) on the affected left side since the initial injury. After applying dynamic tape to the participant's hallux, they were immediately able to extend the hallux for the first time since the injury that occurred decades ago. The participant was also able to perform this movement one week later without the tape in place. The tape was left on for only 1 day. They have had previous taping treatments to other regions of his body. They are already undergoing neurogenesis. This could explain why it only took one day when taping a new joint for the first time. This is the shortest observed amount of time it took to elicit a new movement.

Another example is a participant that has cerebral palsy. The participant had severe high tone in their ankle invertors on their affected side. The participant had dynamic tape placed on the ankle evertors. They tolerated up to 5 days duration of the tape in place. They have been intermittently taped for just under one-year duration with permanent results of significantly decreased inversion. Prior to the taping, the participant was walking with such severe inversion they were unable to walk without a marked limp. When they jumped, they would land into ankle inversion with severe plantarflexion. They were unable to get the foot flat or straight. They also required wearing an ankle foot orthoses to be able to support the ankle joint and walk without severe inversion. Currently they are able to jump with 2 feet take off higher than 4 inches, and land flat foot on the affected side without eliciting the ankle into plantar flexion. The gait pattern is only a slight limp, secondarily to a flattening out of the foot, with the ankle being into much less inversion. They are able to ambulate with a normal walking cadence without an ankle foot orthoses and very minimal inversion. These changes have been persistent when the dynamic tape is not in place on their invertors.

There are many other participants that have had results from the dynamic taping. In general, of all of the participants treated, the quickest response to change muscle tone has occurred in the fingers. This could be due to the fact that the muscles that are involved in fine motor control have the most densely packed muscle spindle fibers in these types of muscles. The muscle spindle fibers are powerful in the manner that they have the fastest conduction of sensory axons in the peripheral nerves. This further adds evidence to the role that muscle spindle fibers are involved in controlling muscle tone. All of the participants that were treated have exhibited flexion synergy patterns. The population of participants with upper motor neuron lesions will typically exhibited high tone or spasticity in their flexors and low tone or hypotonicity in their extensors. There is one exception in a participant with a nonintegrated (exaggerated) asymmetrical neck reflex. In this particular muscle imbalance, there would be taping to elicit some flexors. This would occur to enable a reversal of the reflex to get it to integrate. The reversal of this reflex would be the most optimal way to improve the overall muscle tone of this participant.

The etiology of how skeletal muscle tone functions and how to control it has been elusive. There are multiple theories that are attempting to explain how it works. The human body operates to always maintain homeostasis in every system in the body. The nervous system is included in trying to maintain a sense of homeostasis or balance. The somatic nervous system controls skeletal muscle in both a voluntary and involuntary manner. It is trying to maintain muscle tone balance of the agonist and antagonist to allow a smooth operation of movement (while maintaining stability) through space against gravity. It operates in feedback loop systems just like the other systems do to maintain homeostasis. The balance is maintained by elicitation of the agonist while inhibiting the antagonist to allow movement. Movement is more complicated. Co-contractions do occur to stabilize the body. The muscle pairs (agonist and antagonist) contract concentrically (agonist) and eccentrically (antagonist) to allow the joints and the body to be stable against gravity.

In rehabilitation, the eccentric muscle contraction will strengthen and occurs before the concentric muscle contraction. The eccentric muscle contraction is more essential to our survival since it arouse from the need to fight against gravity. An example would be hanging from a tree with your arms. The muscles will sustain an eccentric contraction from a much longer time (just hanging there versus doing a pull up (or move the muscle concentrically against gravity). In theory, muscle tone function can be explained when taking a closer look at how the myotatic reflex and inverse myotatic reflexes are working. These tonic reflexes are polysynaptic and have a long loop reflex; these types of reflexes directly go to the cerebral cortex. This includes Golgi tendon organs and muscle spindle fibers. The literature that was reviewed did not reveal there is evidence that other tonic reflexes utilized the long loop reflex such as the asymmetrical tonic neck reflex, and sustained pressure fascial mechanoreceptors. In theory, it is logical that they would also use the long loop reflex. There is evidence with the dynamic taping process that they do, based on the results that have been obtained.

There are also multiple pathways for the myotatic and inverse myotatic reflexes to travel to the central nervous system. The pathways are labeled as short latency reflex (short loop reflex) and long latency reflex (long loop reflex, also the transcortical reflex) there is also a volitional pathway that is not a reflex. These pathways travel at different speeds. The short loop reflex is the fastest. It is a protective response and acts quickly. The long loop reflex is slower because it is going up farther into the central nervous system to the cerebral cortex. The volitional movement that the cerebellum helps to modulate is going at a speed in between the short loop and long loop reflexes. Volitional movement occurs at a faster rate than the long loop reflex. These pathways have been labeled according to their velocity. The long latency reflex takes longer because it is traveling up higher in the nervous system to the brain. The short loop is the very quick protective reflex that goes directly to the spinal cord. It synapses there (monosynaptic) and comes directly back to the muscle. Both the Golgi tendon organs and the muscle spindle fibers have this short latency reflex arc with no communication to higher central nervous system levels.

The myotatic reflex (caused by the muscle spindle fibers) will cause a contraction of the muscle that received the stretch and an inhibition to the opposing muscle. The inverse myotatic reflex (caused by the Golgi tendon organs) will cause a relaxation of the muscle that received the tension and send an excitatory response to the opposing muscle. Both of the muscle proprioceptors also have two other pathways that they follow. They also travel to the cerebellum that assists in voluntary movement and is not defined as a reflex since it involves voluntary control. The long loop reflex that they follow is also known as the long latency reflex and the transcortical reflex. The name of this reflex is as it implies it is going to the cerebral cortex.

This transcortical reflex has been a scientific mystery for decades. Basic components are still left unanswered. The importance of this reflex has not yet been understood by scientists. A theory is proposed that this transcortical reflex is the answer to how the participants that have treated have been able to have a permanent change in muscle tone. A theory is that the participants are undergoing neurogenesis in the cerebral cortex. This is occurring because of the ability to transmit nerve impulses back and forth (afferent and efferent) to the cerebral cortex by the transcortical reflex. These impulses will send electrical and chemical impulses to the brain tissue that was damaged allowing them to be excitable again. Depolarization and repolarization are just like a muscle contraction in a motor unit; it follows the physiological principal of all or none. Once a neuron is excited it will send this impulse to the other neurons and reinitiate the pathways.

Studies show that the long loop reflex term is not only restricted to the Golgi tendon organs and the muscle spindle fibers. There are studies that show that the long loop reflex occurs with stimulation that is occurring in the mechanoreceptors that are not the proprioceptors (Golgi tendon organs and muscle spindle fibers). Studies show that theses long loop reflexes occur with stimulation to the dorsal roots. The dorsal root carries sensory information not only from the muscle proprioceptors but also from the mechanoreceptors. This provides further evidence that the other mechanoreceptors may assist in the restoration of the muscle imbalances by giving additional information to the cerebral cortex of the exact location of the muscles. There are studies that support this hypothesis. These other fascial mechanoreceptors will be explained in further detail.

The afferent nervous system sensory receptors are constantly moving and changing. This occurs in response to a stimulus that they are designed to perceive length (stretch) or tension. Studies have shown that participants with brain injuries have either had greatly diminished or completely lost their long loop response. In theory, the tape restores this long loop reflex response. Not only is the long loop restored, it is the pathway to allow neurogenesis to occur. The participants that were treated, reveal an immediate response (muscle tone changes) when the tape is placed on the skin. The response is not as fast as volitional muscle control.

The Golgi tendon organs and the muscle spindle fibers are the two proprioceptors that are most involved in human neuromusculoskeletal dynamics. There are involuntary adjustments by the somatic nervous system that are made to help with regulating balance and posture. There is evidence in assisting with ambulation in the literature. The literature presents more evidence that the muscle spindle fibers are more involved in regulating ambulation. There are studies that also include evidence that the Golgi tendon organs are also involved in ambulation. This would provide evidence that both the muscle spindle fibers and the Golgi tendon organs are initiating muscle contractions. Therefore, reflex connections of muscle afferent neurons can initiate increasing muscle tone and muscle contraction. This provides further evidence that the long latency reflex is involved in muscle tone control.

Other mechanoreceptors will be presented that are also involved from a theoretical stance. There is evidence that the Golgi tendon organs communicate with one another in the spike train response. A theory could be that all proprioceptors and mechanoreceptors communicate with each other constantly to modulate movement of the body fluidly through space while responding to gravity.

The participants that have been treated have not received functional magnetic resonance imaging after being taped. This would be a suggested intervention to use as a diagnostic tool to determine what is occurring in the brain. It would be optimal to compare with previous magnetic resonance imaging to see what changes may have occurred. This would be a recommended study to pursue in the future. Taking before taping treatment and after taping treatment functional magnetic resonance imaging of participants with brain damage, that affects the motor system and muscle tone.

The length of time to produce a permanent change is approximately 1-5 days. It is optimal to leave the tape on as long as up to approximately 17 days for the longest wearing duration of time. The long-term firing of the neurons occurs longer and allows for regeneration as the tape is left on for longer periods of time and allows for neurogenesis or synaptogenesis to occur. This is a plausible explanation for the permanent neurological changes that are seen in the participants that have been treated with this new dynamic taping technique. The responses are occurring in the muscles that are directly affected by the tape. They are also occurring in an overall response of a reduction in muscle tone.

This dynamic taping method is recreating the components of a muscle contraction. It can be compared to the placement of an exoskeleton on the body. The tape is placed on the skin with tension over a tendon (and tensile structures). This causes a physiological response due to the location, pressure and tension of the tape. Proprioceptors (and mechanoreceptors) are designed to respond to pressure and tension. This dynamic taping produces both effects of pressure and tension. This exoskeleton is then kept in place with tension and left on for 1 to 17 days or more. This position of the exoskeleton immobilizes the afferent receptors. The reflex needs to be initiated by an afferent neuron. Since the afferent (sensory) receptors are immobilized, they will not cause the afferent neuron to fire. The opposing neuron involved in reciprocal innervation will fire and cause a reversal of the reflex. The anatomical structures that directly coincide with this dynamic taping are located in the myotendinous junctions, tendons, ligaments, retinaculum, joint capsules, fascia and tensile structures around and in the joint itself. This taping process uses elastic-like tape applied with tension and maintains tension while on the participant. The application of the tape over the tendon and other tensile structures of the agonist muscle will have the effect of increasing muscle tension in the agonist. This will create a more optimal length-tension relationship to set up increased muscle tone to allow for a muscular contraction. The length-tension relationship in a muscle needs to be optimal to create the right environment for the contractile components of the muscle to contract. The extrafusal muscle fibers inherently want to contract. It will also set up a relaxation or lengthening response in the antagonist. This will assist in a better contraction in the agonist.

Prior to going into more detail about the involved proprioceptor and mechanoreceptors, a brief summary of how these sensory structures respond will help to further explain what the tape is doing to them from a physiological standpoint. These sensory structures have components in them that are designed to perceive specialized stimulus. The sensory structures that are involved with muscle tone sense the stimulus of stretch(or lengthening), tension, change in the rate of length and change in the rate of tension, deep touch, vibration, sustained pressure, lateral pressure, rapid and sustained mechanical tension pressure and pressure changes. The receptors that have a phasic response have a minor role in assisting in muscle tone. They do not communicate to higher levels up to the brain. They are still perceived briefly by the cerebral cortex which is what they were designed for as a protective response. They assist in the moment they are stimulated by the tape to alert the brain to the location of the muscle that is being elicited. The receptors that have a tonic phase have a major role in controlling muscle tone. The primary proprioceptors that have the role in controlling muscle tone are the Golgi tendon organs and the muscle spindle fibers. The receptors with a tonic phase are polysynaptic and synapse in both the spinal cord and go to higher levels in the brain.

The designs of these receptors have components that move and respond constantly to a stimulus. When the components move, they allow an ion channel to open. This occurs by allowing an influx of sodium to flood into the cell and changing the cells resting potential to a more positively charged internal state that builds up as more sodium rushes in. This will cause a depolarization of the cell which increases the action potential and cause the neuron to fire. The cell then undergoes a repolarization process when the ion channels close. The positive charge buildup opens the potassium channel and it leaves to allow the cell to return to its resting state. This sets the cell up for another stimulus to occur and start the depolarization process again. This is sending constant sensory information to the central nervous system to keep it informed of what is occurring in the body to allow for adjustments to occur. This is a factor to consider in the taping process. The tape immobilizes these moving structures in these sensory cells. All of the sensory cells will have moving components to allow for the perception of a stimulus. This does not allow the ion channels to open and close. It is stopping the movement (or partially stopping the movement). It will then not allow the cell to go through the depolarization or repolarization process. This will hyperpolarize the cell and will cause a depolarization of the sensory interneuron. It will send an impulse up to the brain and back down through the efferent system. The brain is able to detect the location where the impulse came from. The participant can feel the tape on their body. This could also be an explanation of why tape can help with reducing pain since this pathway is firing, and the nervous system is only able to perceive a certain amount of information. This could help diminish the detection of pain impulses.

The physiological reactions that occur in the Golgi tendon organs and the muscle spindle are divided into both tonic and phasic phases. The phasic phase initially occurs as the tape is applied to these structures. This is to alert any practitioner to be aware of when this is occurring when applying the tape. The pull on the belly of the muscle in the antagonist of the taped muscle stretches the muscle spindle fibers and will cause a momentary increase in muscle tone as the phasic response occurs. It quickly converts the tonic phase and the reverse response occurs. The pull on the myotendinous junction will initially activate the Golgi tendon organs that are arranged in series. The pull on the tendon and other tensile structures listed will also activate other Golgi tendon organs. This will cause a momentary decrease in the muscle tone as the phasic response occurs. This will quickly convert to the tonic phase and the reverse occurs. The timing of the conversion to occur is very fast. Results in a change in muscle tone will occur quickly, within a few seconds, and can cause an unexpected response from the participant and any additional witnesses.

Both of these proprioceptors have reciprocal innervation. This means that the opposing muscle is also innervated by these structures. The phasic responses will help the muscle perform the protective response by activating an opposite reaction in this muscle to allow the phasic reflex to occur. In the muscle spindle fiber, the opposing muscle will relax or have decreased muscle tone. In the Golgi tendon organ, the opposing muscle will contract or have increased muscle tone. These responses are also momentary in the phasic phase and will quickly convert to the tonic phase and the reverse occurs.

The muscle spindle fiber myotatic (stretch) reflex is well known. This is the phasic portion of the reflex. Muscle spindle fibers are sensitive to stretch, and they relay changes in muscle fiber length (stretch) and the rate of the change in length (stretch) of the muscle fibers. This reflex causes a contraction of the agonist as a protective response and inhibition to the antagonist in response to a quick lengthening of the agonist muscle. This is a stretch reflex that is sensing a quick rate of change in the length of the muscle. An example of a stretch reflex is the stretch reflex of the quadriceps femoris muscle (the well-known patellar tendon reflex).

The theoretical physiology for inhibition relates to the muscle spindle fibers in the antagonist to the agonist muscle the practitioner is eliciting. Muscle spindle fibers are most densely located in the belly of a muscle. They are located in parallel to the muscle fibers. The muscle spindle fibers are intrafusal fibers located in parallel to the extrafusal muscle fibers. This was already covered previously in the specifications. There are a few additional points to clarify and a brief summary to simplify. These fibers are not just phasic (monosynaptic) in nature with their response. They are also tonic (polysynaptic) in their response. As previously stated, one of their synapses is what is commonly called long latency reflex. This long latency reflex goes directly to the cerebral cortex. The information is being processed at the voluntary and conscious part of the brain and undergoes neurogenesis. After the dynamic tape is applied, the agonist is now tightening/contracting or shortening. The antagonist is receiving signals of inhibition in a theoretical manner that involves the muscle spindle fibers in a different way. The movement of the agonist lengthens the antagonist. This occurs by keeping the belly of the muscle (of the antagonist) in a more stretched position. This lengthening will partially or completely immobilize the nuclear bag and chain fibers in the intrafusal muscle fibers (these are located in parallel to the extrafusal muscle fibers). The gamma motor neurons control the muscle spindles and keep them from going into a slack position. When they go into this slack position there is a loss of afferent action potential, and this results in a loss of information regarding muscle length. When the extrafusal muscles typically contract the gamma motor neuron also should contract (coactivation). The gamma motor neurons and the alpha motor neurons stop firing and this overall effect will cause decreased muscle tone, and cause relaxation. The opposing neurons will fire and cause a contraction in the agonist. The agonist that the practitioner elected and has the tape placed on the muscle. This is the reverse of the known stretch reflex (myotatic reflex).

The theoretical physiology for elicitation relates to the Golgi tendon organs. Golgi tendon organs are located most densely in the myotendinous junctions of the muscles. Specific details on the physiological mechanism with the Golgi tendon organs that occur to elicit increased muscle tone were previously covered. A brief summary to simplify is included. The application of the elastic-like tape with tension, placed over the tendons, and pulling on the myotendinous junction will cause a deactivation of the Golgi tendon organs, as these structures are immobilized by the constant tension of the tape. Golgi tendon organs are designed to sense tension as well as the rate of change of the tension in the muscles. Most are located in the myotendinous junction and some are located in the tendons, attachment areas of aponeuroses, and in ligaments of peripheral joints and joint capsules, and other tensile structures such as attachment regions of aponeuroses. The pull on the myotendinous junction will initially activate the Golgi tendon organs that are arranged in series. The pull on the tendon and other tensile structures listed will also activate other Golgi tendon organs. This will soon convert to a deactivation of the Golgi tendon organs. This well-known protective response is the Golgi tendon organ reflex (inverse myotatic (and phasic) reflex). This is also known as the autogenic inhibition. The application of the tape with tension immobilizes the Golgi tendon organs and would cause the reversal of the typical phasic reflex and would produce an effect known as autogenic excitation. It will also inhibit the antagonist.

Studies also support that Golgi tendon organs are not just inhibitory. There are studies that show that the Golgi tendon organs are activated during ambulation in humans. This is considered to be a reflex reversal and autogenic inhibition is suppressed. This response will cause autogenic excitation. This is suppressed by inhibiting the 1b interneuron. This interneuron when it is suppressed stops the inhibition process of a muscle contraction. It is allowing a muscle to contract. These studies reveal that the Golgi tendon organs are involved in eliciting a muscle contraction. This is supportive evidence to the previous paragraph. There is also a phenomenon known as the spike train response. This response allows for additional recruitment of other Golgi tendon organs in the region. This is further evidence that proprioceptors communicate with each other in the dynamic taping method, the Golgi tendon organ is being inhibited. In theory, the other Golgi tendon organs in the region would also start shutting down in response to the inhibition, following the logic that they communicate. It is logical that these structures would follow either an excitation or and inhibition response together.

The tape causes a lengthening of the muscle spindles fibers and immobilizes them in this position. Muscle spindle fibers are sensitive to lengthening. The tape with tension immobilizes the Golgi tendon organ as they are sensitive to tension. Both are having interference in the afferent feedback and in the reflexive feedback loop system (reflex arc or reflex loop). Therefore, the motor neurons are affected. The muscle spindle fibers are immobilized (or partially immobilized) in position. The Golgi tendon organ are immobilized (or partially immobilized) in a position. This no longer allows the constant needed movement and change in position, of these sensory structures requires giving feedback by constantly being activated and stopping (not deactivated) and performing the usual and known responses. This causes the reverse effect of their well-known phasic reflexes. The afferents are no longer supplying the sensory information and interrupt the reflexive feedback loop system. This impacts the brain and efferent system. The motor neurons to the muscle spindle fibers are excitatory. Since they are no longer getting the feedback, they will not fire, thus causing inhibition of the muscle. The motor neurons to the Golgi tendon organs are inhibitory and since they are no longer getting the feedback from the afferents they will not inhibit, thus causing an excitation of the muscle.

The dynamic tape applied with both tension and pressure will also have an impact on mechanoreceptors. The fascial mechanoreceptors of interest in this dynamic taping method will be some of the mechanoreceptors. In theory, they play a much smaller role in assisting with controlling muscle tone. The assistance they provide is in helping the brain with the location of the motor unit involved. When the tape pulls onto the muscle along the tendon and pulls onto the myotendinous junction; this also activates the Paciniform corpuscles (in the phasic stage) that are also activated by pressure. These are fascial mechanoreceptors. The Paciniform corpuscles sense rapid pressure changes and vibration that contribute to kinesthetic sense. The known response of these structures is that they contribute to kinesthetic sense as well as a role in movement. These are located in the myotendinous junction as well as the joint capsules. These locations are also where the Golgi tendon organs are located. There is little information about this mechanoreceptor. It is likely that these structures are assisting the Golgi tendon organs and assisting in additional aid to help the brain find the muscle and contribute to an isolated muscle contraction. The dynamic tape applied around the joint capsules is applying pressure and is initially activating these structures. They are then deactivated by the tape since their sensory structures are immobilized by the tape. The opposite response would be expected, as demonstrated in all past examples of immobilizing sensory structures. The known response is ambiguous in the literature. This would cause a hyperpolarization of the sensory cells in these structures. This would cause a depolarization in the interneurons that synapse to these cells. This would send an action potential (nerve impulse) up to the brain and could assist with better locating the agonist muscle to contract.

The Pacinian corpuscle (also known as the lamellar corpuscle) is also a fascial mechanoreceptor. It is located in the deep skin (also known as the dermis) both hairy and non-hairy regions, especially in tendinous sites, the deep portion of joint capsules, and spinal ligaments. These structures respond to rapid deep touch and vibration. These structures have an afferent nerve in the center. There are layers of surrounding discs. The usual response when a touch or pressure is perceived occurs. The response is that the inner disc will stay stationary and the outer discs will turn. When the discs turn it opens up an ion channel that allows sodium (a positive charge) to flood into the middle and cause a change in the charge to be positive which cause a depolarization and increase in action potential that build to a threshold to allow the afferent nerve (that is located there) to fire and send out an impulse. The cell needs to repolarize and return to its resting potential to get ready to have another reaction. These receptors need the pressure to keep changing to have the afferent nerve to keep sending out impulses. The application of tape immobilizes the discs and do not allow them to turn so there is no longer a release of sodium into the channels (or the release of potassium back into the channels). This prevents the depolarization of the afferent nerve fiber and does not allow the afferent nerve to send out an impulse. It would cause a depolarization of the nerve it synapses to (sensory interneuron). This would fire and send a nerve impulse to the brain on a continual basis. These mechanoreceptors are "helper" mechanoreceptors that aid in the location of the motor unit they lie within. In theory, the central nervous system will detect this and the exact location in the motor unit which will further help the brain locate the muscle. These would be immobilizing structures underneath the tape that is applied all along the skin. This would cause the opposite response that these structures are usually performing. In theory, it will reverse the known response of this fascial mechanoreceptor. The literature suggests it is related to kinesthesia; however, in the literature review the specifics were not found. The nervous system is now able to further locate the location of the motor unit and allows the brain to reconnect with the muscle and assist in the process of neurogenesis.

The Ruffini endings (also known as bulbous corpuscles) are fascial mechanoreceptors. These respond to sustained pressure. These are located in deep skin, ligaments of peripheral joints, joint capsules and dura mater, and other tissues associated with regular stretching. The tape that is applied over the ligaments and along the tendons would assist in the elicitation process of the agonist muscle. The tape pressure would be immobilizing these Ruffini endings. The deactivation of these would further help to locate the muscle and help the brain find the muscle to assist in muscle contractions. These structures are more involved in the elicitation taping process of the muscle since they respond to sustained pressure which would be the tape that is applied, and the location of where the tape is applied. The tape is left on for long periods of time immobilizing the Ruffini endings. This would cause an opposite reaction that these structures are used to performing. They also play a role for the lateral and tangential forces applied by the tape. The taping of the ligaments and capsules would directly impact these structures and deactivate them. This would in theory, cause the opposite response that these structures are usually performing. They are known to detect tension and movement control. The nervous system is now able to further locate the exact location of the motor unit and allows the brain to reconnect with the muscle and assist in the process of neurogenesis Interstitial type III and IV muscle receptors respond to both rapid and sustained mechanical tension and pressure changes. These are also fascial mechanoreceptors. The tape is applied in any direction these mechanoreceptors are immobilized and deactivated beneath the tape. They are actually located almost everywhere in the body (they are found inside bones). They exist in fascia. These are the most abundant mechanoreceptor. The application of the tape will initially activate and then quickly become deactivated. They will be deactivated because the sensory structures become immobilized, and in theory would cause the opposite known affect. The literature suggests they assist in the reduction of muscle tone. Therefore, by immobilizing them, they would have the opposite effect of increasing muscle tone. The tape that is placed over these mechanoreceptors contributes to increasing muscle tone. This mechanoreceptor takes a small role. The muscle proprioceptors as supported by literature, are the primary sensory structures in controlling muscle tone. These receptors, in theory, assist in the brain locating the location of the structures involved. This assists in gaining the specificity of location of specific muscle location and allows assisting in isolated muscle contractions. They are known to respond as a mechanoreceptor. In theory, they assist the brain in finding where the motor units of the muscles are located. The more surface area that the tape covers the more receptors that are immobilized (deactivated). Muscles have fascia covering them and therefore the sustaining portion of the interstitial type III and IV muscle receptors are being activated underneath the tape.

In theory, this is why many taping techniques are so popular, even though they do not have any organized pattern (to activate proprioceptors) and are randomly placed. These random and non-specific techniques still are impacting the interstitial type III and IV muscle receptors through the fascia. This will increase body awareness and muscle tone of the participant while the tape is being worn. Due to the non-specific nature of these other taping patterns, these patterns do not activate other proprioceptors that are the primary controllers of muscle tone (such as the muscle spindle fibers or Golgi tendon organs). There are no long-term results from a neurological standpoint in permanently controlling muscle tone. The communication to the brain is nebulous. It is theorized the dynamic taping recruits these fibers and strengthens the specificity of the location of the motor units to the brain. They further assist in increasing muscle tone in the taped agonist muscle.

Muscle fibers (extrafusal) are themselves inherently contractile. Extrafusal muscle fibers are designed to contract easily. They require an optimal length-tension relationship to allow a contraction to occur. The application of dynamic tape creates tension to the muscle and shortens the muscle and sets up the muscle fibers themselves to contract. The extrafusal muscle respond and contract in their specific motor unit.

The proprioceptors and fascial mechanoreceptors (as helpers to the proprioceptors), are driving the ability of skeletal muscles to contract and relax. They are assisting in the rebalancing of muscle tone. When examining the spike train response of the Golgi tendon organs, it is noted they are communicating to each other. The Golgi tendon organs are communicating in the region; it seems very likely they would in turn be able to communicate to the muscle spindle fibers and other fascial mechanoreceptors as a group. In theory, it is logical that all of the proprioceptors and fascial mechanoreceptors are communicating with their own groups and with each other.

Figure 1:
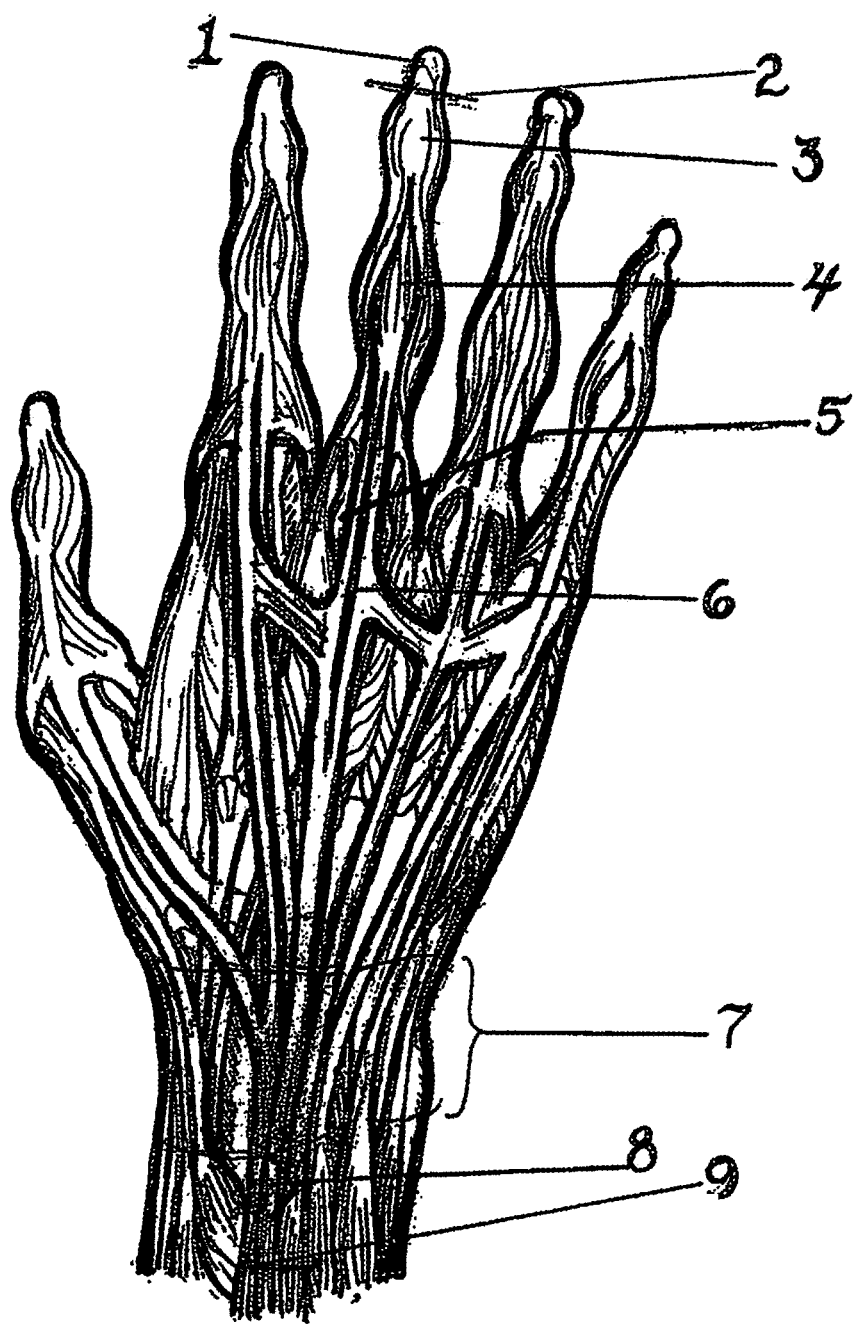
FIG. 1. is a drawing of the right hand anatomical structures: distal phalanx 1, proximal region of nail bed 2, distal interphalangeal joint 3, proximal interphalangeal joint 4, metacarpophalangeal joint 5, extensor digitorum tendon 6, extensor retinaculum 7, myotendinous region of the extensor digitorum of the 3d digit 8, and extensor digitorum muscle 9.
Figure 2:
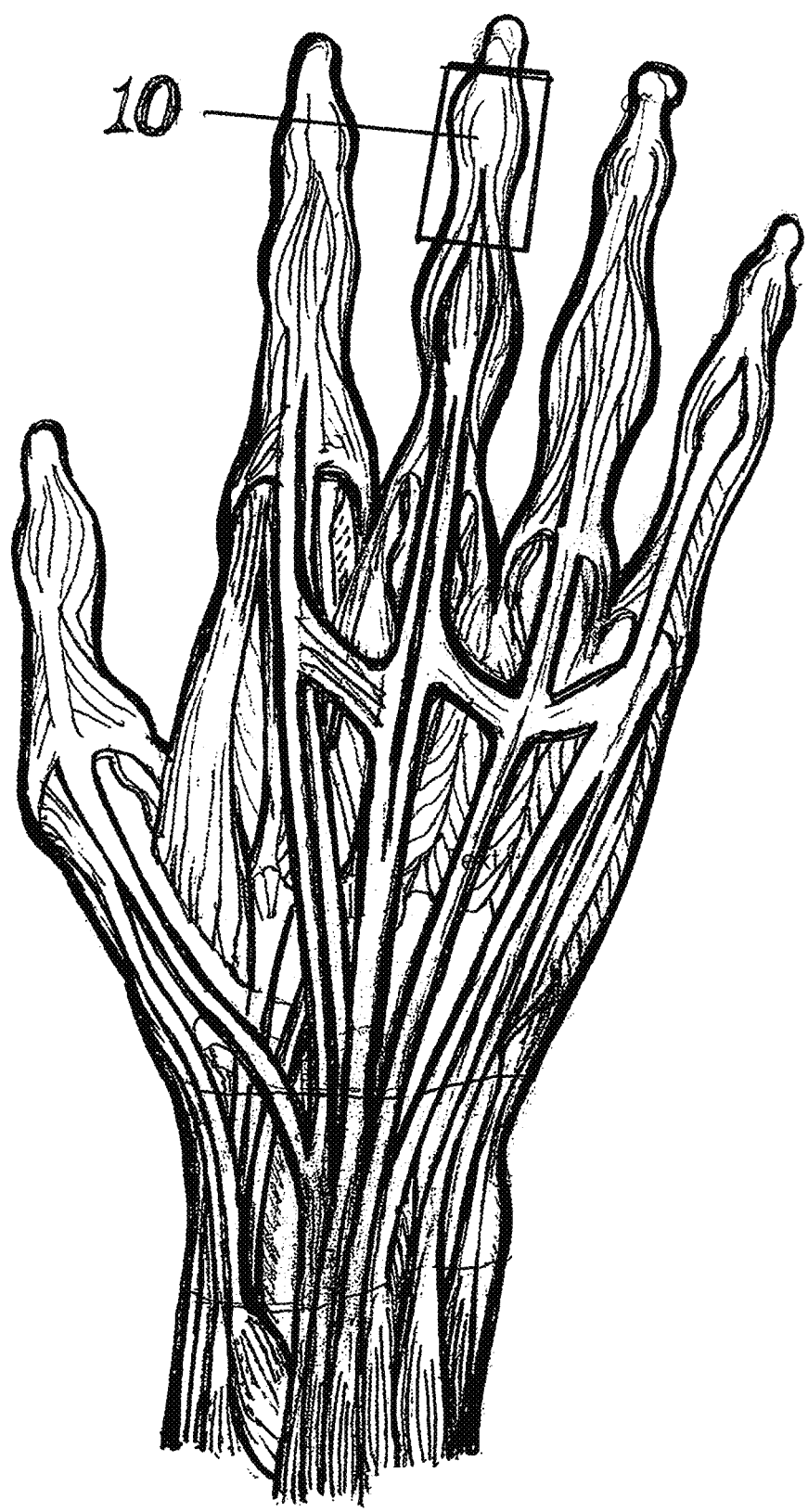
FIG. 2. is a drawing of the application of dynamic adhesive medical tape 10 applied distally to proximally with tension for the elicitation of extension of the distal interphalangeal joint 3. The location of the tape 10 is under the proximal nail bed 2 across the distal interphalangeal joint 3, capturing part of the extensor digitorum tendon 6 that is located underneath the joint capsule, and not exposed in this portion of the drawing.
Figure 3:
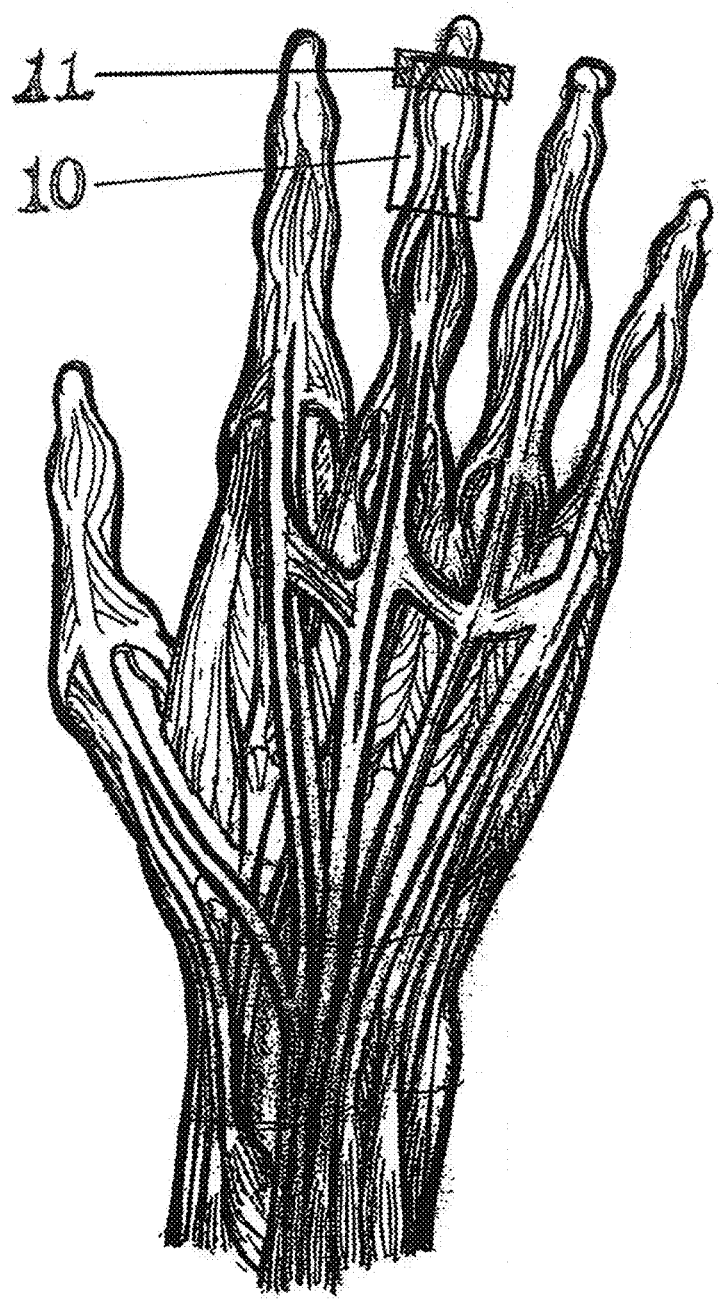
FIG. 3. is a drawing of the application of static adhesive medical tape 11 to anchor the distal region of dynamic adhesive medical tape 10.
Figure 4:
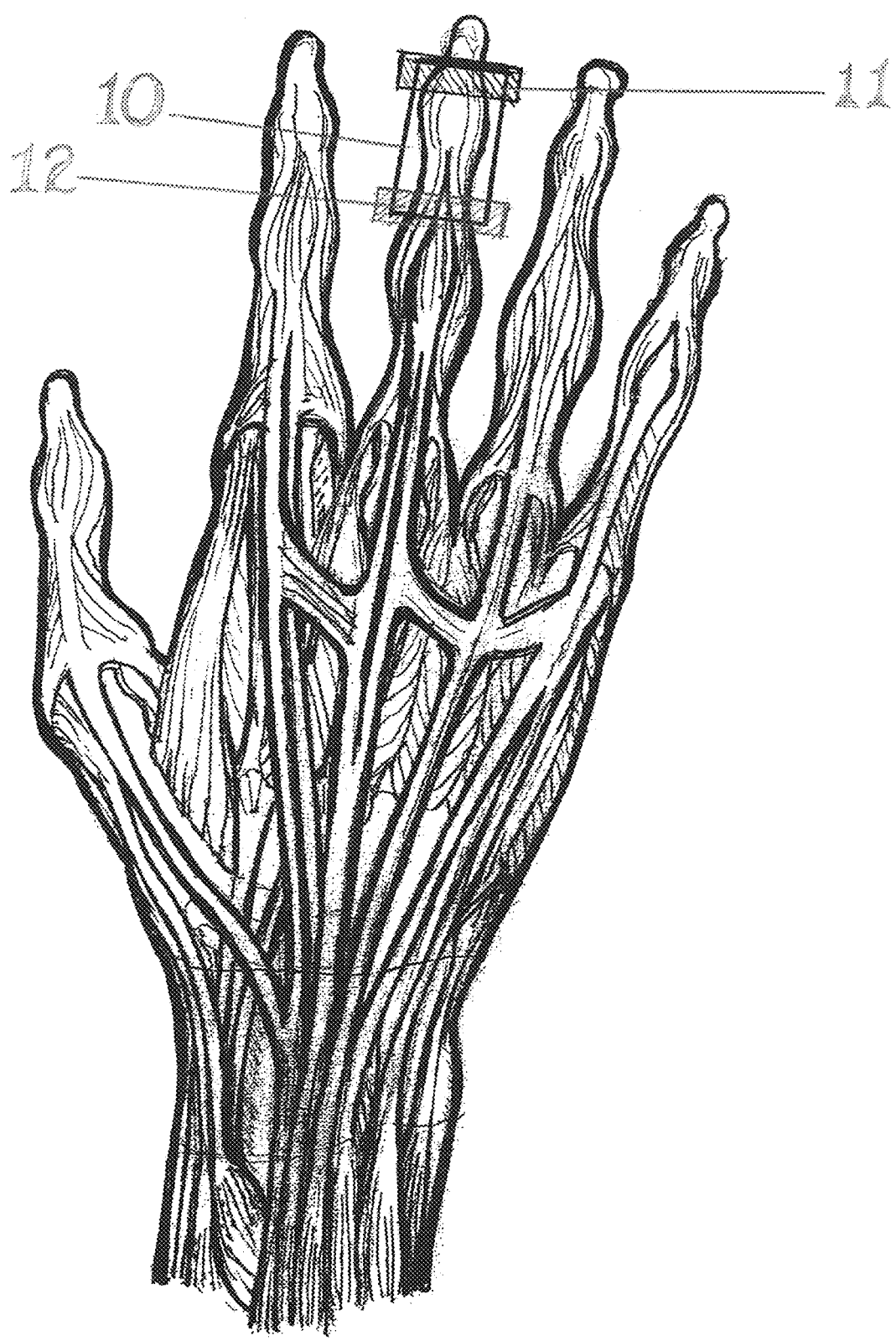
FIG. 4. is a drawing of the application of static adhesive medical tape 12 to anchor the proximal region of dynamic adhesive medical tape 10.
Figure 5:
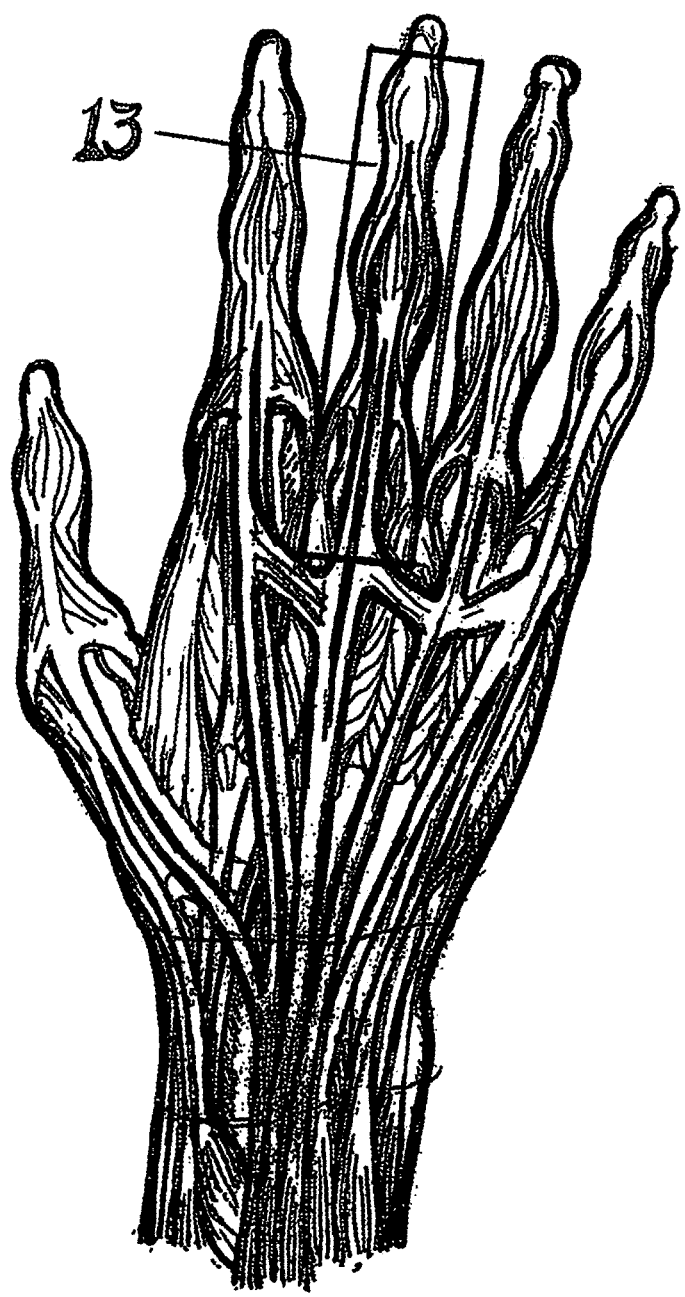
FIG. 5. is a drawing of the application of dynamic adhesive medical tape 13 applied distally to proximally with tension for the elicitation of extension of the distal interphalangeal joint 3, the proximal interphalangeal joint 4, and the metacarpophalangeal joint 5.
Figure 6:
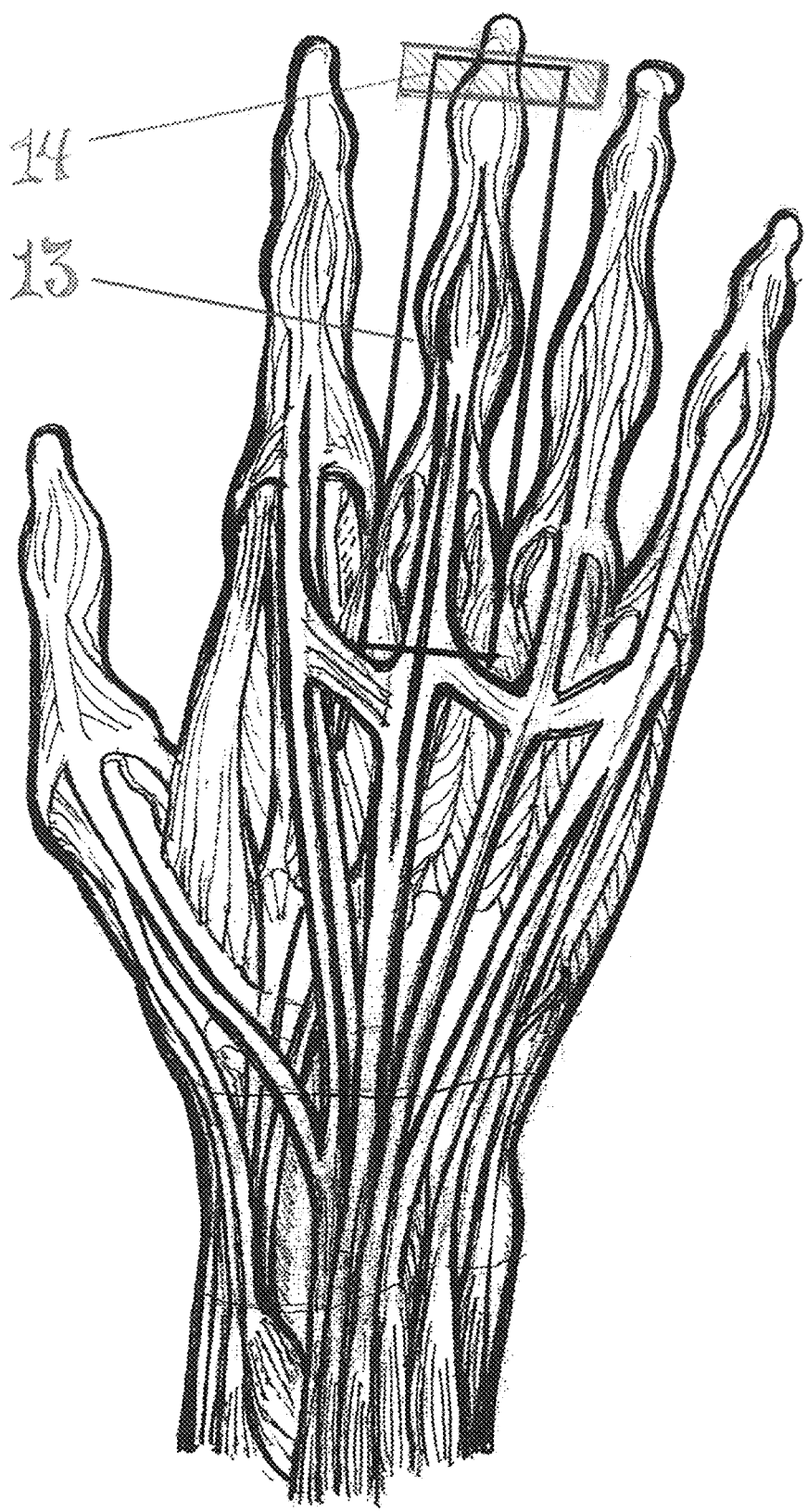
FIG. 6. is a drawing of the application of static adhesive medical tape 14 to anchor the distal region of dynamic adhesive medical tape 13.
Figure 7:
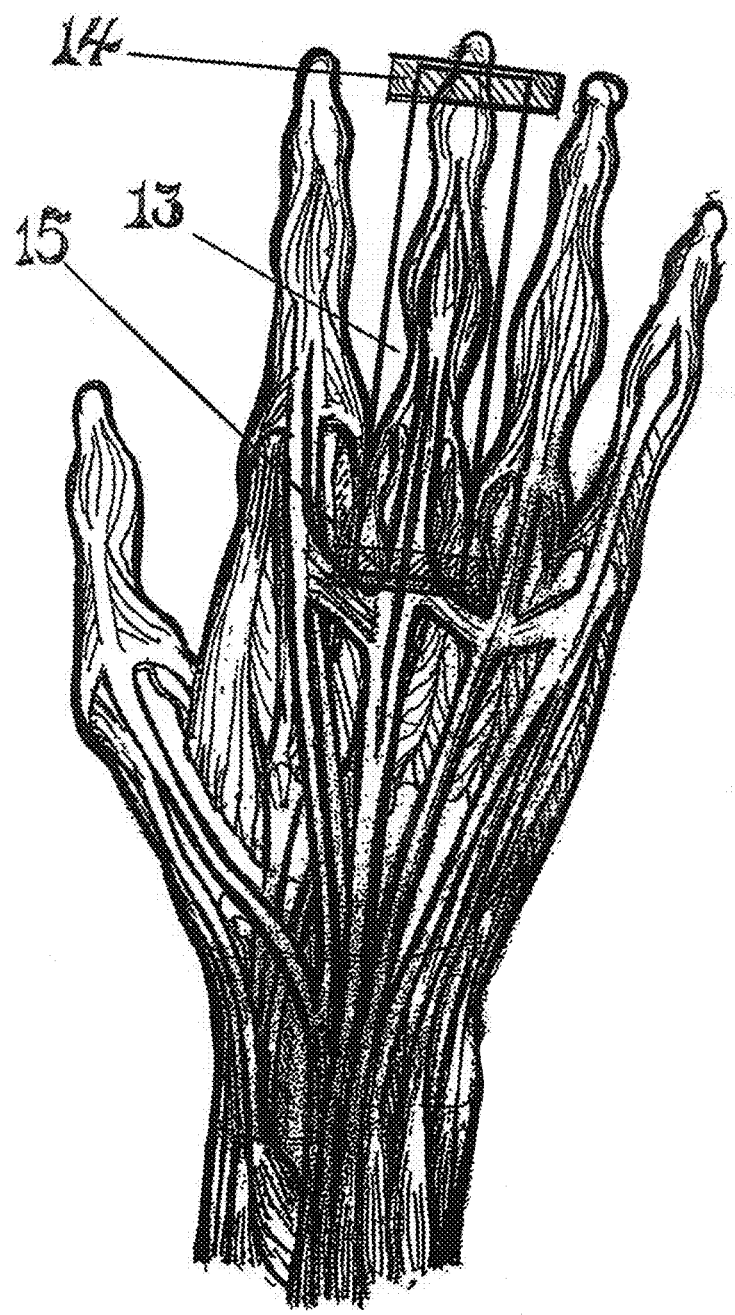
FIG. 7. is a drawing of the application of static adhesive medical tape 15 to anchor the proximal region of dynamic adhesive medical tape 13.
Figure 8:
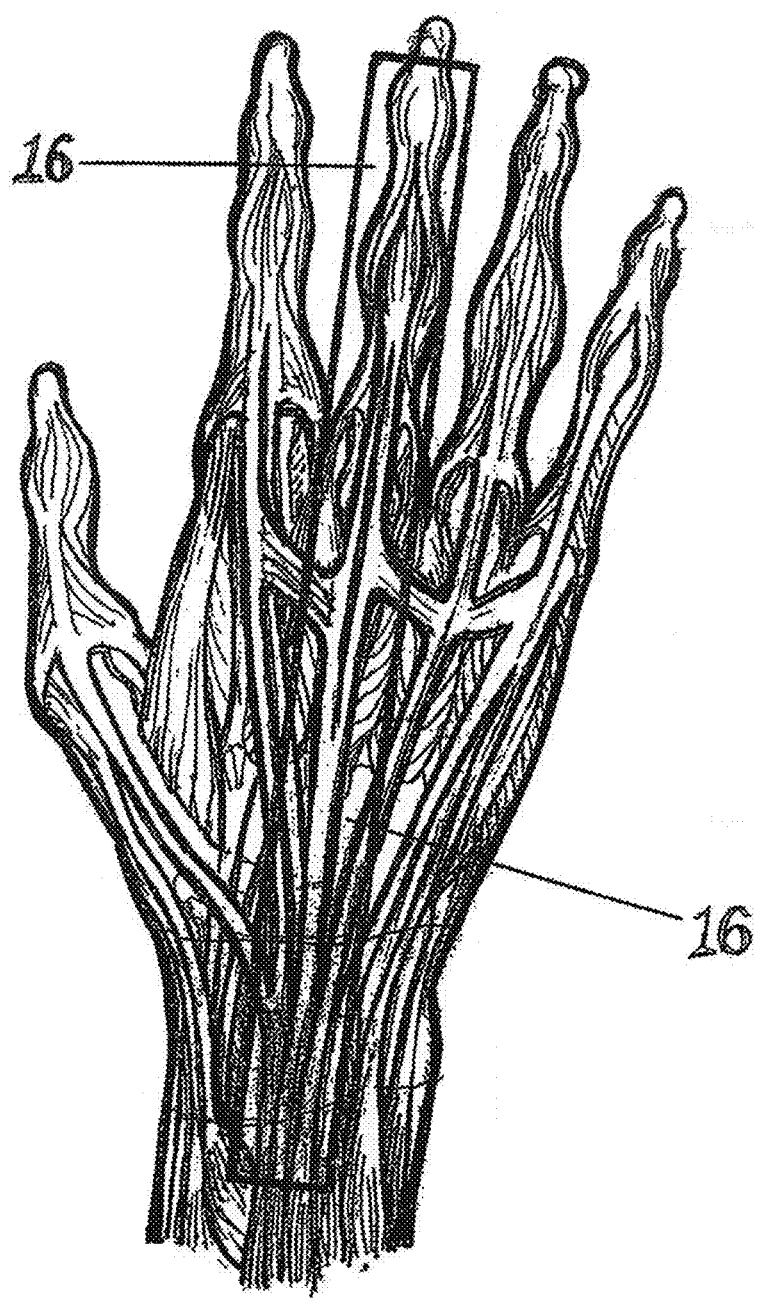
FIG. 8. is a drawing of the application of dynamic adhesive medical tape 16 applied distally to proximally with tension for the elicitation of extension of the distal interphalangeal joint 3, the proximal interphalangeal joint 4, and the metacarpophalangeal joint 5. The tape 16 goes into the myotendinous region of the extensor digitorum muscle distal region in alignment with the 3d digit 8.
Figure 9:
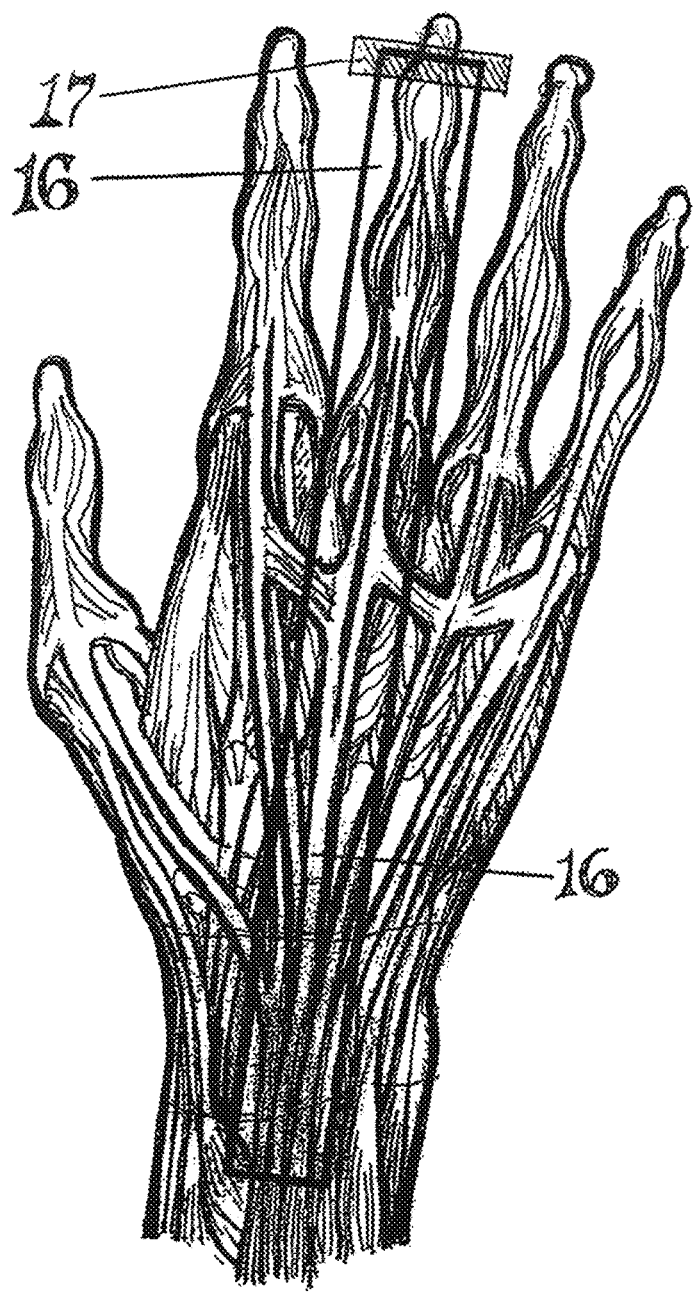
FIG. 9. is a drawing of the application of static adhesive medical tape 17 to anchor the distal region of dynamic adhesive medical tape 16.
Figure 10:
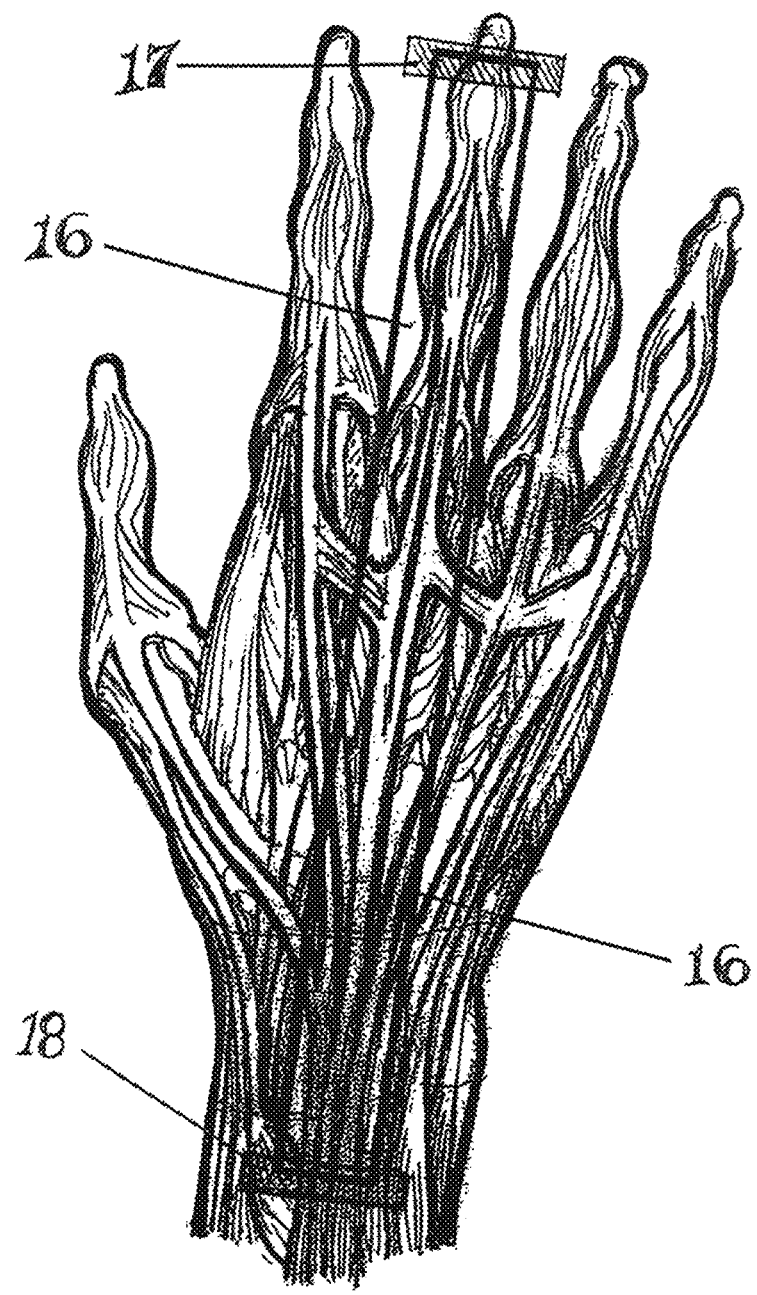
FIG. 10. is a drawing of the application of static adhesive medical tape 18 to anchor the proximal region of dynamic adhesive medical tape 16.
Figure 11:
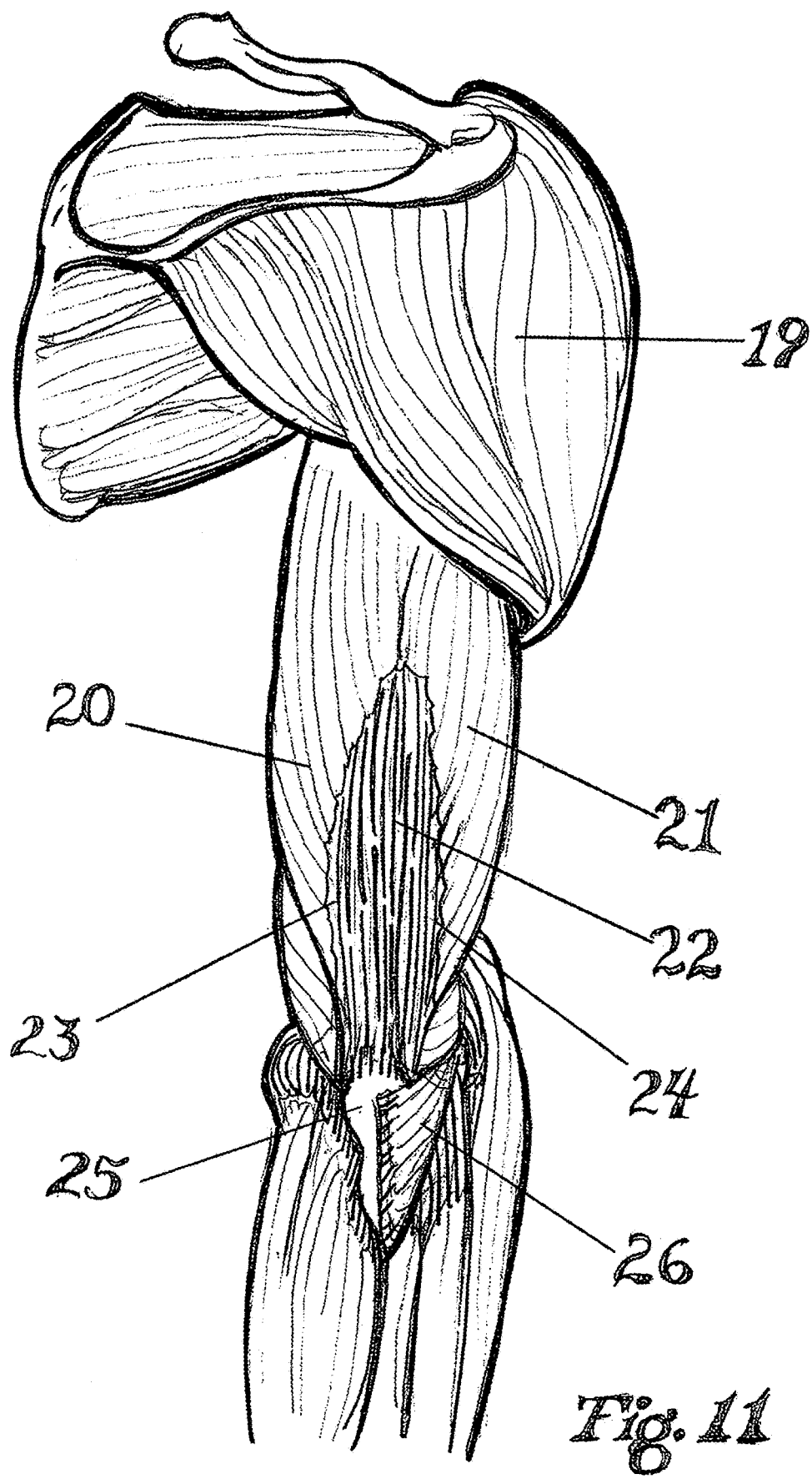
FIG. 11. is a drawing of the right shoulder and right arm anatomical features from the posterior view: deltoid muscle 19, triceps brachii, long head muscle 20, triceps brachii, lateral head 21, triceps brachii tendon 22, myotendinous region of the triceps brachii 23, 24, olecranon 25, and anconeus muscle 26.
Figure 12:
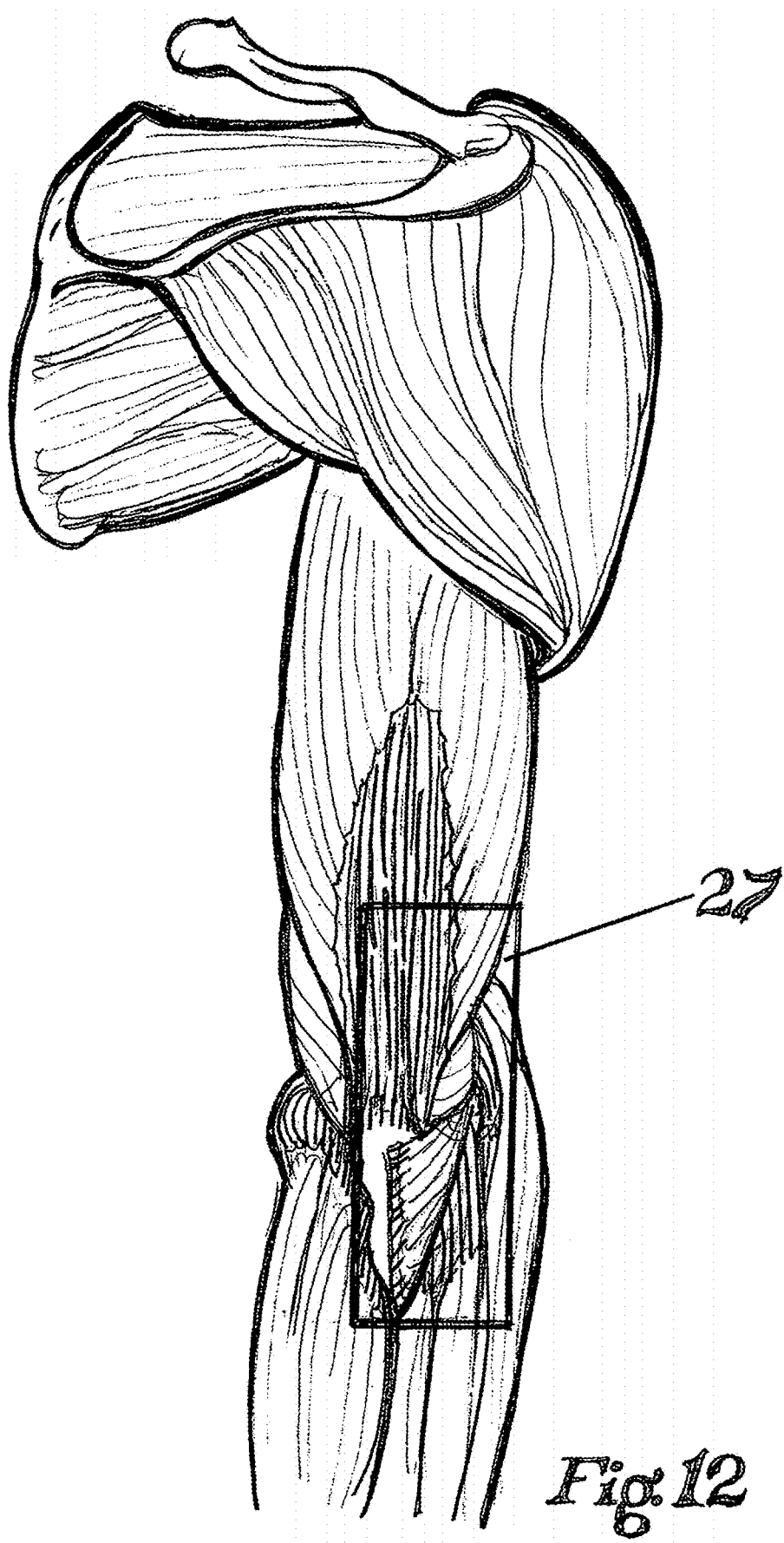
FIG. 12. is a drawing of the application of dynamic adhesive medical tape 27 applied laterally, and distally to proximally, with tension for the elicitation of extension of the elbow joint. The location of the tape is extending beyond the olecranon 25 and goes up halfway through the proximal portion of the tendon of the tricep brachii 22.
Figure 13:
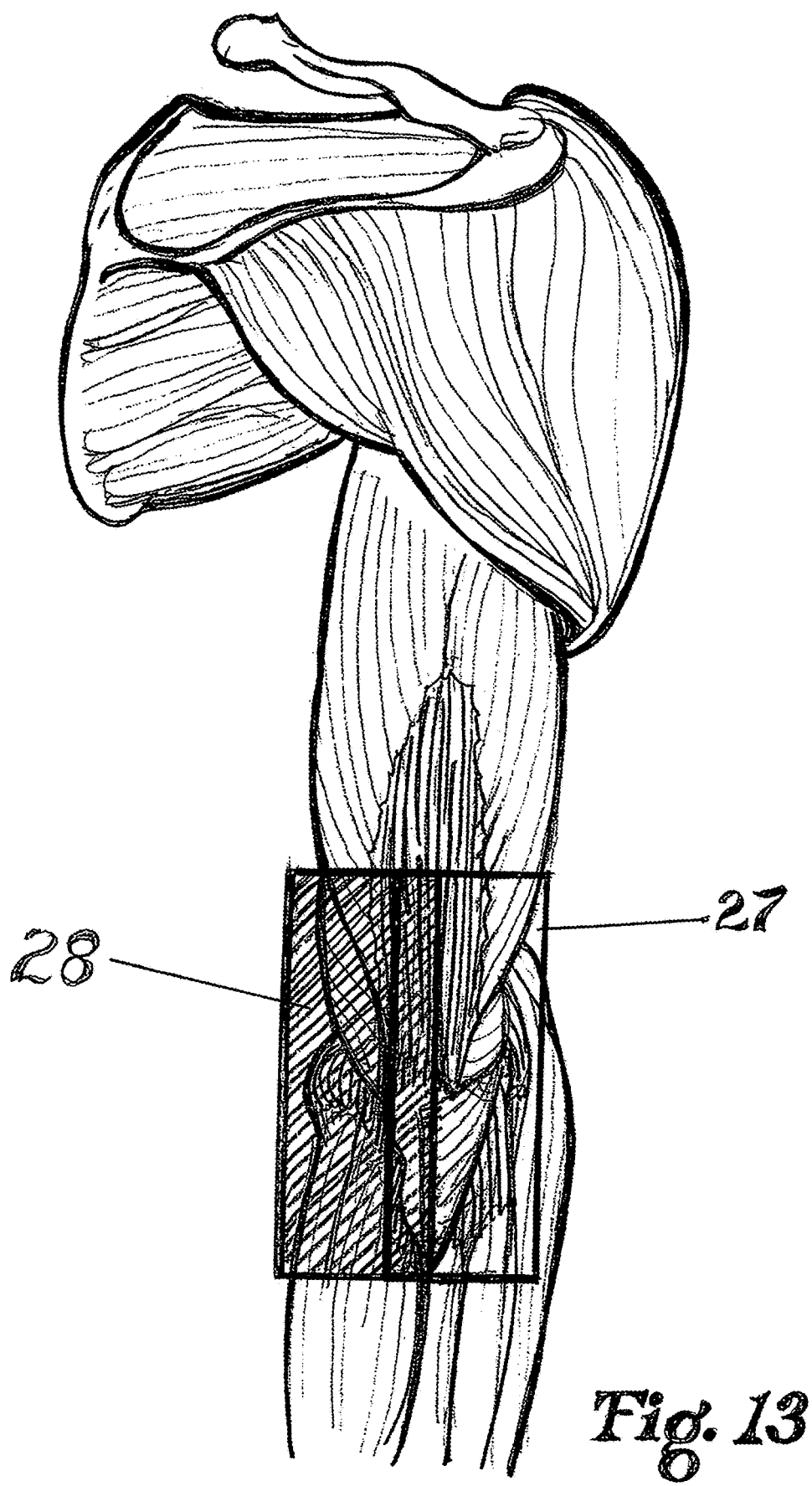
FIG. 13. is a drawing of the application of dynamic medical adhesive tape 28 applied medially, and distally to proximally, with tension for the elicitation of extension of the elbow joint. The location of the tape is extending beyond the olecranon 25 applied medially halfway through the proximal portion of the tendon of the tricep brachii 22. It is also overlapping the previous piece of tape 27 to further secure the tape.
Figure 14:
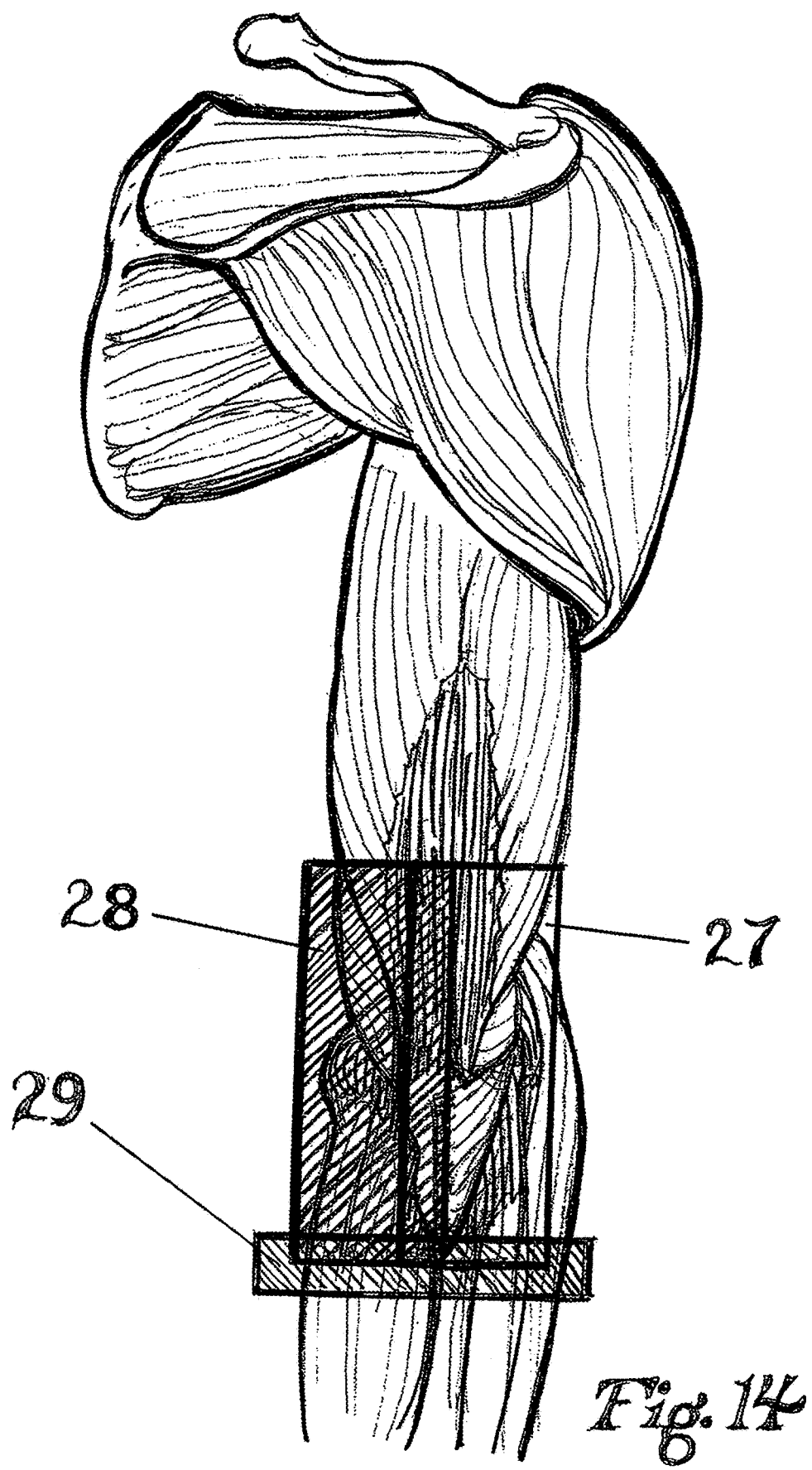
FIG. 14. is a drawing of the application of static adhesive medical tape 29 to anchor the distal region of dynamic adhesive medical tape 27, 28, encompassing both pieces of tape.
Figure 15:
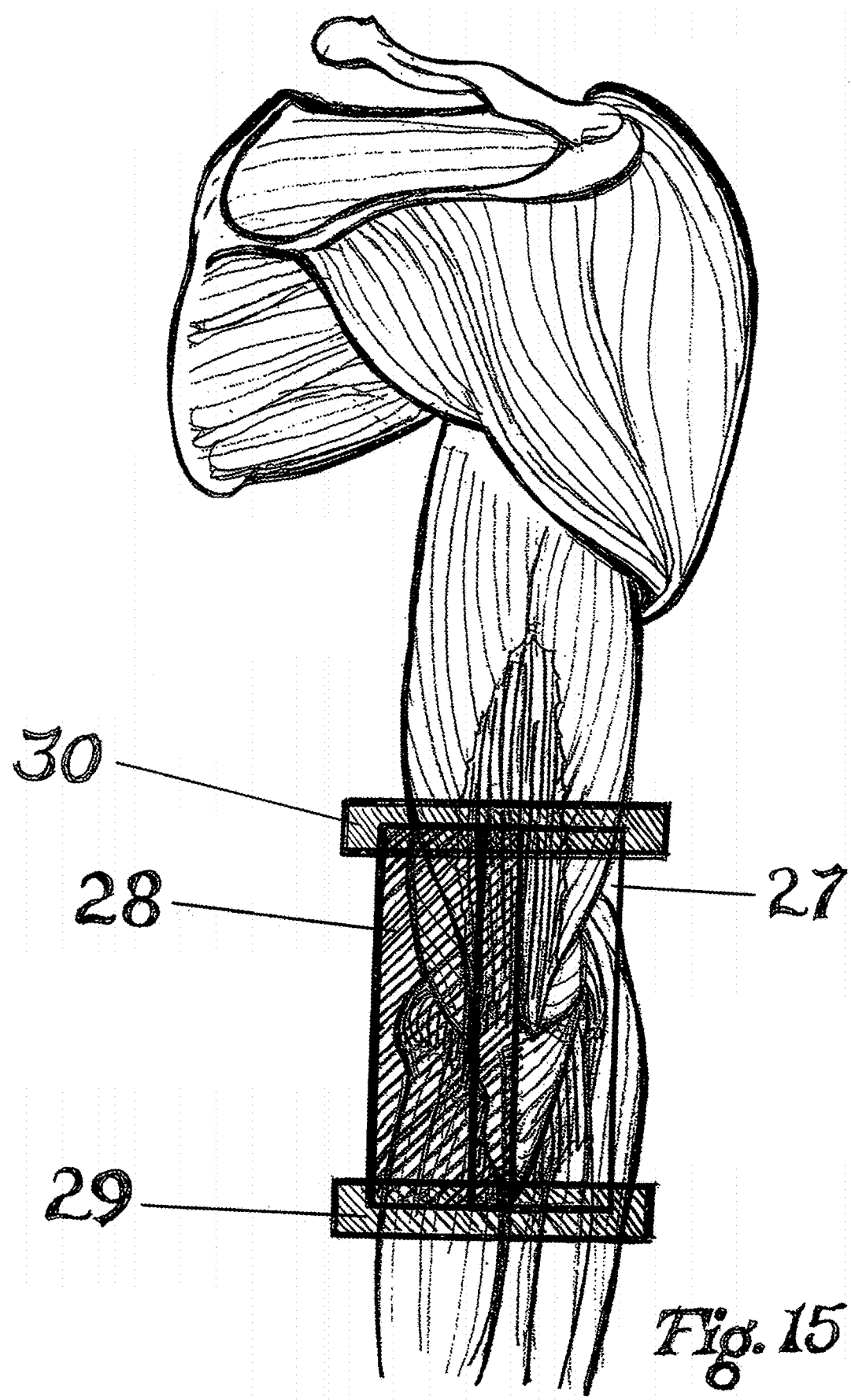
FIG. 15. is a drawing of the application of static adhesive medical tape 30 to anchor the proximal region of dynamic adhesive medical tape 27, 28, encompassing both pieces of tape.
Figure 16:
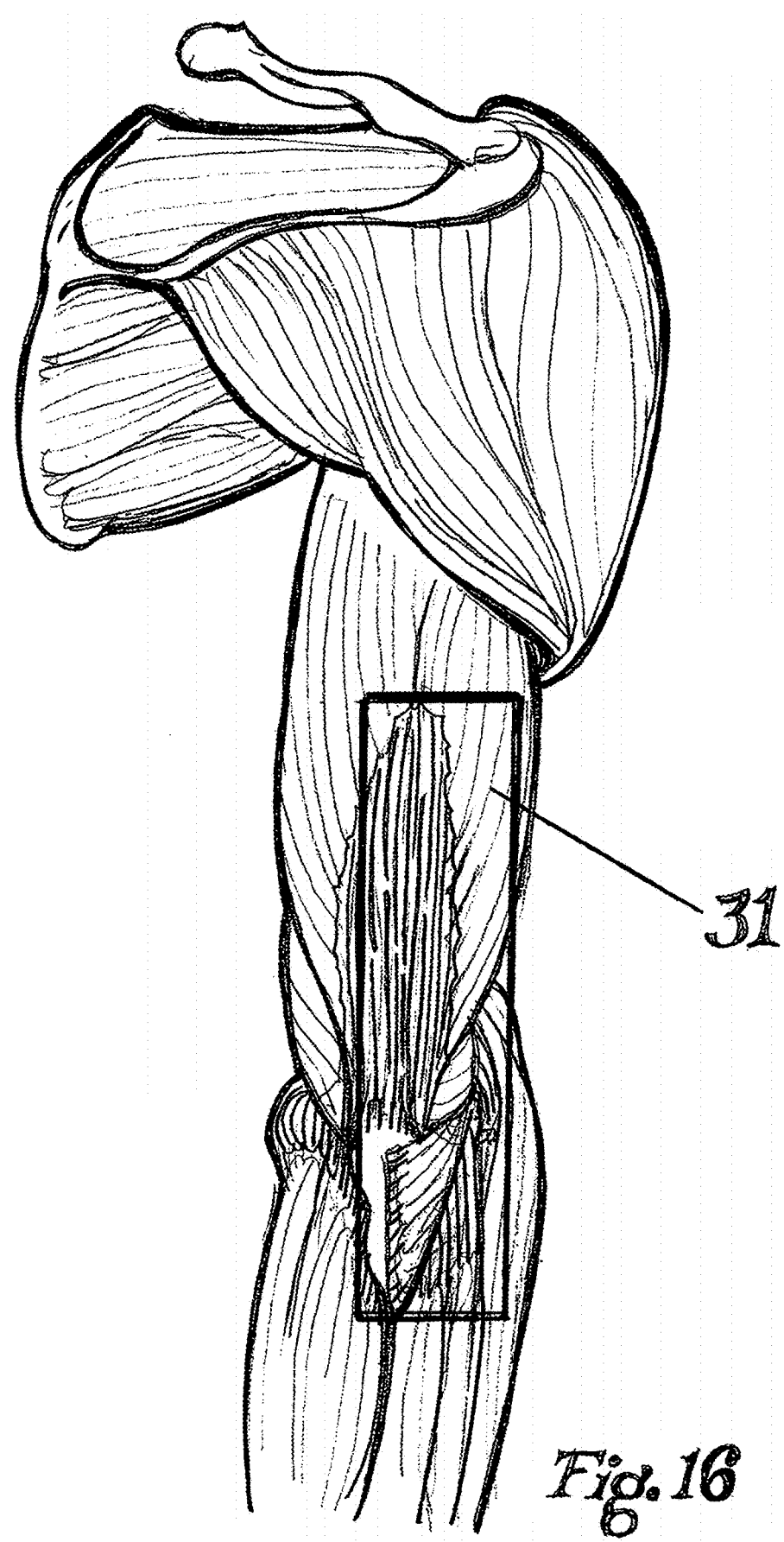
FIG. 16. is a drawing of the application of dynamic adhesive medical tape 31 applied laterally, distally to proximally, with tension for the elicitation of extension of the elbow joint. The location of the tape 31 is lateral and captures the entire length of the tendon of the tricep brachii 22.
Figure 17:
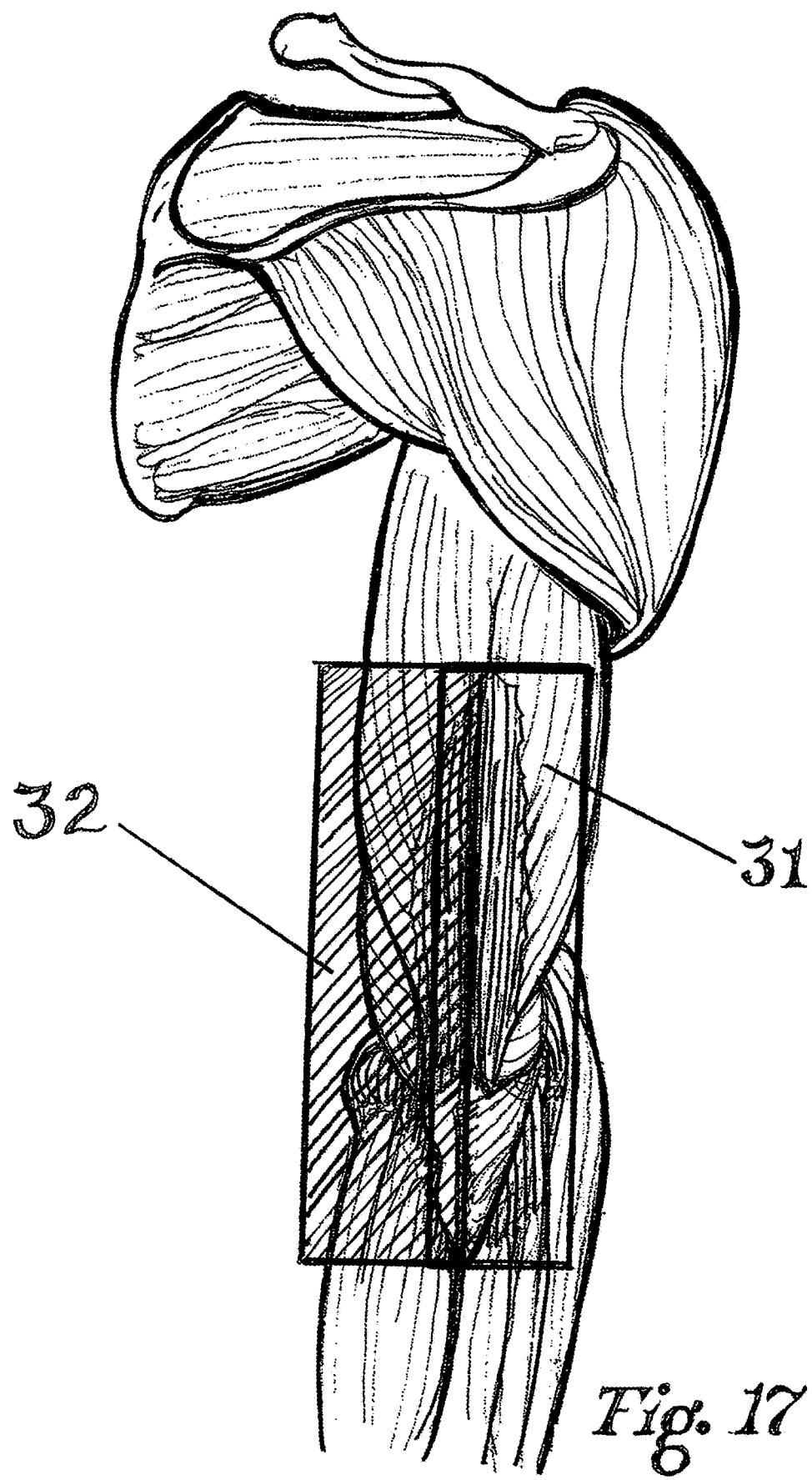
FIG. 17. is a drawing of the application of dynamic adhesive medical tape 32 applied medially, and distally to proximally, with tension for the elicitation of extension of the elbow joint. The location of the tape 32 is medial and captures the entire length of the tendon of the tricep brachii 22. It is also overlapping the previous piece of tape 31 to further secure the tape.
Figure 18:
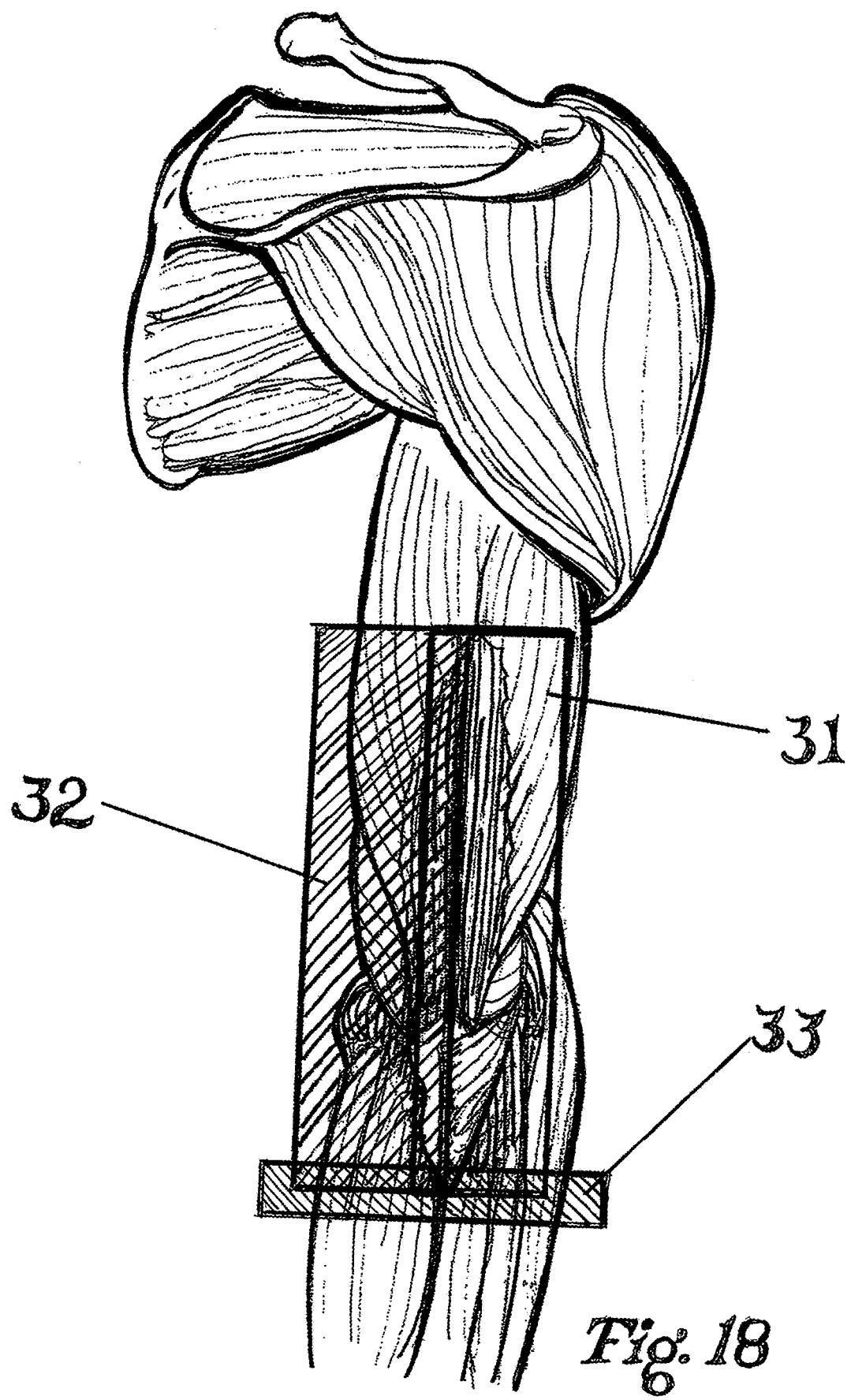
FIG. 18. is a drawing of the application of static adhesive medical tape 33 to anchor the distal region of the dynamic adhesive medical tape 31, 32, encompassing both pieces of tape.
Figure 19:
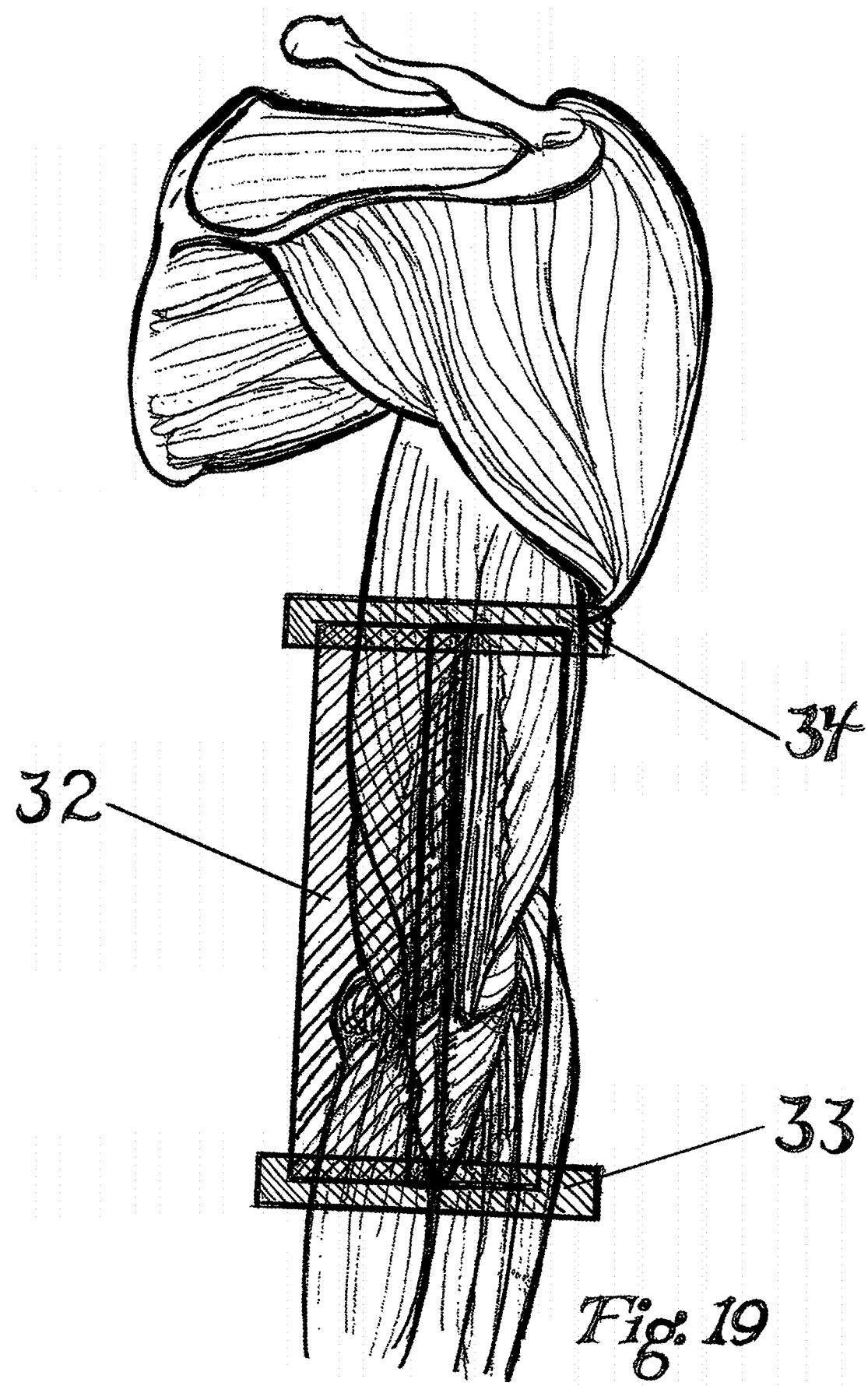
FIG. 19. is a drawing of the application of static adhesive medical tape 34 to anchor the proximal region of the dynamic adhesive medical tape 31, 32, encompassing both pieces of tape.
Figure 20:
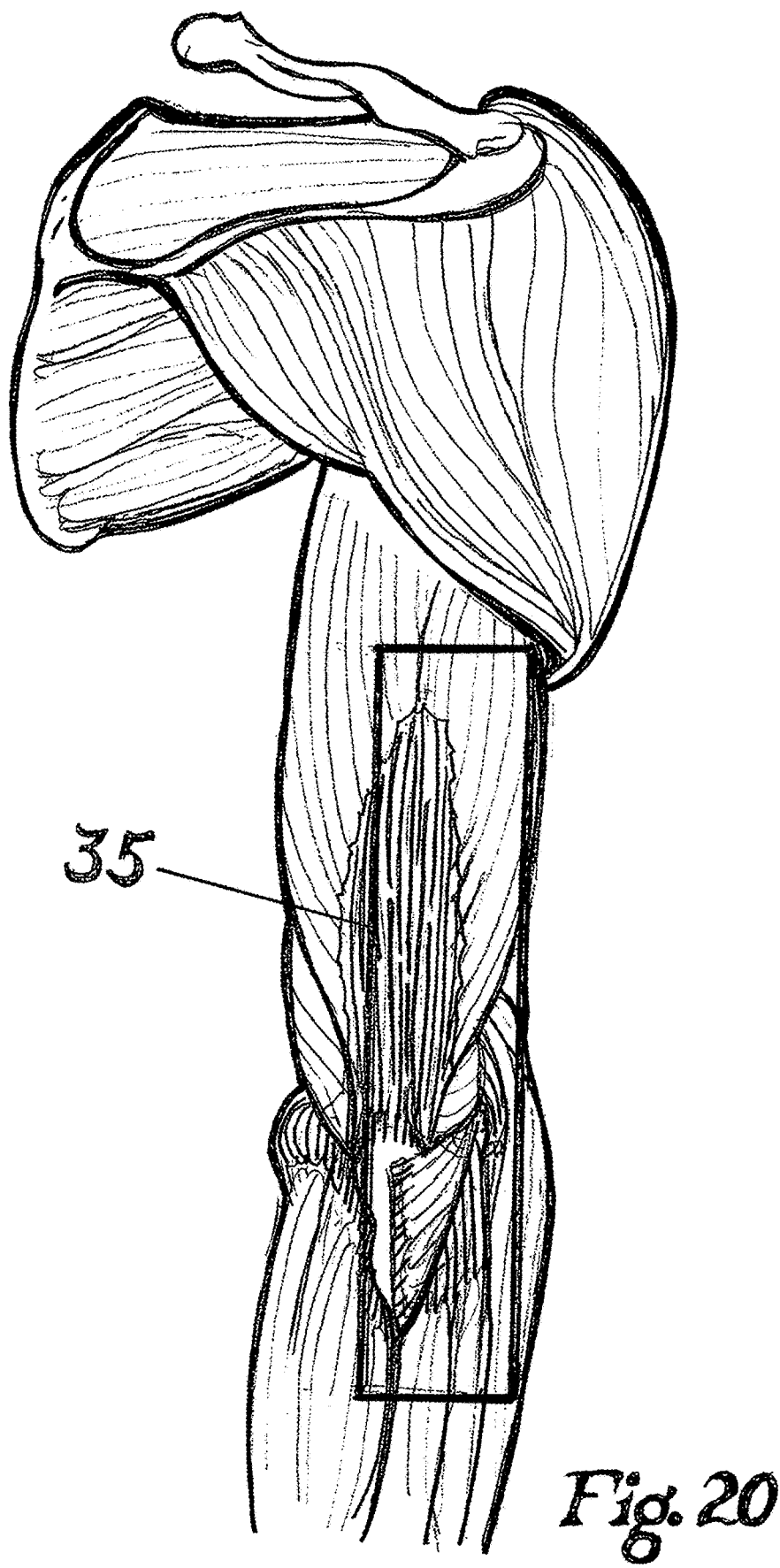
FIG. 20. is a drawing of the application of dynamic adhesive medical tape 35 applied laterally, and distally to proximally with tension for the elicitation of extension of the elbow joint. The location of the tape is lateral and captures the entire length of the tendon of the triceps brachii 22 and slightly beyond both distally and proximally.
Figure 21:
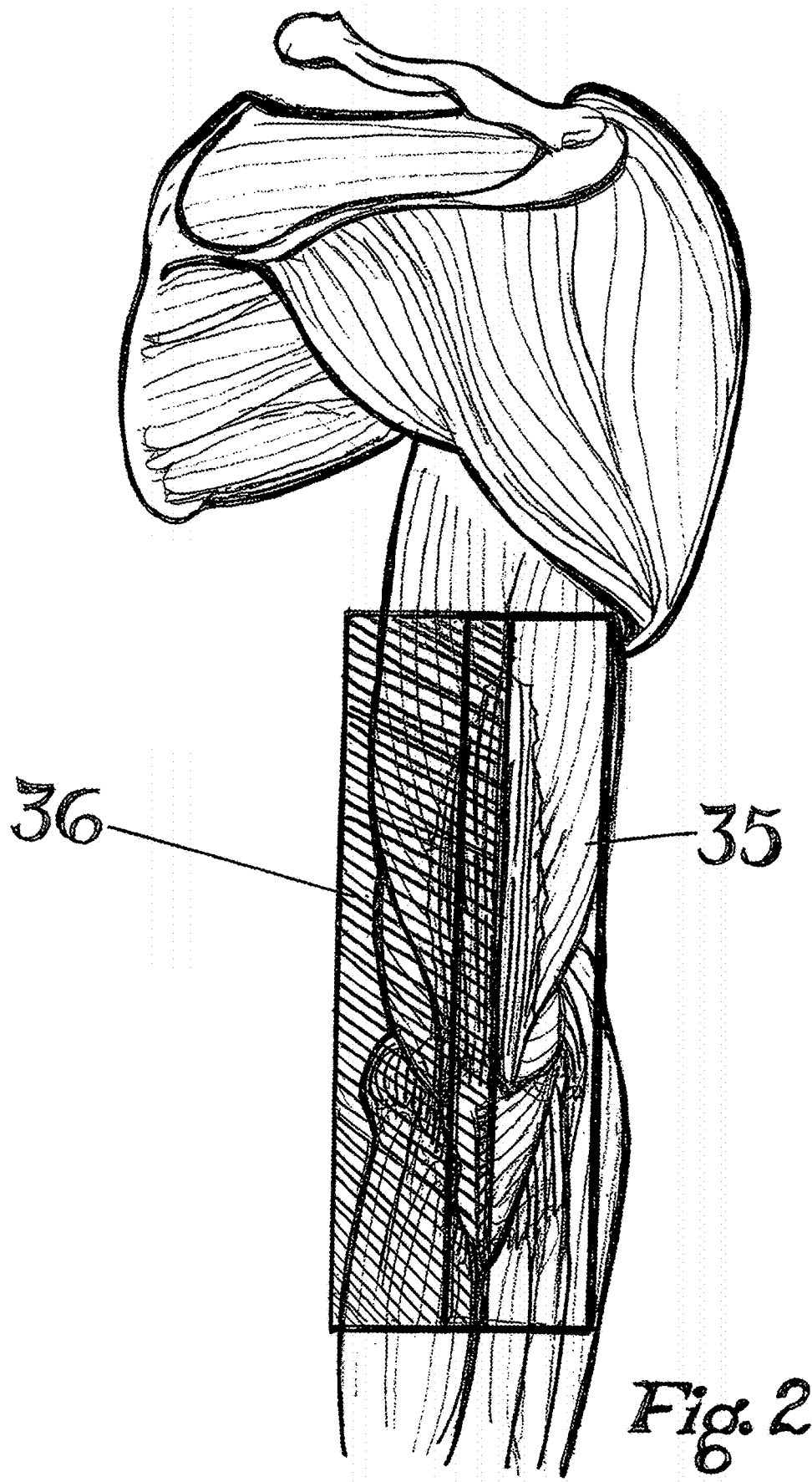
FIG. 21. is a drawing of the application of dynamic adhesive medical tape 36 applied medially, and distally to proximally with tension for the elicitation of extension of the elbow joint. The location of the tape 36 is medial and captures the entire length of the tendon of the tricep brachii 22 and slightly beyond. It is also overlapping the previous piece of tape 35 to further secure the tape.
Figure 22:
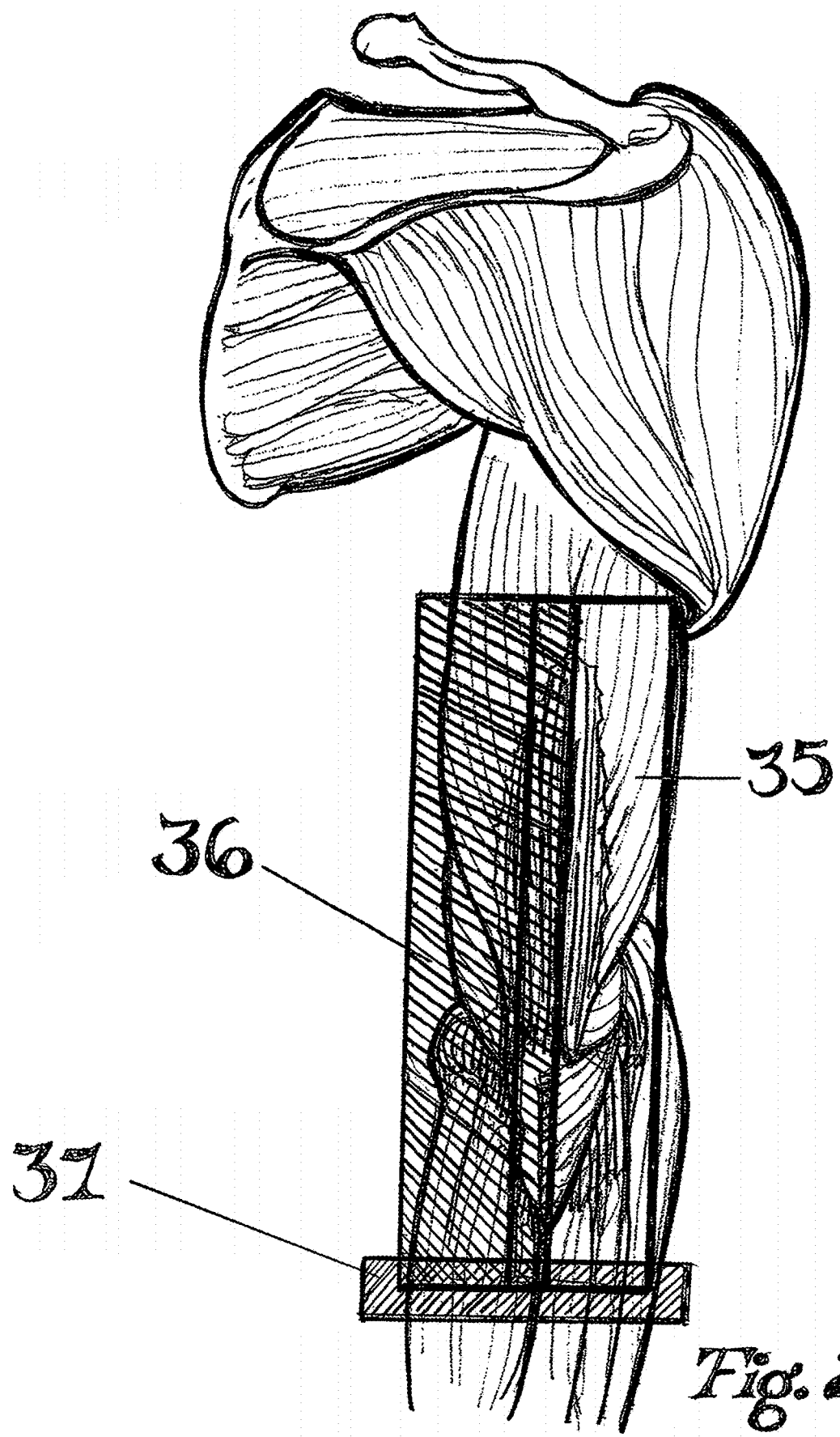
FIG. 22. is a drawing of the application of static adhesive medical tape 37 to anchor the distal region of the dynamic adhesive medical tape 35, 36 encompassing both pieces of tape 35, 36.
Figure 23:
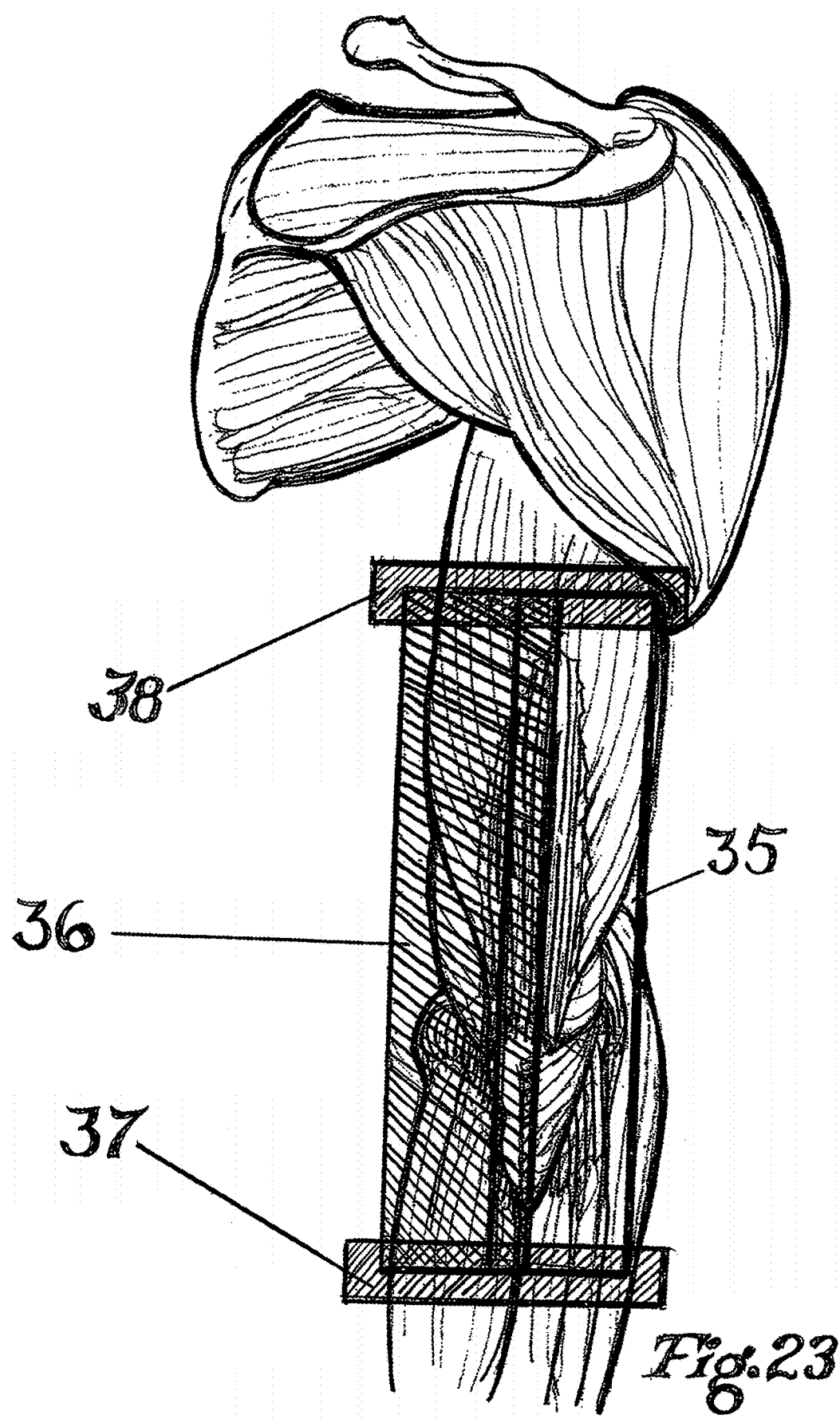
FIG. 23. is a drawing of the application of static adhesive medical tape 38 to anchor the proximal region of the dynamic adhesive medical tape 35, 36 encompassing both pieces of tape.
Figure 24:
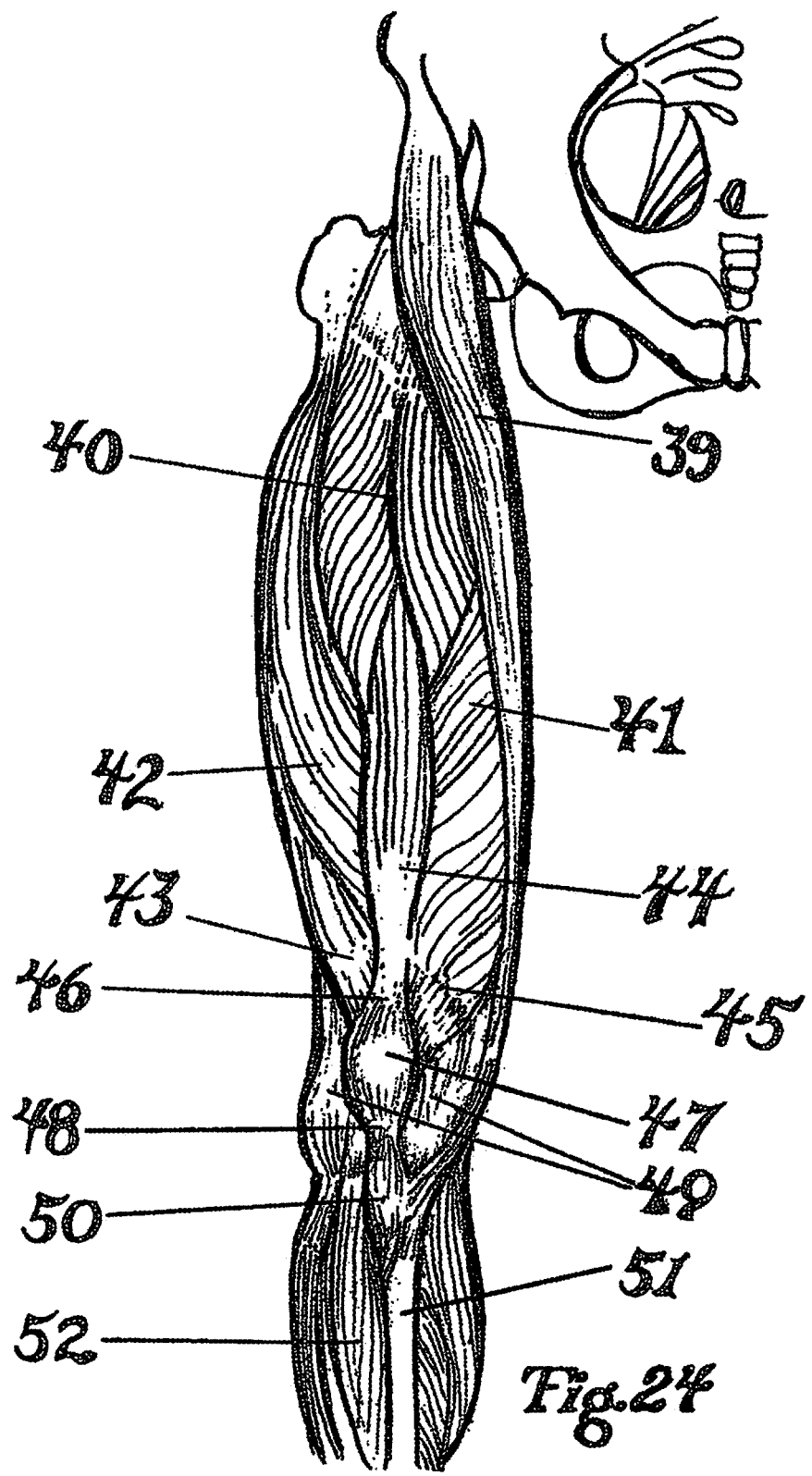
FIG. 24. is a drawing of the right quadriceps femoris and sartorius muscle, with the tensor fascia lata removed, and proximal portion of the leg, anatomical structures: sartorius 39, rectus femoris 40, vastus medialis 41, vastus lateralis 42, myotendinous junction of vastus lateralis 43, myotendinous junction of rectus femoris 44, myotendinous junction of vastus medialis 45, tendon of insertion of quadriceps 46, patella 47, patellar retinaculum 49, patellar ligament 48, tibial tuberosity 50, tibia 51, tibialis anterior 52.
Figure 25:
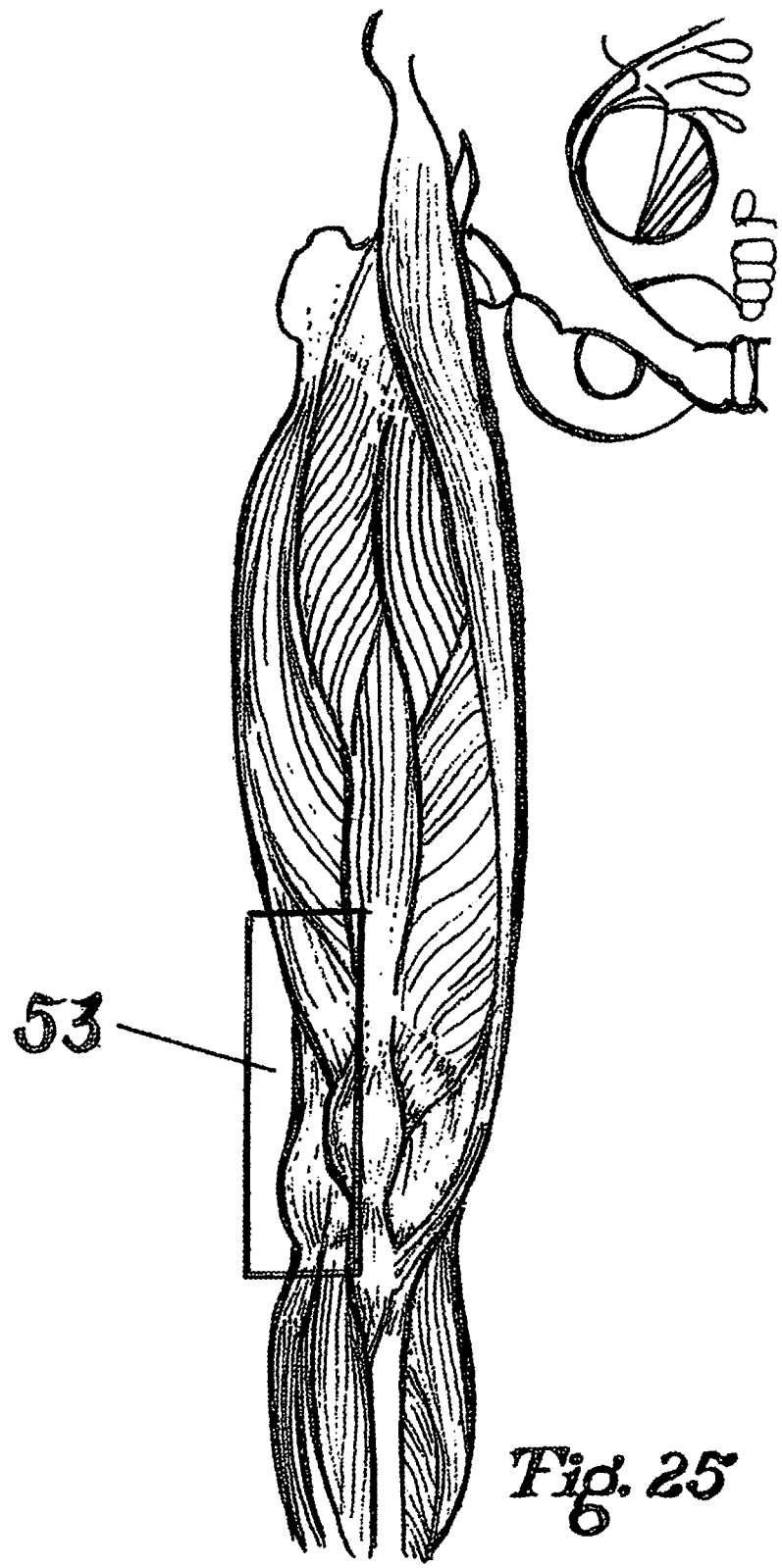
FIG. 25. is a drawing of the application of dynamic adhesive medical tape 53 applied laterally, distally to proximally, with tension for the elicitation of extension of the knee joint. The participant is positioned in a partially flexed position at their knee joint (when the tape 53 is applied). The location of the tape is at the edge of the tibial tuberosity 50 to the entire length of the patellar ligament 48 across the tendon of the quadriceps femoris, and into the edge of the myotendinous junction of the rectus femoris 44.
Figure 26:
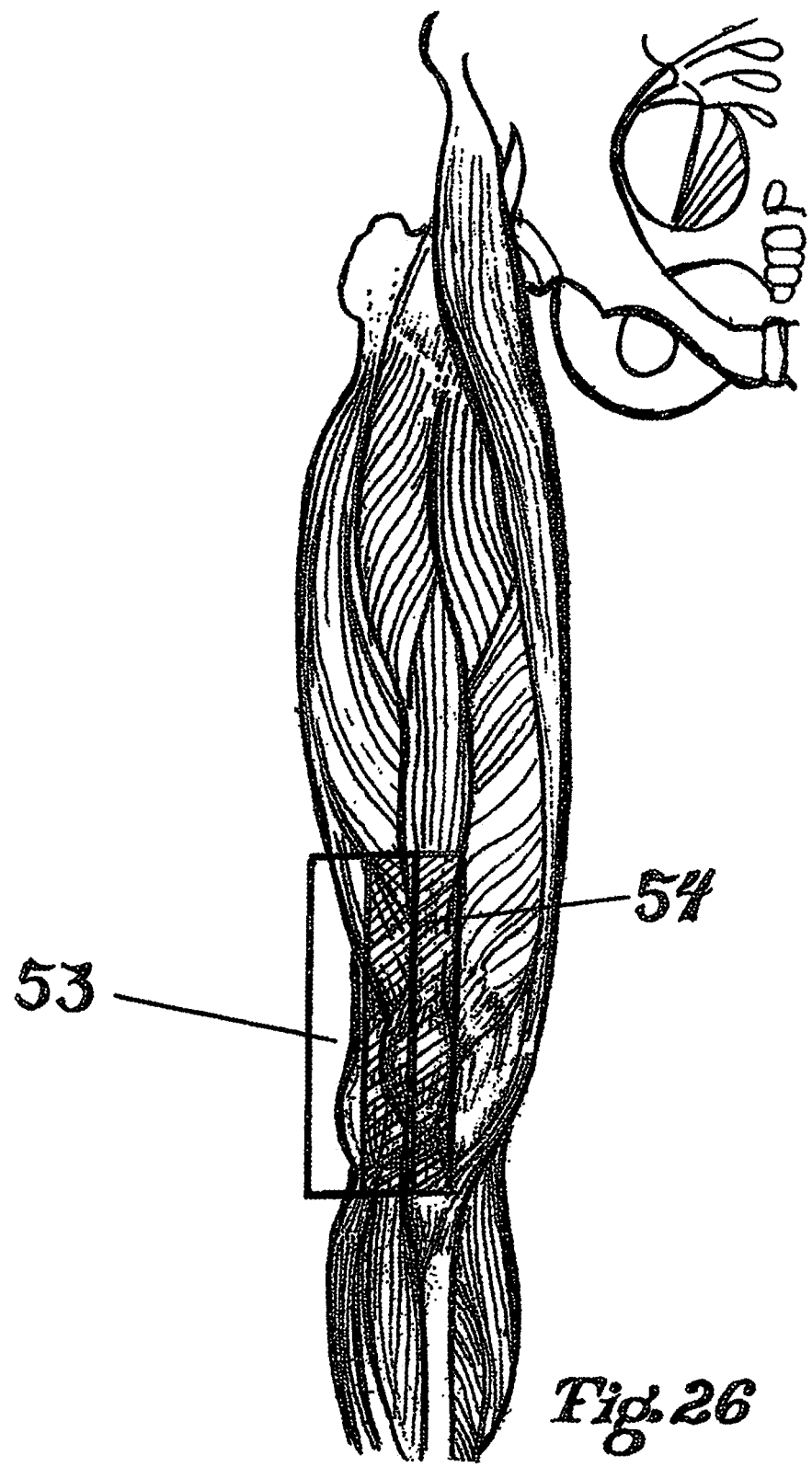
FIG. 26. is a drawing of the application of dynamic adhesive medical tape 54 applied medially to the first piece of tape 53 and distally to proximally with tension for the elicitation of extension of the knee joint. The participant is positioned in a partially flexed position at their knee joint (when the tape 54 is applied). The location of the second piece of tape 54 is at the tibial tuberosity 50 to the entire length of the patellar ligament across the tendon of the quadriceps femoris and into the myotendinous junction of the rectus femoris 44. It is also overlapping the previous piece of tape 53 to further secure the tape.
Figure 27:
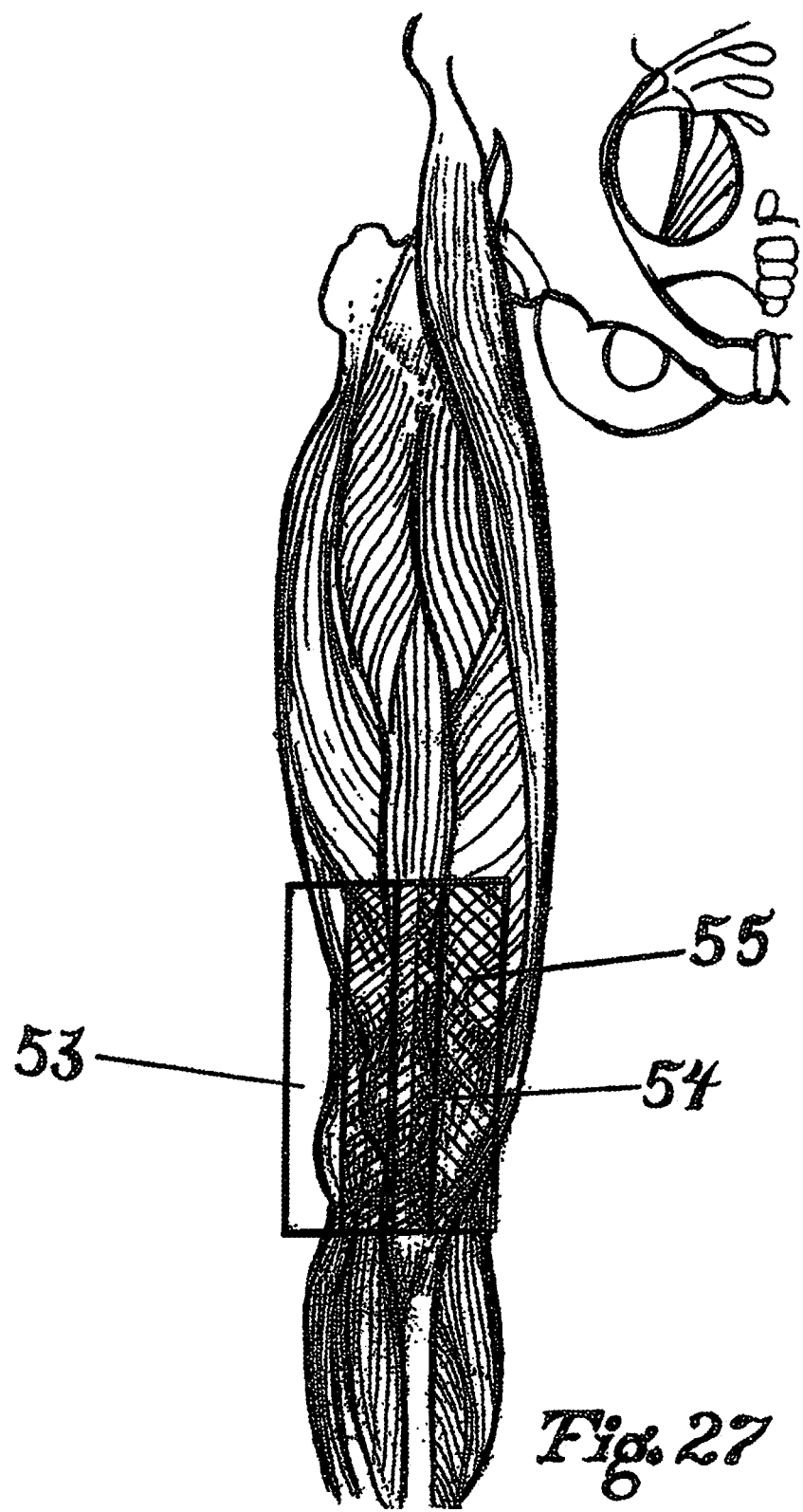
FIG. 27. is a drawing of the application of dynamic adhesive medical tape 55 applied medially to the second piece of tape 54 and distally to proximally with tension for the elicitation of extension of the knee joint. The participant is positioned in a partially flexed position at their knee joint (when the tape 55 is applied). The location of the third piece of tape 55 is at the tibial tuberosity 50 to the entire length of the patellar ligament across the tendon of the quadriceps femoris and into the myotendinous junction of the quadriceps femoris. It is also overlapping the previous piece of tape 54 to further secure the tape 54.
Figure 28:
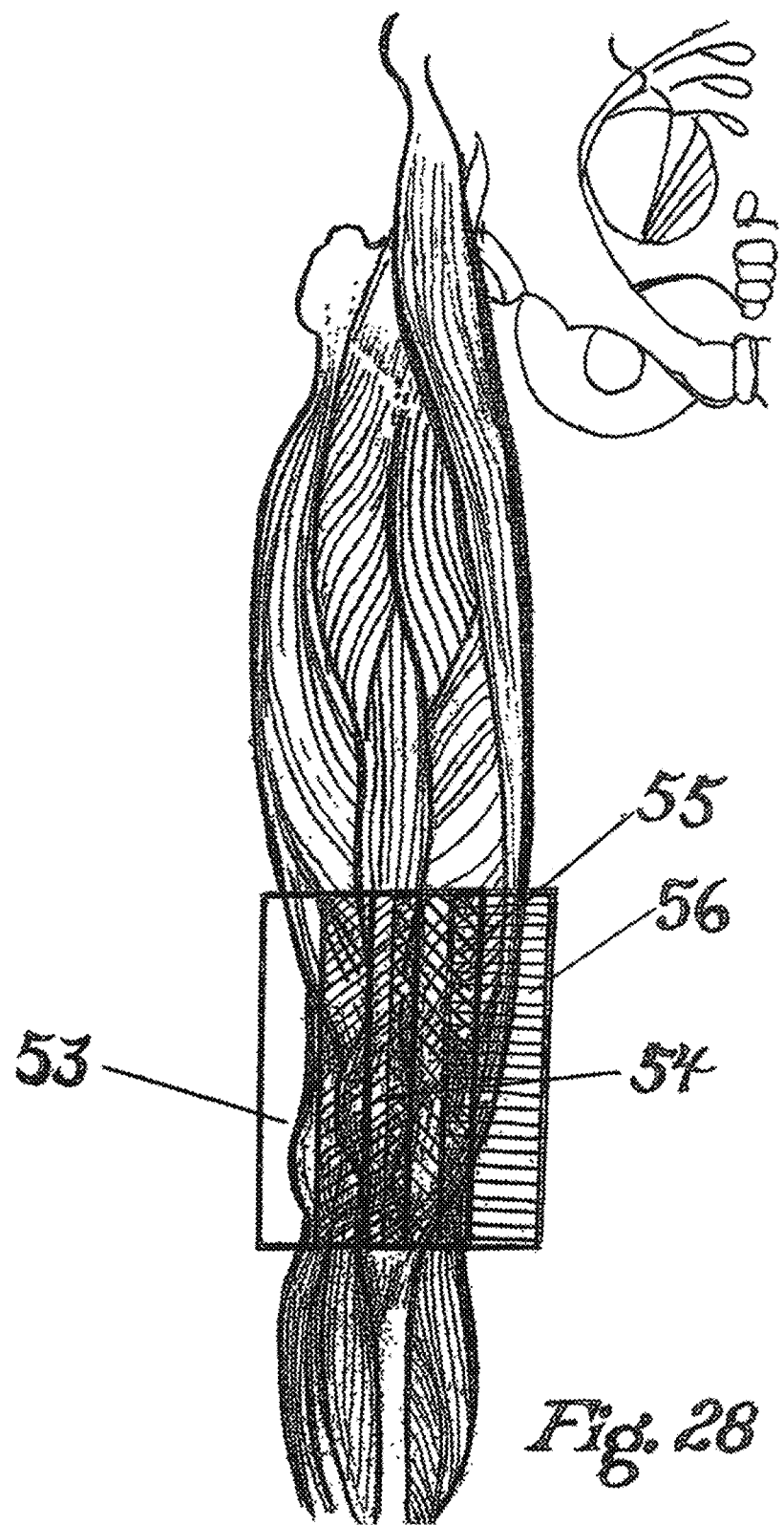
FIG. 28. is a drawing of the application of dynamic adhesive medical tape 56 applied distal to proximal with tension for the elicitation of extension of the knee joint. The location of the tape 56 is in alignment of the other pieces 53, 54, 55 crossing over the knee joint. The location of the fourth piece of tape 56 is applied medially in relation to the third piece of tape 55 with some overlap to secure the tape 55.
Figure 29:
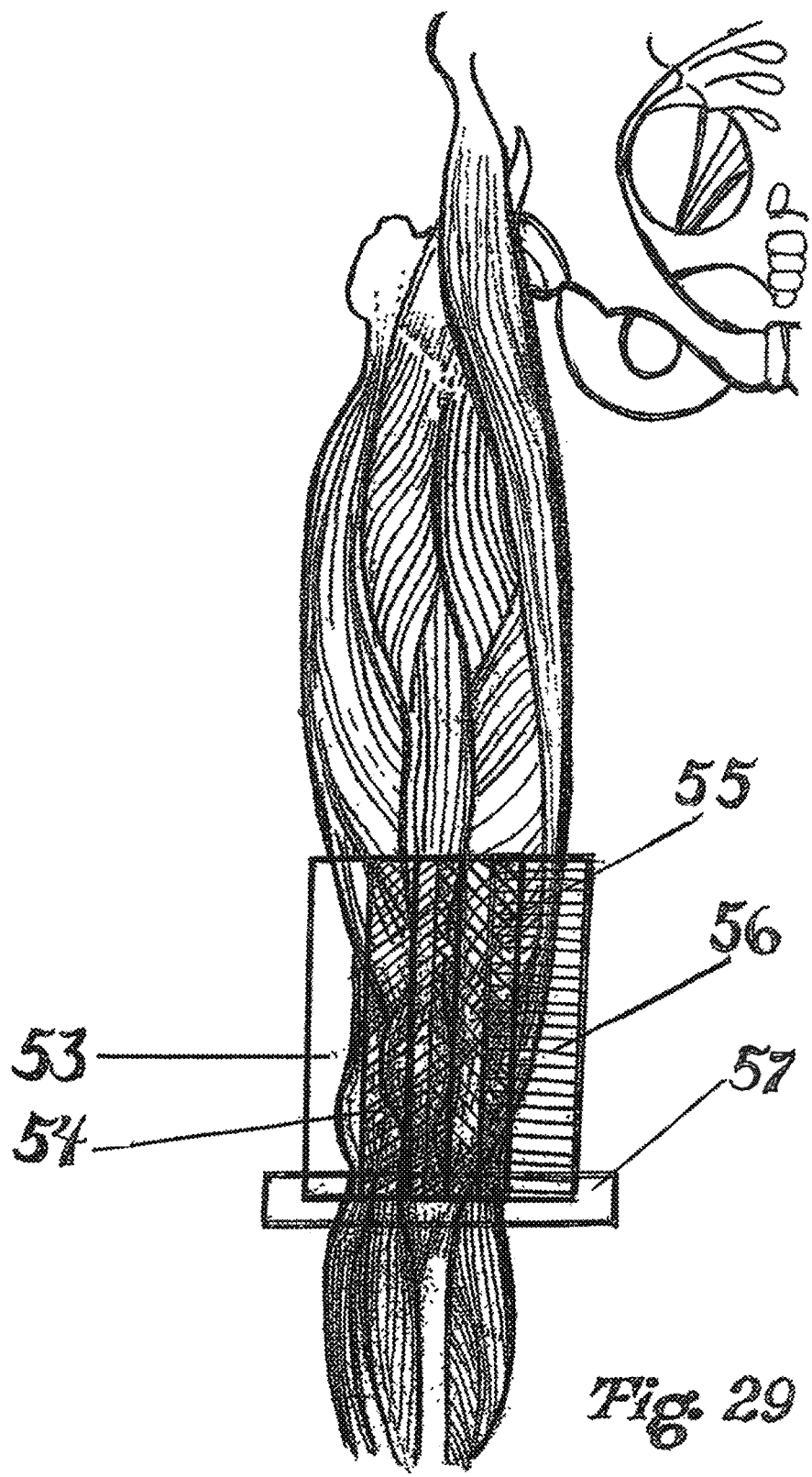
FIG. 29. is a drawing of the application of static adhesive medical tape 57 to anchor the distal region of dynamic adhesive medical tape 53, 54, 55, 56 encompassing all four pieces of tape 53, 54, 55, 56.
Figure 30:
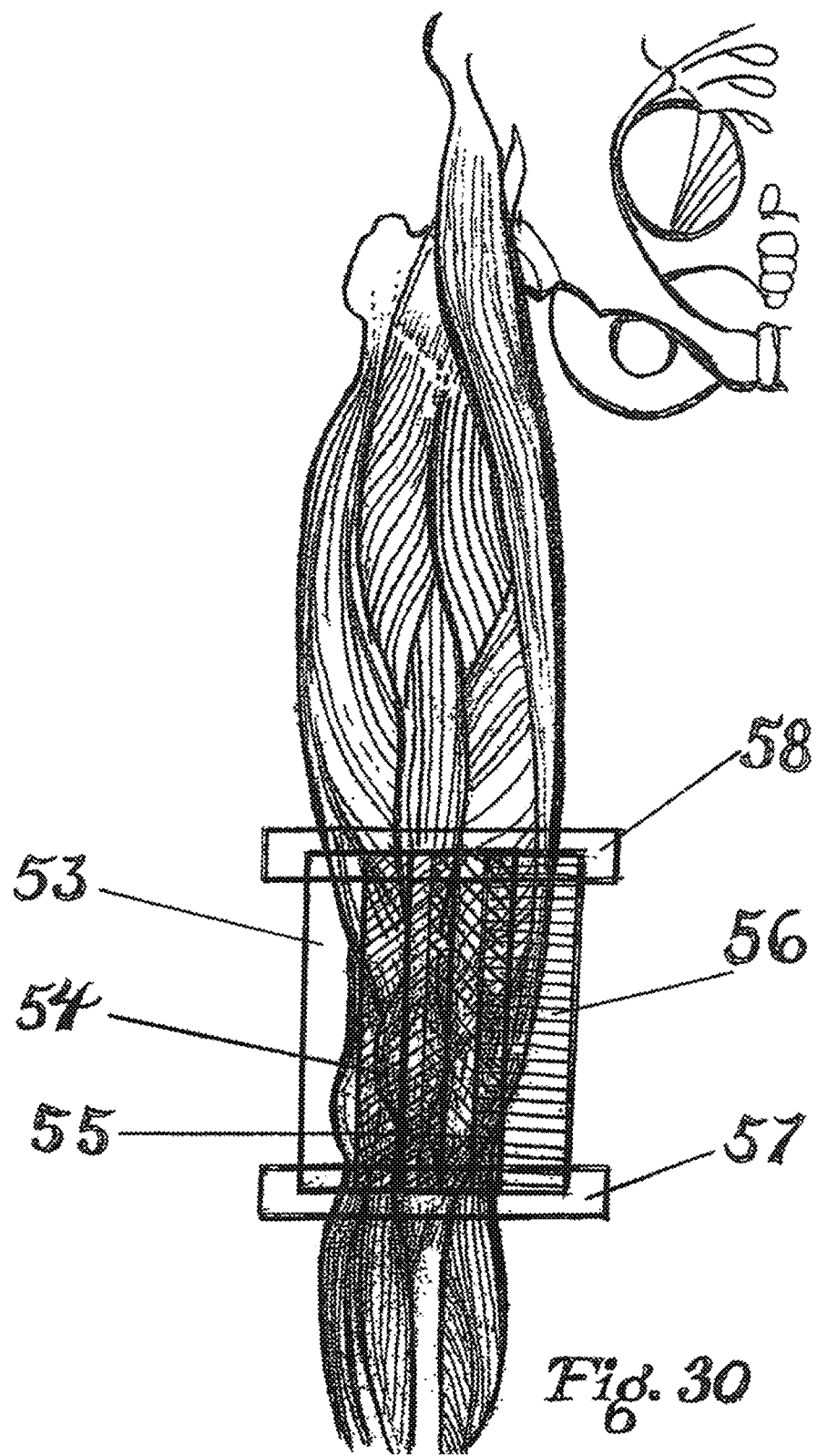
FIG. 30. is a drawing of the application of static adhesive medical tape 58 to anchor the proximal region of dynamic adhesive medical tape 53, 54, 55, 56 encompassing all four pieces of tape 53, 54, 55, 56.
Figure 31:
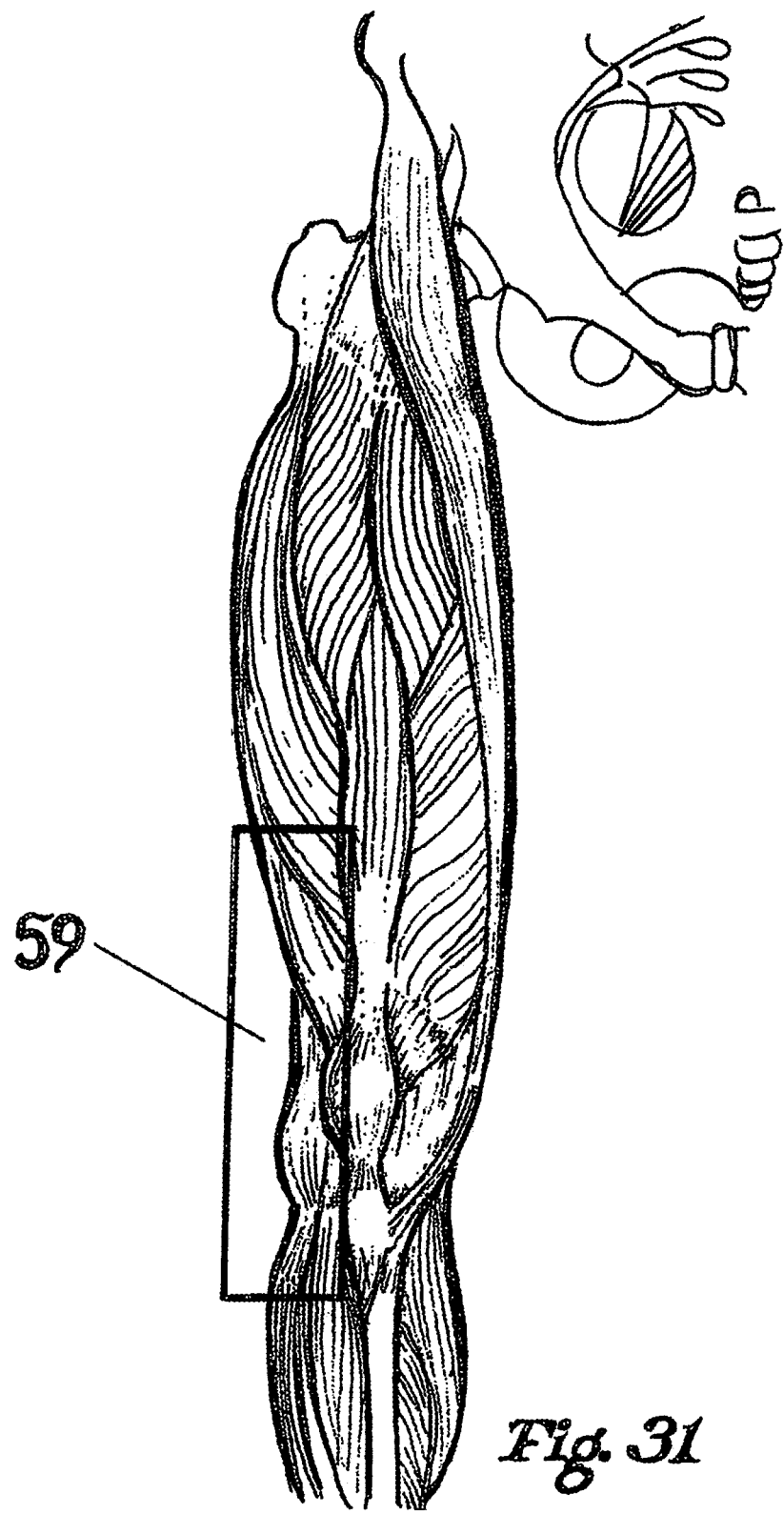
FIG. 31. is a drawing of the application of dynamic adhesive medical tape 59 applied laterally, distally to proximally, with tension for the elicitation of extension of the knee joint. The participant is positioned in a partially flexed position at their knee joint (when the tape is applied). The location of the tape is beyond the tibial tuberosity 50 down the entire length of the patellar ligament and across the tendon of the quadriceps femoris above the myotendinous junction of the rectus femoris 44.
Figure 32:
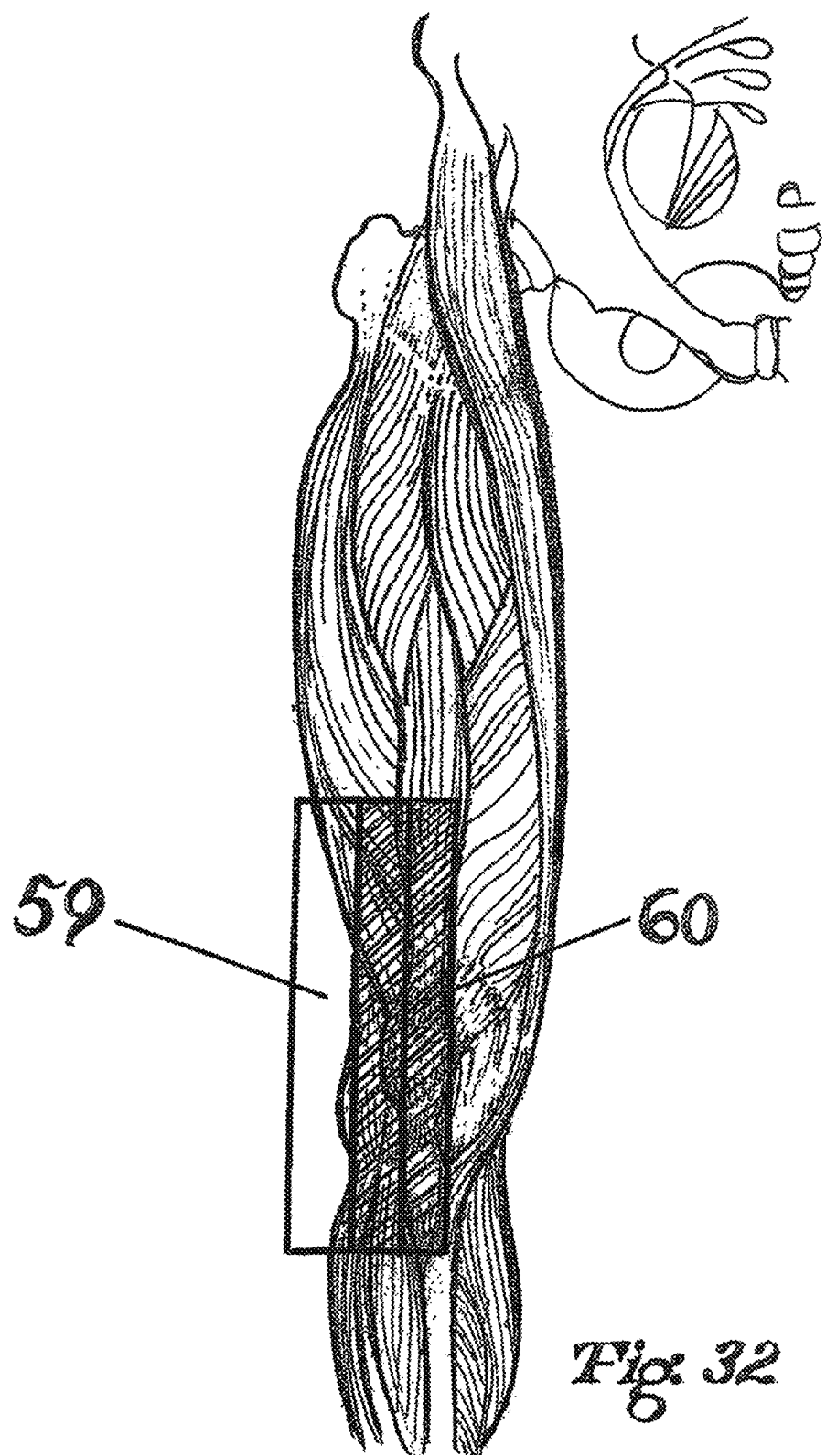
FIG. 32. is a drawing of the application of dynamic adhesive medical tape 60 applied medially to the first piece of tape 59 and distally to proximally with tension for the elicitation of extension of the knee joint. The participant is positioned in a partially flexed position at their knee joint (when the tape is applied). The location of the second piece of tape 60 is beyond the tibial tuberosity 50 down the entire length of the patellar ligament and across the tendon of the quadriceps femoris above the myotendinous junction of the rectus femoris 44. It is also overlapping the previous piece of tape 59 to further secure the tape 59.
Figure 33:
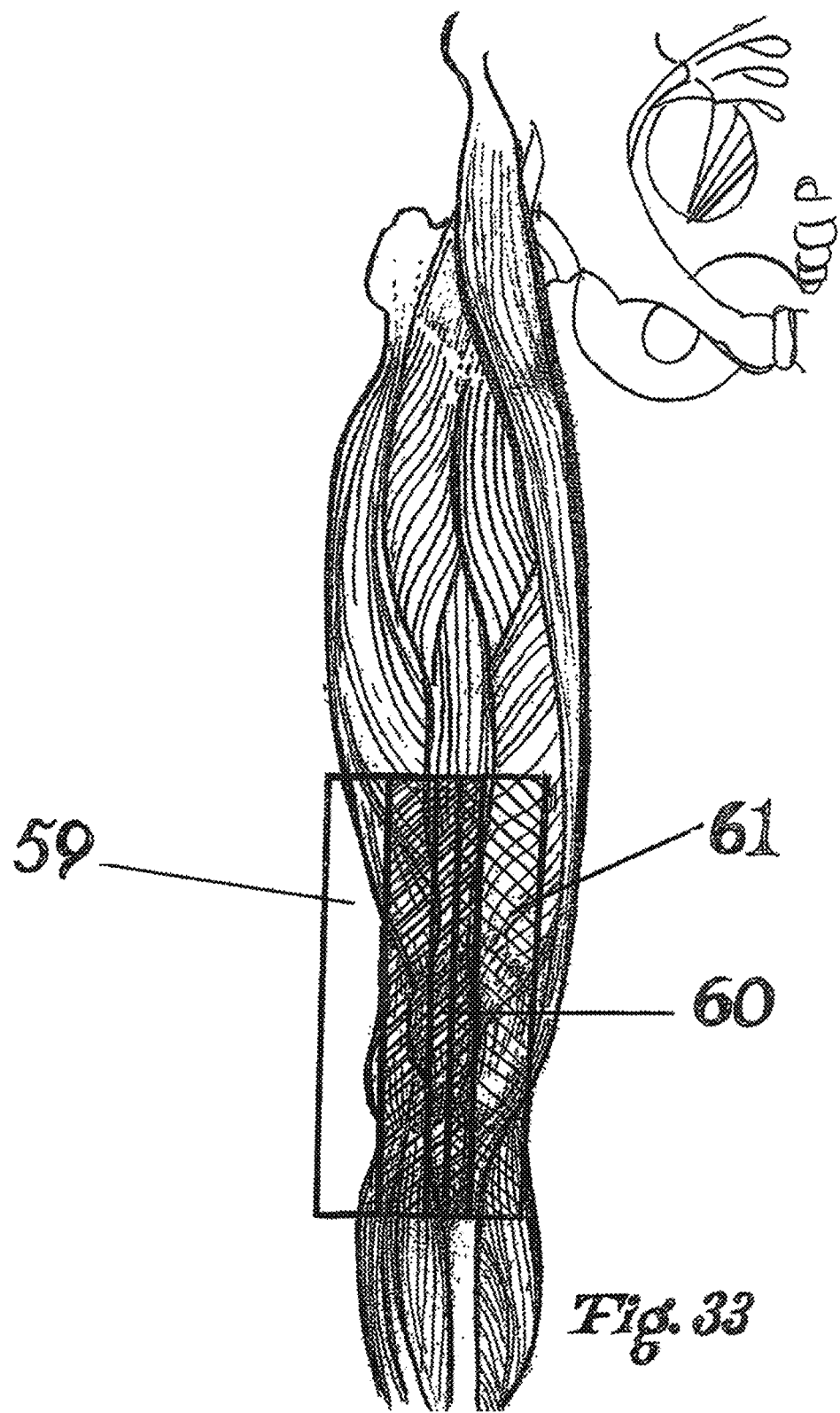
FIG. 33. is a drawing of the application of dynamic adhesive medical tape 61 applied medially to the second piece of tape 60 and distally to proximally with tension for the elicitation of extension of the knee joint. The participant is positioned in a partially flexed position at their knee joint (when the tape is applied). The location of the third piece of tape 61 is beyond the tibial tuberosity 50 down the entire length of the patellar ligament and across the tendon of the quadriceps femoris above the myotendinous junction of the rectus femoris 44. It is also overlapping the previous piece of tape 60 to further secure the tape 60.
Figure 34:
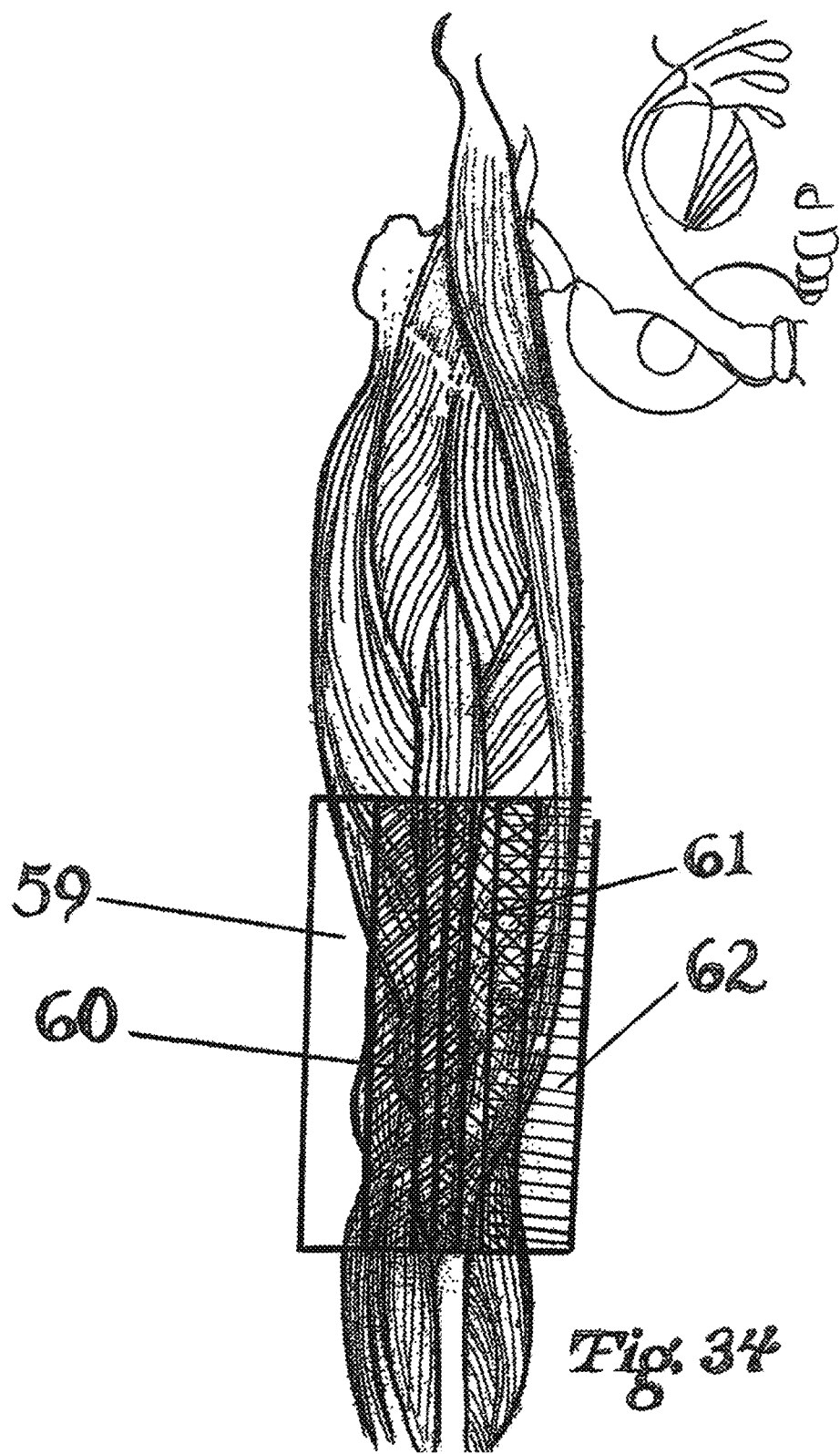
FIG. 34. is a drawing of the application of dynamic adhesive medical tape 62 applied distal to proximal with tension for the elicitation of extension of the knee joint. The participant is positioned in a partially flexed position at their knee joint (when the tape is applied). The location of the fourth piece of tape 62 is applied medially in relation to the third piece of tape 61 with some overlap to secure the tape 61.
Figure 35:
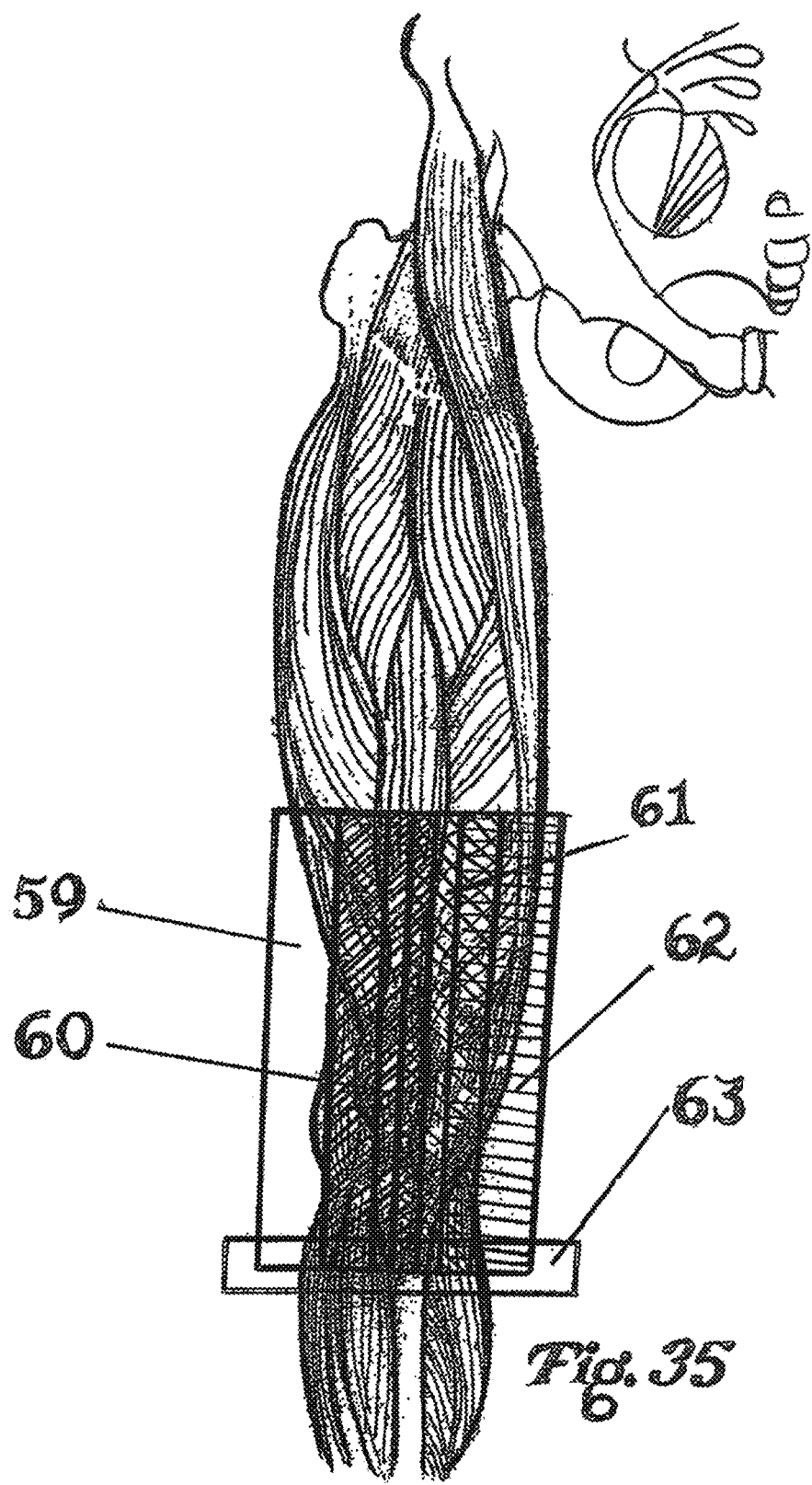
FIG. 35. is a drawing of the application of static adhesive medical tape 63 to anchor the distal region of dynamic adhesive medical tape 59, 60, 61, 62 encompassing all four pieces of tape.
Figure 36:
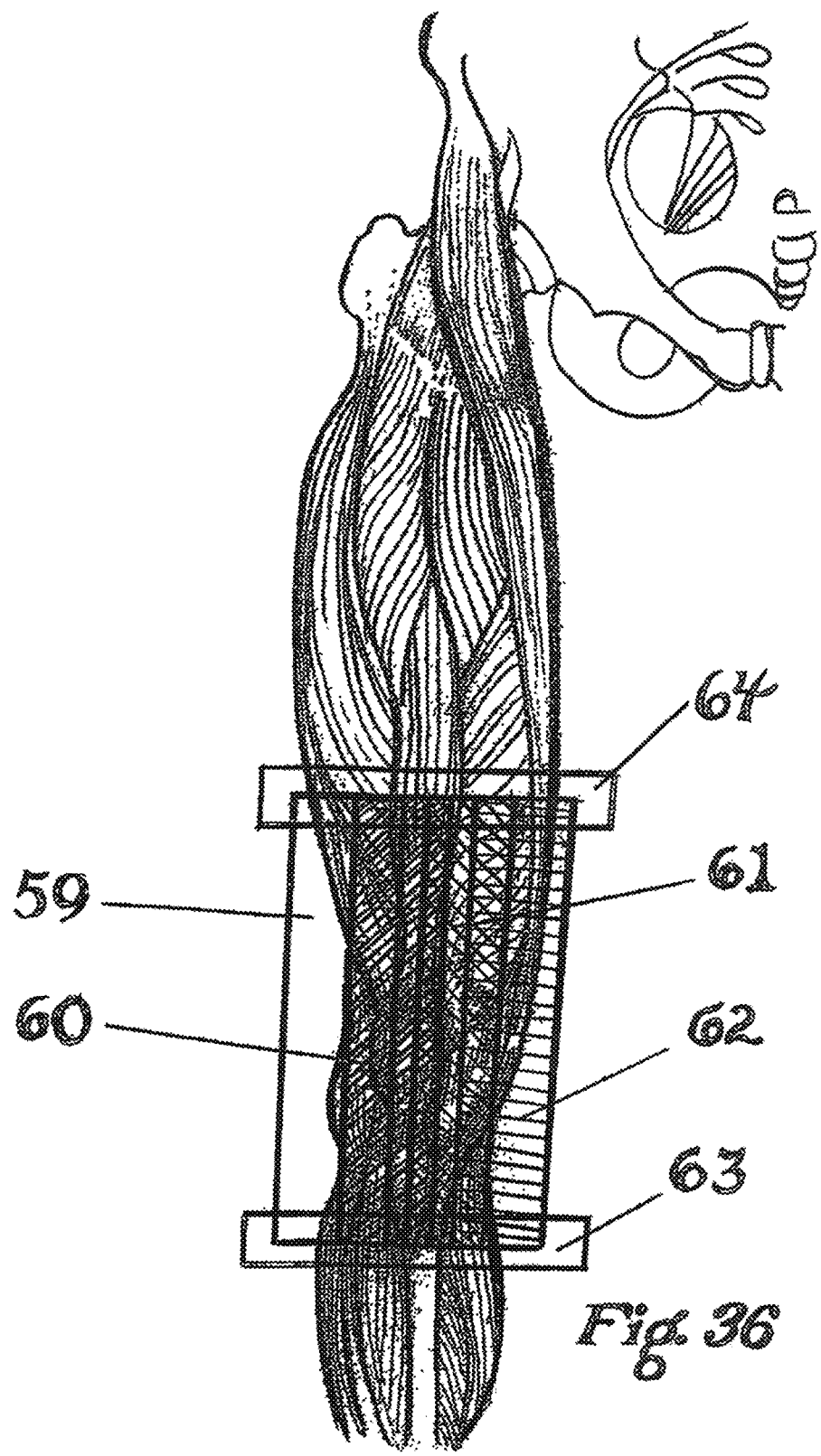
FIG. 36. is a drawing of the application of static adhesive medical tape 64 to anchor the proximal region of dynamic adhesive medical tape 59, 60, 61, 62 encompassing all four pieces of tape.

The invention claimed is:

1. A dynamic taping method of a joint to control tone in associated skeletal muscles:
   the joint including a joint capsule, fascia, retinaculum, at least one tendon, at least one ligament, and associated tensile structures; and
   the associated skeletal muscles including at least one agonist muscle and at least one antagonist muscle, each including a distal surface and a proximal surface, a distal myotendinous junction and a proximal myotendinous junction and a muscle belly; and
   the joint and associated skeletal muscles having proprioceptors and mechanoreceptors including Golgi tendon organs, Paciniform corpuscles, Pacinian corpuscles, Ruffini's endings, nuclear bag and nuclear chain fibers, interstitial type III and IV muscle receptors, and muscle spindle fibers, without penetrating skin, the method comprising the step of:
   avoiding muscle bellies, applying a first piece of dynamic adhesive medical tape in tension to the skin surface of the at least one agonist muscle and across the joint and in parallel to at least one tendon to place the Golgi tendon organs in tension, thereby eliciting increased muscle tone in the agonist muscle.

2. The method according to claim 1, wherein the dynamic adhesive medical tape lengthens the antagonist muscle spindle fibers, to immobilize the nuclear bag and nuclear chain fibers, thereby inhibiting muscle tone in the antagonist and eliciting muscle tone in the agonist.

3. The method according to claim 1, further comprising the step of:
   applying the tape across the joint to capture a part of the joint tendon.

4. The method according to claim 1, further comprising the step of:
   applying the tape across the joint to capture the entire joint tendon.

5. The method according to claim 1, further comprising the step of:
   applying the tape across the joint to capture the entire joint tendon and the myotendinous junction of the muscle associated with the joint.

6. The method according to claim 5, further comprising the step of:
   applying additional tape across the joint in parallel to the first piece of tape to capture the entire joint tendon and the myotendinous junction of the muscle associated with the joint.

7. The method according to claim 5, further comprising the step of:
   applying additional tape across the joint in parallel to the first piece of tape to capture the entire joint tendon and the myotendinous junction of a second muscle associated with the joint.

8. The method according to claim 5, further comprising the step of:
   applying the tape across the joint to capture the entire joint tendon, the myotendinous junction, and a at least a portion of the muscle associated with the joint.

9. The method according to claim 8, further comprising the step of:
   applying the tape across the joint to capture the entire joint tendon, the myotendinous junction, and at least a portion of the muscle associated with the joint and at least a portion of a second muscle associated with the joint.

10. The method according to claim 1, further comprising the step of:
    taping synergist muscles along with the agonist muscle to recruit additional tension and immobilize additional proprioceptors and mechanoreceptors.

11. The method according to claim 1, further comprising the step of:
    applying the tape distally to proximally across the joint.

12. The method according to claim 1, further comprising the step of:
    applying the tape laterally to medially.

13. The method according to claim 1, further comprising the step of:
    applying the tape cephalo to caudal.

14. The method according to claim 1, wherein the taping immobilizes the Paciniform corpuscles, and Pacinian corpuscles, Ruffini's ending, and interstitial type III and IV muscle receptors.

* * * * *